US012638457B2

(12) United States Patent
Ranum et al.

(10) Patent No.: US 12,638,457 B2
(45) Date of Patent: May 26, 2026

(54) RAN PROTEINS AS BIOMARKERS IN CAG/CTG EXPANSION DISORDERS

(71) Applicant: University of Florida Research Foundation, Incorporated, Gainesville, FL (US)

(72) Inventors: Laura Ranum, Gainesville, FL (US); Monica Banez Coronel, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1084 days.

(21) Appl. No.: 17/767,549

(22) PCT Filed: Oct. 9, 2020

(86) PCT No.: PCT/US2020/054976
§ 371 (c)(1),
(2) Date: Apr. 8, 2022

(87) PCT Pub. No.: WO2021/072187
PCT Pub. Date: Apr. 15, 2021

(65) Prior Publication Data
US 2024/0069039 A1    Feb. 29, 2024

Related U.S. Application Data

(60) Provisional application No. 62/913,662, filed on Oct. 10, 2019.

(51) Int. Cl.
G01N 33/68        (2006.01)

(52) U.S. Cl.
CPC ..... G01N 33/6875 (2013.01); G01N 2800/28 (2013.01)

(58) Field of Classification Search
None
See application file for complete search history.

(56) References Cited

U.S. PATENT DOCUMENTS

| | | | |
|---|---|---|---|
| 5,011,912 A | 4/1991 | Hopp et al. |
| 6,204,008 B1 | 3/2001 | Borneman et al. |
| 6,326,151 B1 | 12/2001 | Katze et al. |
| 6,342,581 B1 | 1/2002 | Rosen et al. |
| 7,008,796 B2 | 3/2006 | Wohlstadter et al. |
| 7,481,997 B1 | 1/2009 | Hardy |
| 8,993,633 B2 | 3/2015 | Megeney et al. |
| 9,448,232 B2 | 9/2016 | Petrucelli et al. |
| 10,066,007 B2 | 9/2018 | Edbauer et al. |
| 10,295,547 B2 | 5/2019 | Ranum et al. |
| 10,392,447 B2 | 8/2019 | Montrasio et al. |
| 10,509,045 B2 | 12/2019 | Ranum et al. |
| 10,663,475 B2 | 5/2020 | Ranum et al. |
| 10,940,161 B2 | 3/2021 | Ranum et al. |
| 10,961,322 B2 | 3/2021 | Montrasio et al. |

| | | | |
|---|---|---|---|
| 11,034,974 B2 | 6/2021 | Ling et al. |
| 11,345,911 B2 | 5/2022 | Ranum et al. |
| 11,903,910 B2 | 2/2024 | Ranum et al. |
| 12,025,622 B2 | 7/2024 | Ranum et al. |
| 12,162,952 B2 | 12/2024 | Grimm et al. |
| 12,360,124 B2 | 7/2025 | Ranum et al. |
| 12,364,707 B2 | 7/2025 | Ranum et al. |
| 12,392,786 B2 | 8/2025 | Ranum et al. |
| 12,436,154 B2 | 10/2025 | Ranum et al. |
| 12,473,545 B2 | 11/2025 | Ranum et al. |
| 2002/0165355 A1 | 11/2002 | Meheus et al. |
| 2003/0113826 A1 | 6/2003 | Wehner et al. |
| 2003/0233675 A1 | 12/2003 | Cao et al. |
| 2005/0042657 A1 | 2/2005 | Weese-Mayer et al. |
| 2006/0068434 A1 | 3/2006 | Stoerker |
| 2007/0004729 A1 | 1/2007 | Timmer et al. |
| 2007/0014810 A1 | 1/2007 | Baker et al. |
| 2007/0036760 A1 | 2/2007 | Wilson et al. |
| 2007/0093426 A1 | 4/2007 | Wormser |

(Continued)

FOREIGN PATENT DOCUMENTS

| | | |
|---|---|---|
| CA | 3137666 A1 | 11/2020 |
| EP | 2837390 A1 | 2/2015 |

(Continued)

OTHER PUBLICATIONS

Extended European Search Report, mailed Sep. 30, 2016, in connection with Application No. EP 14776090.4.
International Search Report and Written Opinion, mailed Aug. 22, 2014, in connection with Application No. PCT/US2014/022670.
International Preliminary Report on Patentability, mailed Sep. 24, 2015, in connection with Application No. PCT/US2014/022670.
International Search Report and Written Opinion, mailed Sep. 21, 2016, in connection with Application No. PCT/US2016/034738.
International Preliminary Report on Patentability, mailed Dec. 14, 2017, in connection with Application No. PCT/US2016/034738.

(Continued)

*Primary Examiner* — Michael D Pak
(74) *Attorney, Agent, or Firm* — Wolf, Greenfield & Sacks, P.C.

(57) ABSTRACT

Aspects of the disclosure relate to methods and compositions (e.g., kits) for detecting certain repeat-associated non-ATG (RAN) proteins in a subject (e.g., a subject having or suspected of having a disease associated with a CAG and/or CTG repeat expansion). In some embodiments, methods described by the disclosure comprise detecting one or more RAN proteins in a biological sample obtained from a subject by an immunoassay using one or more antibodies that target homopolymeric repeat regions of RAN proteins. In some embodiments, the disclosure relates to kits comprising one or more antibodies that target homopolymeric repeat regions of RAN proteins, and an immunoassay plate and/or reagents. In some embodiments, the disclosure provides methods of producing anti-RAN protein antibodies.

12 Claims, 44 Drawing Sheets

Specification includes a Sequence Listing.

(56) References Cited

U.S. PATENT DOCUMENTS

| | | |
|---|---|---|
| 2008/0188457 A1 | 8/2008 | Barlow et al. |
| 2008/0227699 A1 | 9/2008 | Chiba et al. |
| 2008/0248099 A1 | 10/2008 | Ishii |
| 2009/0074721 A1 | 3/2009 | Kim et al. |
| 2009/0143418 A1 | 6/2009 | Dixon et al. |
| 2009/0148866 A1 | 6/2009 | Datwyler et al. |
| 2009/0312395 A1 | 12/2009 | El-Tanani et al. |
| 2010/0298280 A1 | 11/2010 | Kioschis-Schneider et al. |
| 2012/0076785 A1 | 3/2012 | Nikolaev et al. |
| 2012/0094299 A1* | 4/2012 | Ranum ..................... C12N 9/12 |
| | | 435/7.1 |
| 2012/0142027 A1 | 6/2012 | Kim |
| 2012/0220534 A1 | 8/2012 | Levin et al. |
| 2013/0085169 A1 | 4/2013 | Baghdoyan et al. |
| 2013/0115603 A9 | 5/2013 | Ranum et al. |
| 2014/0100282 A1 | 4/2014 | Wong |
| 2014/0336133 A1 | 11/2014 | Miller et al. |
| 2015/0011729 A1 | 1/2015 | Ranum et al. |
| 2015/0361166 A1 | 12/2015 | Edbauer et al. |
| 2016/0025747 A1 | 1/2016 | Ranum et al. |
| 2016/0096800 A1 | 4/2016 | Walter et al. |
| 2016/0346297 A1 | 12/2016 | Sheehan |
| 2017/0247471 A1 | 8/2017 | Montrasio et al. |
| 2018/0050001 A1 | 2/2018 | During et al. |
| 2018/0088111 A1 | 3/2018 | Ni et al. |
| 2018/0292416 A1 | 10/2018 | Ranum et al. |
| 2019/0142858 A1 | 5/2019 | Ranum et al. |
| 2019/0153445 A1 | 5/2019 | Seow et al. |
| 2019/0285652 A1 | 9/2019 | Ranum et al. |
| 2020/0010567 A1 | 1/2020 | Montrasio et al. |
| 2020/0140846 A1 | 5/2020 | Ranum et al. |
| 2020/0206255 A9 | 7/2020 | Ranum et al. |
| 2020/0232925 A1 | 7/2020 | Ranum et al. |
| 2020/0241013 A1 | 7/2020 | Ranum et al. |
| 2020/0268691 A1 | 8/2020 | Ranum et al. |
| 2020/0341012 A1 | 10/2020 | Ranum et al. |
| 2020/0355701 A1 | 11/2020 | Van Meter |
| 2021/0236535 A1 | 8/2021 | Ranum et al. |
| 2021/0285970 A1 | 9/2021 | Ranum et al. |
| 2021/0347866 A1 | 11/2021 | Wang et al. |
| 2022/0153874 A1 | 5/2022 | Grimm et al. |
| 2022/0202935 A1 | 6/2022 | Edbauer et al. |
| 2022/0373559 A1 | 11/2022 | Ranum et al. |
| 2023/0002753 A1 | 1/2023 | Ranum et al. |
| 2023/0218730 A1 | 7/2023 | Ranum et al. |
| 2023/0288434 A1 | 9/2023 | Ranum et al. |
| 2024/0269093 A1 | 8/2024 | Ranum et al. |
| 2024/0393348 A1 | 11/2024 | Ranum et al. |
| 2024/0426844 A1 | 12/2024 | Ranum et al. |
| 2025/0027084 A1 | 1/2025 | Wolin et al. |
| 2025/0041247 A1 | 2/2025 | Ranum et al. |
| 2025/0164489 A1 | 5/2025 | Ranum et al. |
| 2025/0177431 A1 | 6/2025 | Richter et al. |
| 2025/0237666 A9 | 7/2025 | Ranum et al. |

FOREIGN PATENT DOCUMENTS

| | | |
|---|---|---|
| EP | 2948471 A1 | 12/2015 |
| EP | 3440100 A1 | 2/2019 |
| JP | H11-344491 A | 12/1999 |
| JP | 2004-510162 | 4/2004 |
| JP | 2004-518437 A | 6/2004 |
| JP | 2004-520803 A | 7/2004 |
| JP | 2007-507223 A | 3/2007 |
| JP | 2012-501193 A | 1/2012 |
| JP | 2016-515208 A | 5/2016 |
| JP | 2016-180665 A | 10/2016 |
| JP | 2017-019773 A | 1/2017 |
| JP | 2017-205118 A | 11/2017 |
| JP | 2018-031780 | 3/2018 |
| JP | 2019-515894 A | 6/2019 |
| WO | WO 2001/75067 A2 | 10/2001 |
| WO | WO 2001/081581 A2 | 11/2001 |
| WO | WO 2002/027317 A2 | 4/2002 |
| WO | WO 2002/040672 A2 | 5/2002 |
| WO | WO 2002/062945 A2 | 8/2002 |
| WO | WO 2005/033321 A2 | 4/2005 |
| WO | WO 2006/083800 A2 | 8/2006 |
| WO | WO 2009/144480 A1 | 12/2009 |
| WO | WO 2010/115033 A2 | 10/2010 |
| WO | WO 2010/132982 A1 | 11/2010 |
| WO | WO 2011/052906 A2 | 5/2011 |
| WO | WO 2012/159754 A2 | 11/2012 |
| WO | WO 2013/030588 A1 | 3/2013 |
| WO | WO 2013/061163 A2 | 5/2013 |
| WO | WO 2013/078375 A2 | 5/2013 |
| WO | WO 2013/172537 A1 | 11/2013 |
| WO | WO 2014/114303 A1 | 7/2014 |
| WO | WO 2014/114660 A1 | 7/2014 |
| WO | WO 2014/116865 A1 | 7/2014 |
| WO | WO 2014/159247 A1 | 10/2014 |
| WO | WO 2016/025692 A1 | 2/2016 |
| WO | WO 2016/050822 A2 | 4/2016 |
| WO | WO 2017/055612 A1 | 4/2017 |
| WO | WO 2017/176813 A1 | 10/2017 |
| WO | WO 2018/035408 A1 | 2/2018 |
| WO | WO 2018/195110 A1 | 10/2018 |
| WO | WO 2019/060918 A1 | 3/2019 |
| WO | WO 2019/067587 A1 | 4/2019 |
| WO | WO 2021/007110 A1 | 1/2021 |
| WO | WO 2021/055880 A1 | 3/2021 |
| WO | WO 2021/231887 A1 | 11/2021 |

OTHER PUBLICATIONS

Supplementary Partial European Search Report, mailed Oct. 18, 2019, in connection with Application No. EP 17779695.0.

Extended European Search Report, mailed Jan. 7, 2020, in connection with Application No. EP 17779695.0.

International Search Report and Written Opinion, mailed Jul. 7, 2017, in connection with Application No. PCT/US2017/026020.

International Preliminary Report on Patentability, mailed Oct. 18, 2018, in connection with Application No. PCT/US2017/026020.

Extended European Search Report, mailed Dec. 17, 2020, in connection with Application No. EP 18786964.9.

International Search Report and Written Opinion, mailed Jul. 27, 2018, in connection with Application No. PCT/US2018/028015.

International Preliminary Report on Patentability, mailed Oct. 31, 2019, in connection with Application No. PCT/US2018/028015.

Extended European Search Report, mailed Nov. 26, 2021, in connection with Application No. EP 18860923.4.

International Search Report and Written Opinion, mailed Jan. 15, 2019, in connection with Application No. PCT/US2018/052913.

International Preliminary Report on Patentability, mailed Apr. 9, 2020, in connection with Application No. PCT/US2018/052913.

Extended European Search Report, mailed Jun. 11, 2021, in connection with Application No. EP 18859783.5.

International Search Report and Written Opinion, mailed Dec. 6, 2018, in connection with Application No. PCT/US2018/052745.

International Preliminary Report on Patentability, mailed Apr. 9, 2020, in connection with Application No. PCT/US2018/052745.

International Search Report and Written Opinion, mailed Dec. 31, 2020, in connection with Application No. PCT/US2020/051670.

International Preliminary Report on Patentability, mailed Apr. 7, 2022, in connection with Application No. PCT/US2020/051670.

Invitation to Pay Additional Fees, mailed Feb. 9, 2021, in connection with Application No. PCT/US2020/054976.

International Search Report and Written Opinion, mailed Apr. 23, 2021, in connection with Application No. PCT/US2020/054976.

International Preliminary Report on Patentability, mailed Apr. 21, 2022, in connection with Application No. PCT/US2020/054976.

[No Author Listed] Amersham ECL Western Blotting Detection Reagent. Retrieved from the internet under https://www.cytivalifesciences.com/en/us/shop/protein-analysis/blotting-and-detection/blotting-standards-and-reagents/amersham-ecl-western-blotting-detection-reagent-p-05748 on Feb. 22, 2022, 6 pages.

[No Author Listed] EBNA1—Epstein-Barr nuclear antigen 1—Epstein-Barr virus (strain GD1) (HHV-4)—EBNA1 gene & protein, Jan.

(56)        References Cited

OTHER PUBLICATIONS 2018. 2018. Retrieved from the internet under https://www.uniprot.org/uniprot/Q3KSS4 on Sep. 12, 2018. 6 pages.

[No Author Listed], Abstracts. Medizinische Genetik, Berufsverband Nedizinische Genetik, Muchen, DE. Medgen. Mar. 4, 2016; 28(1):84-232. DOI: 10.1007/s11825-016-0083-5.

Ash et al., Unconventional translation of C9ORF72 GGGGCC expansion generates insoluble polypeptides specific to c9FTD/ALS. Neuron. Feb. 20, 2013;77(4):639-46. doi: 10.1016/j.neuron.2013.02.004. Epub Feb. 12, 2013.

Ashizawa et al., GGCCTG repeats put a hex on Purkinje cells and motor neurons in SCA36. Neurology. Jul. 24, 2012;79(4):302-3. doi: 10.1212/WNL.0b013e31826043d9. Epub Jun. 27, 2012.

Ayhan et al., SCA8 RAN polySer protein preferentially accumulates in white matter regions and is regulated by eIF3F. EMBO J. Oct. 1, 2018;37(19). pii: e99023. doi: 10.15252/embj.201899023. Epub Sep. 11, 2018.

Baboonian et al., Cross reaction of antibodies to a glycine/alanine repeat sequence of Epstein-Barr virus nuclear antigen-1 with collagen, cytokeratin, and actin. Ann Rheum Dis. Nov. 1991;50(11):772-5.

Bae et al., Antibody-aided clearance of extracellular a-synuclein prevents cell-to-cell aggregate transmission. J Neurosci. Sep. 26, 2012;32(39):13454-69.

Bañez-Coronel et al., A pathogenic mechanism in Huntington's disease involves small CAG-repeated RNAs with neurotoxic activity. PLoS Genet. 2012;8(2):e1002481. doi: 10.1371/journal.pgen.1002481. Epub Feb. 23, 2012.

Bañez-Coronel et al., RAN Translation in Huntington Disease. Neuron. Nov. 18, 2015;88(4):667-77. doi: 10.1016/j.neuron.2015.10.038.

Batra et al., Partners in crime: bidirectional transcription in unstable microsatellite disease. Hum Mol Genet. Apr. 15, 2010;19(R1):R77-82. doi: 10.1093/hmg/ddq132. Epub Apr. 4, 2010.

Carroll et al., Potent and selective antisense oligonucleotides targeting single-nucleotide polymorphisms in the Huntington disease gene / allele-specific silencing of mutant huntingtin. Mol Ther. Dec. 2011;19(12):2178-85. doi: 10.1038/mt.2011.201. Epub Oct. 4, 2011.

Chen et al., Functional genomics in *Drosophila* models of human disease. Briefings in Functional Genomics. Aug. 22, 2012;11(5):405-415.

Cleary et al., Repeat-associated non-ATG (RAN) translation in neurological disease. Hum Mol Genet. Oct. 15, 2013;22(R1):R45-51. doi: 10.1093/hmg/ddt371. Epub Aug. 4, 2013.

Donnelly et al., RNA toxicity from the ALS/FTD C9ORF72 expansion is mitigated by antisense intervention. Neuron. Oct. 16, 2013;80(2):415-28. doi: 10.1016/j.neuron.2013.10.015.

Duan et al., Generation of polyclonal antiserum for the detection of methylarginine proteins. J Immunol Methods. Mar. 30, 2007;320(1-2):132-42. Epub Feb. 6, 2007.

Duellman et al., Antigen-binding properties of monoclonal antibodies reactive with EBNA1 and use in immunoaffinity chromatography. PLoS One. 2009;4(2):e4614. doi: 10.1371/journal.pone.0004614. Epub Feb. 26, 2009.

Gkogkas et al., Pharmacogenetic inhibition of eIF4E-dependent Mmp9 mRNA translation reverses fragile X syndrome-like phenotypes. Cell Rep. Dec. 11, 2014;9(5):1742-1755. doi: 10.1016/j.celrep.2014.10.064. Epub Nov. 26, 2014.

Gómez-Tortosa et al., C9ORF72 hexanucleotide expansions of 20-22 repeats are associated with frontotemporal deterioration. Neurology. Jan. 22, 2013;80(4):366-70. doi: 10.1212/WNL.0b013e31827f08ea. Epub Jan. 2, 2013.

Hock et al., Antibodies against beta-amyloid slow cognitive decline in Alzheimer's disease. Neuron. May 22, 2003;38(4):547-54.

Jin et al., Metformin Protects Cells from Mutant Huntingtin Toxicity Through Activation of AMPK and Modulation of Mitochondrial Dynamics. Neuromolecular Med. Dec. 2016;18(4):581-592. doi: 10.1007/s12017-016-8412-z. Epub May 25, 2016. Author Manuscript, 19 pages.

Kearse et al., CGG Repeat-Associated Non-AUG Translation Utilizes a Cap-Dependent Scanning Mechanism of Initiation to Produce Toxic Proteins. Mol Cell. Apr. 21, 2016;62(2):314-322. doi: 10.1016/j.molcel.2016.02.034. Epub Mar. 31, 2016.

Leitman et al., ER stress-induced eIF2-alpha phosphorylation underlies sensitivity of striatal neurons to pathogenic huntingtin. PLoS One. Mar. 3, 2014;9(3):e90803. doi: 10.1371/journal.pone.0090803.

Ma et al., Metformin therapy in a transgenic mouse model of Huntington's disease. Neurosci Lett. Jan. 10, 2007;411(2):98-103. doi: 10.1016/j.neulet.2006.10.039. Epub Nov. 15, 2006.

Mirkin, Expandable DNA repeats and human disease. Nature. Jun. 21, 2007;447(7147):932-40. doi: 10.1038/nature05977.

Mori et al., The C9orf72 GGGGCC repeat is translated into aggregating dipeptide-repeat proteins in FTLD/ALS. Science. Mar. 15, 2013;339(6125):1335-8. doi: 10.1126/science.1232927. Epub Feb. 7, 2013. Supplementary information included.

Satoh et al., Dystrophic neurites express C9orf72 in Alzheimer's disease brains. Alzheimers Res Ther. Aug. 16, 2012;4(4):33. doi: 10.1186/alzrt136. 13 pages.

Sha et al., Treatment implications of C9ORF72. Alzheimer's Res Ther. Nov. 27, 2012;4(6):46. doi: 10.1186/alzrt149. eCollection 2012.

Shoesmith et al., Amyotrophic lateral sclerosis: update for family physicians. Can Fam Physician. Dec. 2006;52(12):1563-9.

Trouth et al., Myasthenia gravis: a review. Autoimmune Dis.;2012:874680. doi: 10.1155/2012/874680. Epub Oct. 31, 2012.

Vaughn et al., Inhibition of PKR protects against tunicamycin-induced apoptosis in neuroblastoma cells. Gene. Feb. 15, 2014;536(1):90-6. doi: 10.1016/j.gene.2013.11.074. Epub Dec. 14, 2013.

Wang et al., Comparative Analysis of VOCs in Exhaled Breath of Amyotrophic Lateral Sclerosis and Cervical Spondylotic Myelopathy Patients. Sci Rep. 2016;6:26120. Published May 23, 2016. doi: 10.1038/srep26120.

Welnowska et al., Translation of viral mRNA without active eIF2: the case of picornaviruses. PLoS One. 2011;6(7):e22230. doi: 10.1371/journal.pone.0022230. Epub Jul. 14, 2011.

Wojciechowska et al., RAN translation and frameshifting as translational challenges at simple repeats of human neurodegenerative disorders. Nucleic Acids Res. Oct. 29, 2014;42(19):11849-64. doi: 10.1093/nar/gku794. Epub Sep. 12, 2014.

Xiao et al., Isoform-specific antibodies reveal distinct subcellular localizations of C9orf72 in amyotrophic lateral sclerosis. Ann Neurol. Oct. 2015;78(4):568-83. doi: 10.1002/ana.24469. Epub Aug. 29, 2015.

Yanagisawa et al., Protein Binding of a DRPLA Family Through Arginine-Glutamic Acid Dipeptide repeats is Enhanced by Extended polyglutamine. Human Molecular Genetics. 2000;9(9):1433-1442.

Yu et al., Developing therapeutic antibodies for neurodegenerative disease. Neurotherapeutics. Jul. 2013;10(3):459-72. doi: 10.1007/s13311-013-0187-4.

Zhang et al., Aggregation-prone c9FTD/ALS poly(GA) RAN-translated proteins cause neurotoxicity by inducing ER stress. Acta Neuropathol. 2014;128:505-24.

Zhou et al., Antibodies inhibit transmission and aggregation of C9orf72 poly-GA dipeptide repeat proteins. EMBO Mol Med. May 2017;9(5):687-702. doi: 10.15252/emmm.201607054.

Zu et al., RAN proteins and RNA foci from antisense transcripts in C9ORF72 ALS and frontotemporal dementia. Proc Natl Acad Sci U S A. Dec. 17, 2013;110(51):E4968-77. doi: 10.1073/pnas.1315438110. Epub Nov. 18, 2013.

Extended European Search Report, mailed Oct. 4, 2023, in connection with application No. EP 20865149.7.

Invitation to Pay Additional Fees, mailed Nov. 30, 2020, in connection with Application No. PCT/US2020/051671.

International Search Report and Written Opinion, mailed Feb. 9, 2021, in connection with Application No. PCT/US2020/051671.

International Preliminary Report on Patentability, mailed Mar. 31, 2022, in connection with Application No. PCT/US2020/051671.

Extended European Search Report, mailed Aug. 25, 2023, in connection with Application No. EP 20869039.6.

(56)        References Cited

OTHER PUBLICATIONS

Extended European Search Report, mailed Oct. 4, 2023, in connection with application No. EP 20874343.5.

Invitation to Pay Additional Fees, mailed Mar. 30, 2023, in connection with Application No. PCT/US2022/051530.

International Search Report and Written Opinion, mailed May 25, 2023, in connection with Application No. PCT/US2022/051530.

International Search Report and Written Opinion, mailed Jul. 19, 2023, in connection with Application No. PCT/US2023/063328.

Bando et al., Double-strand RNA dependent protein kinase (PKR) is involved in the extrastriatal degeneration in Parkinson's disease and Huntington's disease. Neurochem Int. Jan. 2005;46(1):11-8. doi: 10.1016/j.neuint.2004.07.005.

Bañez-Coronel et al., Repeat-associated non-AUG (RAN) translation: insights from pathology. Lab Invest. Jul. 2019;99(7):929-942. doi: 10.1038/s41374-019-0241-x. Epub Mar. 27, 2019.

Bañez-Coronel et al., Sense and antisense RAN proteins in the CAG•CTG polyglutamine spinocerebellar ataxias. International Congress for Ataxia Research. Abstract ID 271. Nov. 1-4, 2022. 1 page.

Barzilai et al., Metformin as a Tool to Target Aging. Cell Metab. Jun. 14, 2016;23(6):1060-1065. doi: 10.1016/j.cmet.2016.05.011.

Benkirane et al., Oncogenic potential of TAR RNA binding protein TRBP and its regulatory interaction with RNA-dependent protein kinase PKR. EMBO J. Feb. 3, 1997;16(3):611-24. doi: 10.1093/emboj/16.3.611.

Brooks et al., Spinal and bulbar muscular atrophy: a trinucleotide-repeat expansion neurodegenerative disease. Trends Neurosci. Oct. 1995;18(10):459-61. doi: 10.1016/0166-2236(95)94497-s.

Castelli et al., Mechanisms of repeat-associated non-AUG translation in neurological microsatellite expansion disorders. Biochem Soc Trans. Apr. 30, 2021;49(2):775-792. doi: 10.1042/BST20200690.

Chen et al., Antidiabetic drug metformin (Glucophage$^R$) increases biogenesis of Alzheimer's amyloid peptides via up-regulating BACE1 transcription. Proc Natl Acad Sci U S A. Mar. 10, 2009;106(10):3907-12. doi: 10.1073/pnas.0807991106. Epub Feb. 23, 2009.

Cheng et al., C9ORF72 GGGGCC repeat-associated non-AUG translation is upregulated by stress through eIF2α phosphorylation. Nat Commun. Jan. 4, 2018;9(1):51. doi: 10.1038/s41467-017-02495-z.

Cleary et al., New developments in RAN translation: insights from multiple diseases. Curr Opin Genet Dev. Jun. 2017;44:125-134. doi: 10.1016/j.gde.2017.03.006. Epub Mar. 30, 2017. Author Manuscript, 18 pages.

Cleary et al., Repeat associated non-ATG (RAN) translation: new starts in microsatellite expansion disorders. Curr Opin Genet Dev. Jun. 2014;26:6-15. doi: 10.1016/j.gde.2014.03.002. Epub May 22, 2014. Author Manuscript, 20 pages.

Davidkin et al., Persistence of anti-mumps virus antibodies after a two-dose MMR vaccination. A nine-year follow-up. Vaccine. Nov. 1995;13(16):1617-22. doi: 10.1016/0264-410x(95)00064-8.

Foretz et al., Metformin: from mechanisms of action to therapies. Cell Metab. Dec. 2, 2014;20(6):953-66. doi: 10.1016/j.cmet.2014.09.018. Epub Oct. 30, 2014.

Gantois et al., Metformin ameliorates core deficits in a mouse model of fragile X syndrome. Nat Med. Jun. 2017;23(6):674-677. doi: 10.1038/nm.4335. Epub May 15, 2017.

Gray et al., Comparability of serum prostate-specific antigen measurement between the Roche Diagnostics Elecsys 2010 and the Abbott Architect i2000. Ann Clin Biochem. May 2004;41(Pt 3):207-12. doi: 10.1258/000456304323019578.

Green et al., RAN translation at C9orf72-associated repeat expansions is selectively enhanced by the integrated stress response. Nat Commun. Dec. 8, 2017;8(1):2005. doi: 10.1038/s41467-017-02200-0.

Guerra et al., Human gene profiling in response to the active protein kinase, interferon-induced serine/threonine protein kinase (PKR), in infected cells. Involvement of the transcription factor ATF-3 In PKR-induced apoptosis. J Biol Chem. Jul. 7, 2006;281(27):18734-45. doi: 10.1074/jbc.M511983200. Epub Apr. 13, 2006.

Jawaid et al., ALS disease onset may occur later in patients with pre-morbid diabetes mellitus. Eur J Neurol. May 2010;17(5):733-9. doi: 10.1111/j.1468-1331.2009.02923.x. Epub Jan. 13, 2010.

Kioumourtzoglou et al., Diabetes Mellitus, Obesity, and Diagnosis of Amyotrophic Lateral Sclerosis: A Population-Based Study. JAMA Neurol. Aug. 2015;72(8):905-11. doi: 10.1001/jamaneurol.2015.0910. Author Manuscript, 15 pages.

Koide et al., Unstable expansion of CAG repeat in hereditary dentatorubral-pallidoluysian atrophy (DRPLA). Nat Genet. Jan. 1994;6(1):9-13. doi: 10.1038/ng0194-9.

Koob et al., An untranslated CTG expansion causes a novel form of spinocerebellar ataxia (SCA8). Nat Genet. Apr. 1999;21(4):379-84. doi: 10.1038/7710.

Liu et al., C9orf72 BAC Mouse Model with Motor Deficits and Neurodegenerative Features of ALS/FTD. Neuron. May 4, 2016;90(3):521-34. doi: 10.1016/j.neuron.2016.04.005. Epub Apr. 21, 2016.

Memmott et al., Metformin prevents tobacco carcinogen--induced lung tumorigenesis. Cancer Prev Res (Phila). Sep. 2010;3(9):1066-76. doi: 10.1158/1940-6207.CAPR-10-0055. Epub Sep. 1, 2010.

Moon et al., Neuronal Regulation of eIF2α Function in Health and Neurological Disorders. Trends Mol Med. Jun. 2018;24(6):575-589. doi: 10.1016/j.molmed.2018.04.001. Epub Apr. 30, 2018.

Nguyen et al., Repeat-Associated Non-ATG Translation: Molecular Mechanisms and Contribution to Neurological Disease. Annu Rev Neurosci. Jul. 8, 2019;42:227-247. doi: 10.1146/annurev-neuro-070918-050405. Epub Mar. 25, 2019. Author Manuscript, 24 pages.

Pakos-Zebrucka et al., The integrated stress response. EMBO Rep. Oct. 2016;17(10):1374-1395. doi: 10.15252/embr.201642195. Epub Sep. 14, 2016.

Park et al., TAR RNA-binding protein is an inhibitor of the interferon-induced protein kinase PKR. Proc Natl Acad Sci U S A. May 24, 1994;91(11):4713-7. doi: 10.1073/pnas.91.11.4713.

Peel et al., Double-stranded RNA-dependent protein kinase, PKR, binds preferentially to Huntington's disease (HD) transcripts and is activated in HD tissue. Hum Mol Genet. Jul. 15, 2001;10(15):1531-8. doi: 10.1093/hmg/10.15.1531.

Perez et al., CCG•CGG interruptions in high-penetrance SCA8 families increase RAN translation and protein toxicity. EMBO Mol Med. Nov. 8, 2021;13(11):e14095. doi: 10.15252/emmm.202114095. Epub Oct. 11, 2021.

Sonenberg et al., Regulation of translation initiation in eukaryotes: mechanisms and biological targets. Cell. Feb. 20, 2009;136(4):731-45. doi: 10.1016/j.cell.2009.01.042.

Soragni et al., Repeat-Associated Non-ATG (RAN) Translation in Fuchs' Endothelial Corneal Dystrophy. Invest Ophthalmol Vis Sci. Apr. 1, 2018;59(5):1888-1896. doi: 10.1167/iovs.17-23265.

Taylor et al., Decoding ALS: from genes to mechanism. Nature. Nov. 10, 2016;539(7628):197-206. doi: 10.1038/nature20413. Author Manuscript, 28 pages.

Tian et al., Expanded CUG repeat RNAs form hairpins that activate the double-stranded RNA-dependent protein kinase PKR. RNA. Jan. 2000;6(1):79-87. doi: 10.1017/s1355838200991544.

Todd et al., CGG repeat-associated translation mediates neurodegeneration in fragile X tremor ataxia syndrome. Neuron. May 8, 2013;78(3):440-55. doi: 10.1016/j.neuron.2013.03.026. Epub Apr. 18, 2013. Erratum in: Neuron. Jul. 24, 2013;79(2):402.

Todd et al., Insights into the pathogenic mechanisms of Chromosome 9 open reading frame 72 (C9orf72) repeat expansions. J Neurochem. Aug. 2016;138 Suppl 1:145-62. doi: 10.1111/jnc.13623. Epub Jun. 15, 2016.

Tsuji, S., Dentatorubral-pallidoluysian atrophy. Handb Clin Neurol. 2012; 103:587-94. doi: 10.1016/B978-0-444-51892-7.00041-3.

Vishwakarma et al., Current molecular insight to reveal the dynamics of CAG repeating units in spinocerebellar ataxia. Intractable Rare Dis Res. May 2018;7(2):79-86. doi: 10.5582/irdr.2018.01039.

Wieben et al., Amplification-free long-read sequencing of TCF4 expanded trinucleotide repeats in Fuchs Endothelial Corneal Dystrophy. PLoS One. Jul. 5, 2019;14(7):e0219446. doi: 10.1371/journal.pone.0219446.

Zhu et al., Suppression of PKR promotes network excitability and enhanced cognition by interferon-γ-mediated disinhibition. Cell. Dec. 9, 2011;147(6):1384-96. doi: 10.1016/j.cell.2011.11.029.

(56)　　　　References Cited

OTHER PUBLICATIONS

Zu et al., Metformin inhibits RAN translation through PKR pathway and mitigates disease in C9orf72 ALS/FTD mice. Proc Natl Acad Sci U S A. Aug. 4, 2020;117(31):18591-18599. doi: 10.1073/pnas. 2005748117. Epub Jul. 20, 2020. Supplementary Materials, 33 pages.

Zu et al., Non-ATG-initiated translation directed by microsatellite expansions. Proc Natl Acad Sci U S A. Jan. 4, 2011;108(1):260-5. doi: 10.1073/pnas.1013343108. Epub Dec. 20, 2010.

Zu et al., RAN Translation Regulated by Muscleblind Proteins in Myotonic Dystrophy Type 2. Neuron. Sep. 13, 2017;95(6):1292-1305.e5. doi: 10.1016/j.neuron.2017.08.039.

International Preliminary Report on Patentability, mailed Jun. 13, 2024, in connection with Application No. PCT/US2022/051530.

International Preliminary Report on Patentability, mailed Sep. 12, 2024, in connection with Application No. PCT/US2023/063328.

[No Author Listed] CRC group Top> L. K. Housing> Query, after sampling and sampling, was conducted, kept still in whole blood ; CRC Corporation, Jun. 30, 2013. https://web.archive.org/web/20130630024235/http://www.crc-group.co.jp/crc/q_and_a/149.html.

Alaoui-Ismaili et al., Design of second generation therapeutic recombinant bone morphogenetic proteins. Cytokine Growth Factor Rev. Oct.-Dec. 2009;(5-6):501-7. doi: 10.1016/j.cytogfr.2009.10. 001. Epub Nov. 11, 2009.

Asokan et al., The AAV vector toolkit: poised at the clinical crossroads. Mol Ther. Apr. 2012;20(4):699-708. doi: 10.1038/mt. 2011.287. Epub Jan. 24, 2012.

Atwood et al., A Unified Hypothesis of Early- and Late-Onset Alzheimer's Disease Pathogenesis. J Alzheimers Dis. 2015;47(1):33-47. doi: 10.3233/JAD-143210.

Brujin et al., Unraveling the mechanisms involved in motor neuron degeneration in ALS. Annu Rev Neurosci. 2004;27:723-49. doi: 10.1146/annurev.neuro.27.070203.144244.

Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990; 111(5 Pt 1):2129-38. doi: 10.1083/jcb.111.5.2129.

Cendelin et al., Consensus Paper: Strengths and Weaknesses of Animal Models of Spinocerebellar Ataxias and Their Clinical Implications. Cerebellum. Jun. 2022;21(3):452-481. doi: 10.1007/s12311-021-01311-1. Epub Aug. 10, 2021.

Cui et al., Spinocerebellar ataxias: from pathogenesis to recent therapeutic advances. Front Neurosci. Jun. 4, 2024;18:1422442. doi: 10.3389/fnins.2024.1422442.

Gendron et al., Cerebellar c9RAN proteins associate with clinical and neuropathological characteristics of C9ORF72 repeat expansion carriers. Acta Neuropathol. Oct. 2015;130(4):559-73. doi: 10.1007/s00401-015-1474-4. Epub Sep. 8, 2015.

Gendron et al., Poly(GP) proteins are a useful pharmacodynamic marker for C9ORF72-associated amyotrophic lateral sclerosis. Sci Transl Med. Mar. 29, 2017;9(383):eaai7866. doi: 10.1126/scitranslmed. aai7866.

Guo et al., Protein tolerance to random amino acid change. Proc Natl Acad Sci U S A. Jun. 22, 2004;101(25):9205-10. doi: 10.1073/pnas.0403255101. Epub Jun. 14, 2004.

Guo et al., RAN proteins in neurodegenerative disease: Repeating themes and unifying therapeutic strategies. Curr Opin Neurobiol. Feb. 2022;72:160-170. doi: 10.1016/j.conb.2021.11.001. Epub Dec. 22, 2021.

Henstridge et al., Beyond the neuron-cellular interactions early in Alzheimer disease pathogenesis. Nat Rev Neurosci. Feb. 2019;20(2):94-108. doi: 10.1038/s41583-018-0113-1.

Ju et al., A yeast model of FUS/TLS-dependent cytotoxicity. PLoS Biol. Apr. 2011;9(4):e1001052. doi: 10.1371/journal.pbio.1001052. Epub Apr. 26, 2011.

Lagier-Tourenne et al., TDP-43 and FUS/TLS: emerging roles in RNA processing and neurodegeneration. Hum Mol Genet. Apr. 15, 2010;19(R1):R46-64. doi: 10.1093/hmg/ddq137. Epub Apr. 15, 2010.

Pawson et al., Assembly of cell regulatory systems through protein interaction domains. Science. Apr. 18, 2003;300(5618):445-52. doi: 10.1126/science.1083653.

Ranganathan et al., Multifaceted Genes in Amyotrophic Lateral Sclerosis-Frontotemporal Dementia. Front Neurosci. Jul. 7, 2020;14:684. doi: 10.3389/fnins.2020.00684.

Rothstein, Therapeutic horizons for amyotrophic lateral sclerosis. Curr Opin Neurobiol. Oct. 1996;6(5):679-87. doi: 10.1016/s0959-4388(96)80103-6.

Sarter, Animal cognition: defining the issues. Neurosci Biobehav Rev. Nov. 2004;28(7):645-50. doi: 10.1016/j.neubiorev.2004.09. 005.

Swerdlow, Pathogenesis of Alzheimer's disease. Clin Interv Aging. 2007;2(3):347-59.

Tandon et al., Polyglutamine disorders: Pathogenesis and potential drug interventions. Life Sci. May 1, 2024;344:122562. doi: 10.1016/j.lfs.2024.122562. Epub Mar. 14, 2024.

Tayebati, Animal models of cognitive dysfunction. Mech Ageing Dev. Feb. 2006; 127(2):100-8. doi: 10.1016/j.mad.2005.09.026. Epub Nov. 15, 2005.

William et al., Old friends on new paths: metformin as an early phase treatment in Huntington's Disease?, Medizinische Genetik, 28, pp. 215-216, Mar. 4, 2016 (Mar. 4, 2016) (Abstract).

Williams et al., CCNF mutations in amyotrophic lateral sclerosis and frontotemporal dementia. Nat Commun. Apr. 15, 2016;7:11253. doi: 10.1038/ncomms11253.

Anger, Animal test systems to study behavioral dysfunctions of neurodegenerative disorders. Neurotoxicology. 1991 Fall;12(3):403-13.

Murase et al., Drug Discovery Research Toward the Small Molecular Therapeutic Agents for Repeat Expansion Diseases, Nagasaki International University Review, Mar. 2022, vol. 22, pp. 177-185.

* cited by examiner

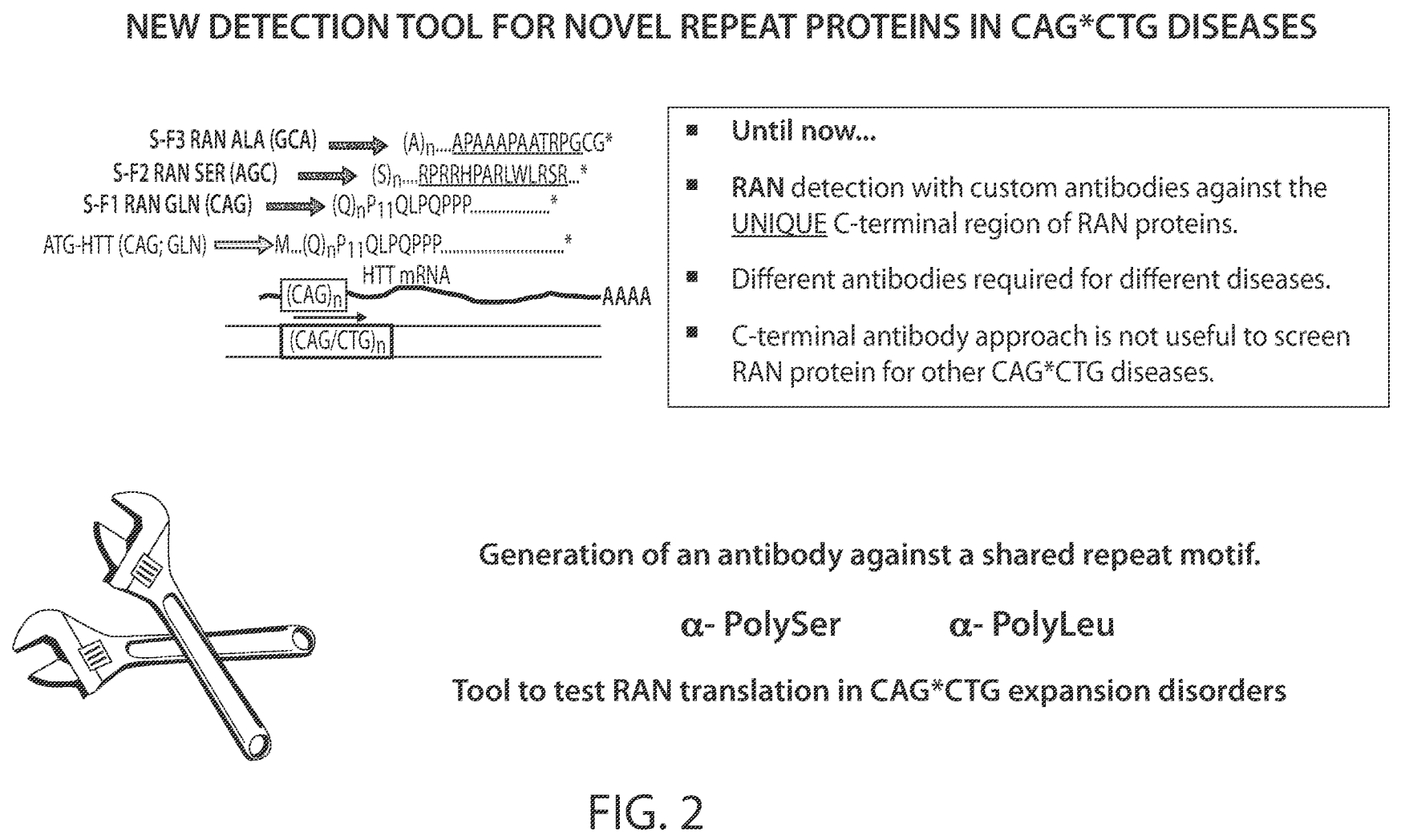

NEW DETECTION TOOL FOR NOVEL REPEAT PROTEINS IN CAG*CTG DISEASES

S-F3 RAN ALA (GCA) ⟶ (A)ₙ....APAAAPAATRPGCG*

S-F2 RAN SER (AGC) ⟹ (S)ₙ....RPRRHPARLWLRSR.*

S-F1 RAN GLN (CAG) ⟹ (Q)ₙP₁₁QLPQPPP........*

ATG-HTT (CAG; GLN) ⟹M....(Q)ₙP₁₁QLPQPPP.........*

HTT mRNA ‿‿‿AAAA

[CAG]ₙ

[CAG/CTG]ₙ

▓ Until now...

▓ RAN detection with custom antibodies against the UNIQUE C-terminal region of RAN proteins.

▓ Different antibodies required for different diseases.

▓ C-terminal antibody approach is not useful to screen RAN protein for other CAG*CTG diseases.

Generation of an antibody against a shared repeat motif.

α- PolySer     α- PolyLeu

Tool to test RAN translation in CAG*CTG expansion disorders

FIG. 2

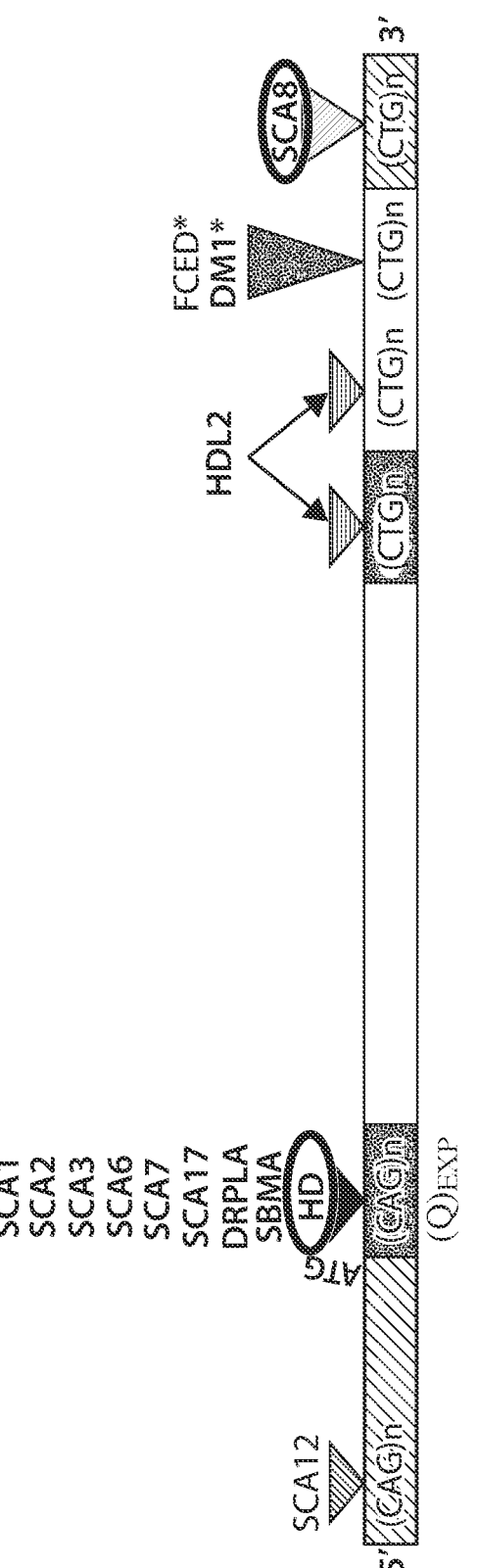
FIG. 3

α–PolySER detects polySer PROTEIN in transfected cells

α-PolySER antibody also detects protein by western blot

α-POLYSER ANTIBODY SHOWS SIMILAR AGGREGATES FOUND W/ C-TERM ANTIBODIES

α-polySER detects RAN positive cells in HD but not control human striatum

*SIMILAR RESULTS WITH α-polySER AND SCA8 SER-CT ANTIBODIES

PolySer RAN proteins accumulate in additional polyGlutamine diseases: SCA1.

NOVEL α-polySer

CONTROL    SCA1

GCL
PCL
MCL

WHITE
MATTER

DEEP
WHITE
MATTER

SCA1

6    39   41      83

Normal repeat range
Pathogenic repeat range

Serine frame (AGC)
*ARRRDTRLSSSSSSSSSSSSISISSSSSSSSSSSSSSSTSAGLR
GSSPRGPPHQPSRTSTSTFPVLRRTPAAPPLLRPSPSTSTPT
RR*

FIG. 8

PolySer RAN proteins accumulate in additional polyGlutamine disease: SCA2.

NOVEL α-polySer

CONTROL    SCA2

GCL
PCL
MCL

WHITE MATTER

DEEP WHITE MATTER

3 SCA2 cases
8 control cases

CAG expansion mutations in the ATXN2 gene 5871 (G→C)
2 (T→C)

(CCG)nCCC  SCA2 gene

D12S1672

...(CAG)n.

14  32  34    77    Normal repeat range
                    Pathogenic repeat range Serine frame (AGC)
*SPSSSSSSSSSSSSSSNSSSSS......SSSSRRPRLPMSASPAAAAF*

α-PolySER and α-polyGln show different distribution pattern in SCA2

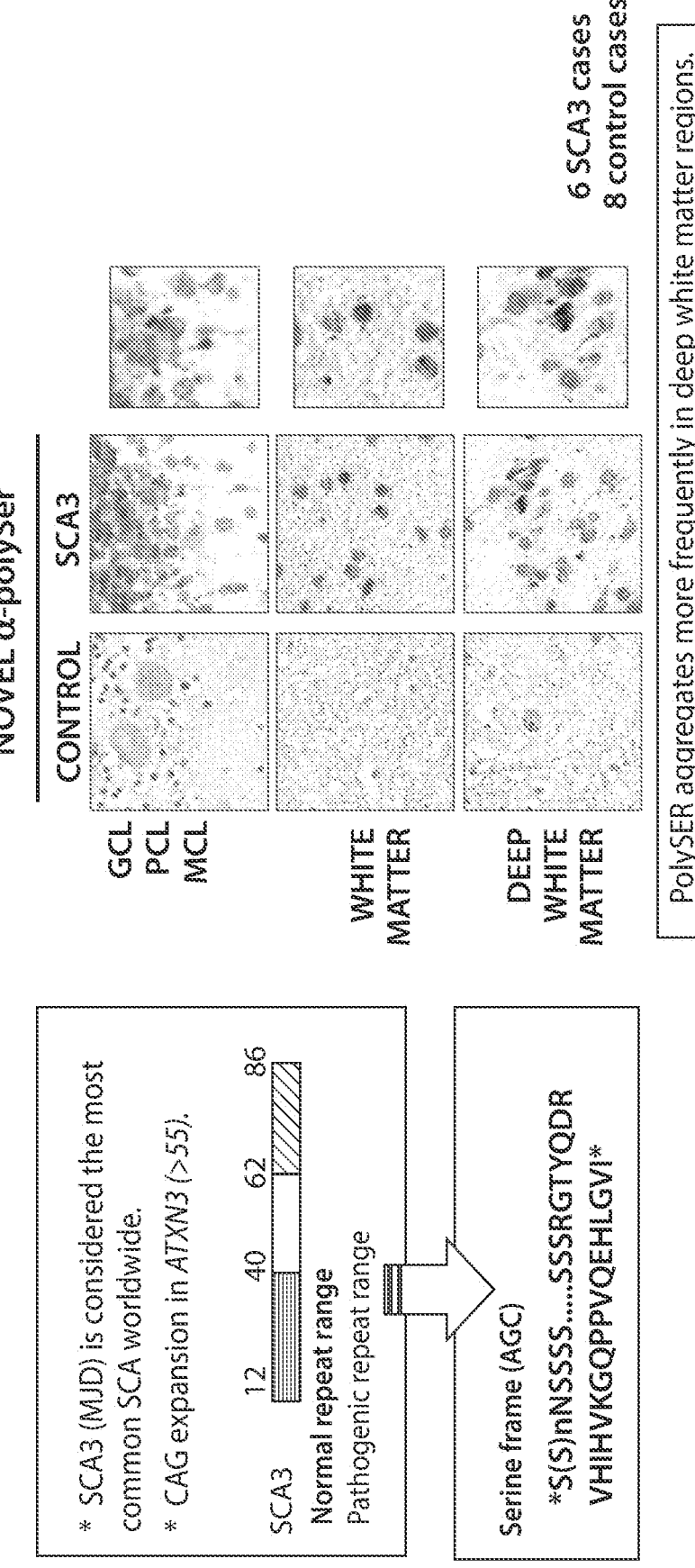

α-PolySER immunopositive cells in additional spinocerebellar ataxias: SCA3.

NOVEL α-polySer

CONTROL     SCA3

GCL
PCL
MCL

WHITE MATTER

DEEP WHITE MATTER

6 SCA3 cases
8 control cases

PolySER aggregates more frequently in deep white matter regions.

* SCA3 (MJD) is considered the most common SCA worldwide.
* CAG expansion in *ATXN3* (>55).

12   40   62   86

SCA3
Normal repeat range
Pathogenic repeat range

Serine frame (AGC)

*S(S)nNSSSS.....SSSRGTYQDR
VHIHVKGQPPVQEHLGVI*

FIG. 13

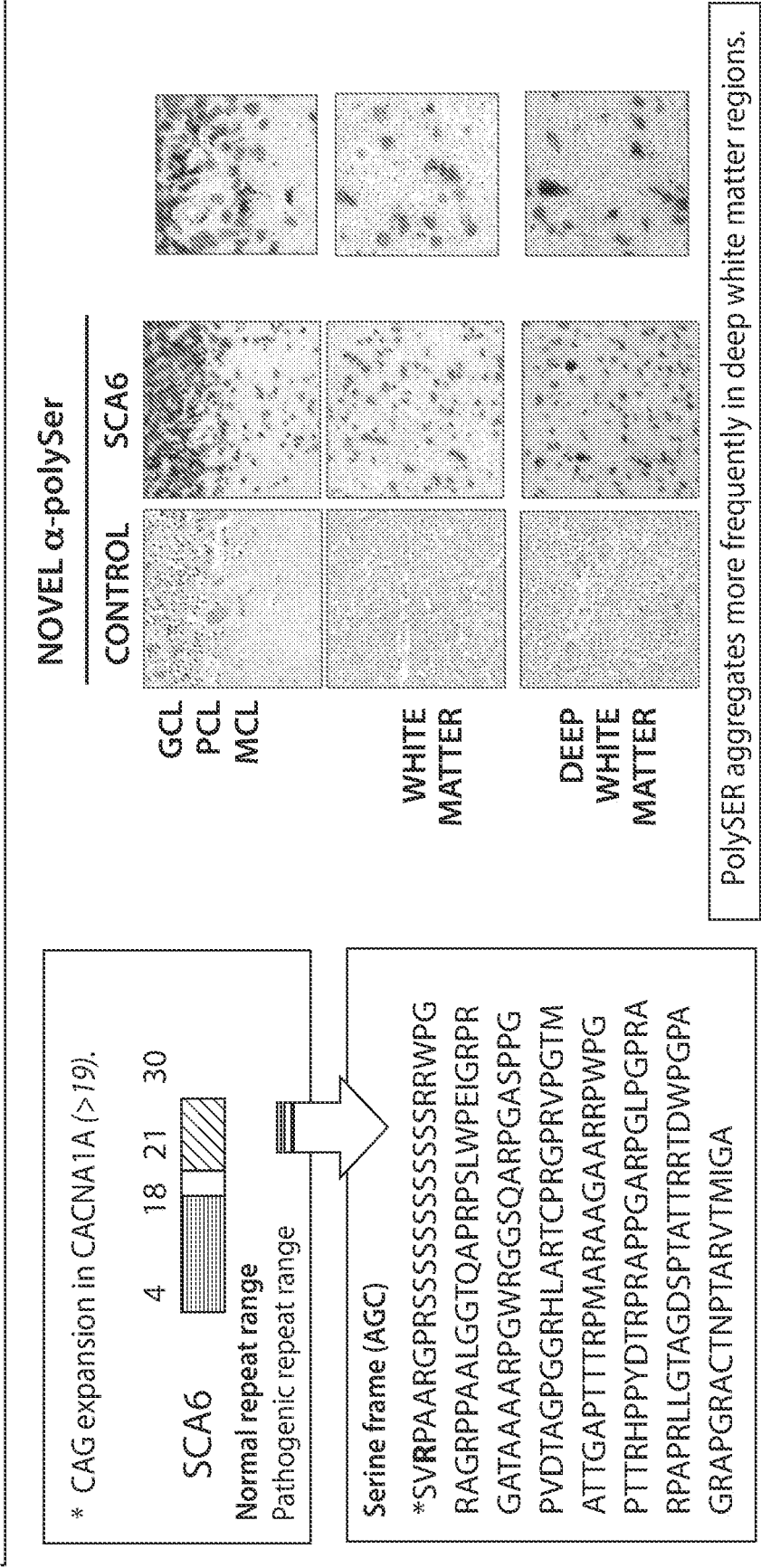

α-PolySER immunopositive cells in additional spinocerebellar ataxias: SCA6.

NOVEL α-polySer

CONTROL    SCA6

GCL
PCL
MCL

WHITE MATTER

DEEP WHITE MATTER

PolySER aggregates more frequently in deep white matter regions.

* CAG expansion in CACNA1A (>19).

SCA6    4    18   21   30

Normal repeat range
Pathogenic repeat range

Serine frame (AGC)

*SVRPAARGPRSSSSSSSSRRWPG
RAGRPPAALGGTQAPRPSLWPEIGRPR
GATAAAARPGWRGGSQARPGASPPG
PVDTAGPGGRHLARTCPRGPRVPGTM
ATTGAPTTTRPMARAAGAARRPWPG
PTTRHPPYDTRPRAPPGARPGLPGPRA
RPAPRLLGTAGDSPTATTRRTDWPGPA
GRAPGRACTNPTARVTMIGA

FIG. 16

Predicted secondary structure of α1-ACT

5xCAG    9xCAG    20xCAG

Examples of α-PolySER staining in DM1 frontal cortex

VARIABILITY IN POLYSER ACCUMULATION ACROSS CASES

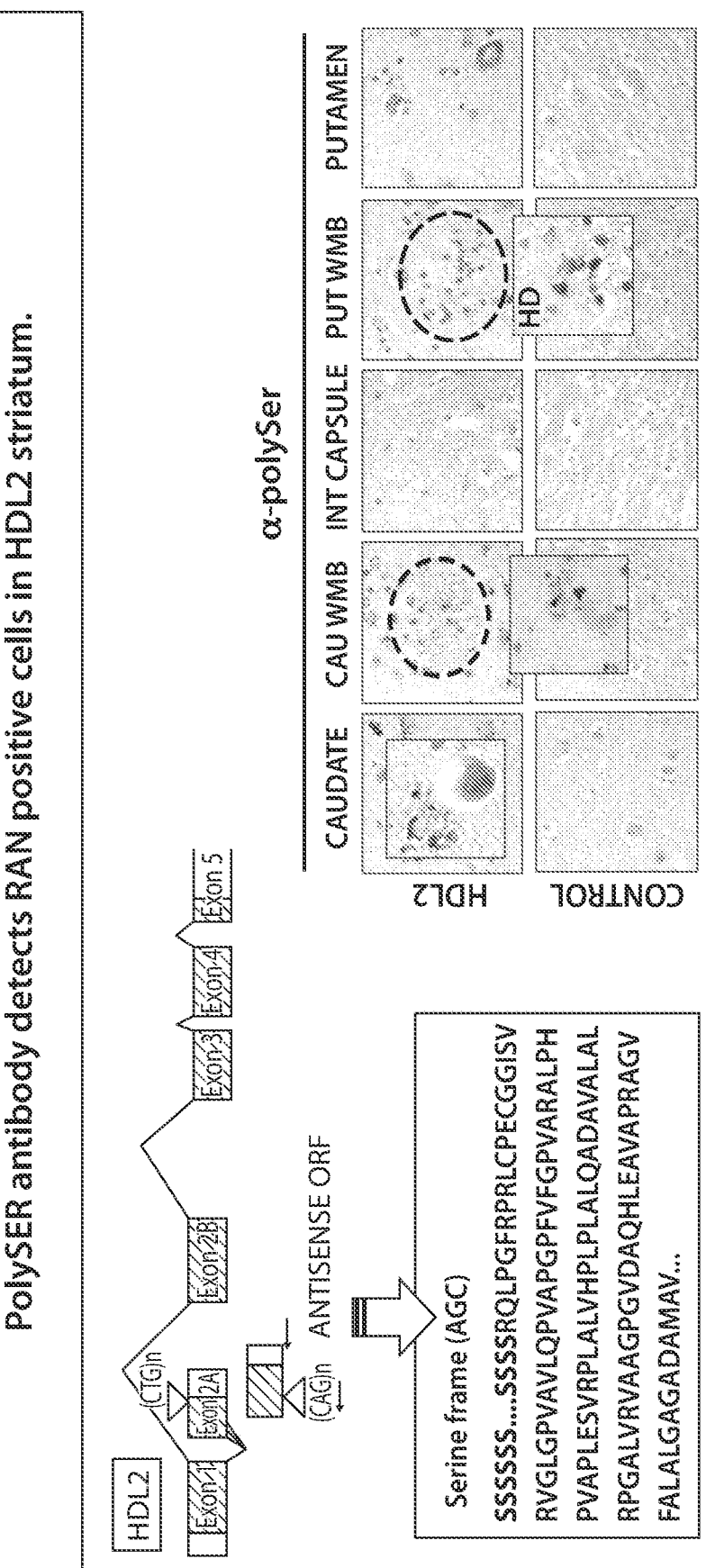

PolySER antibody detects RAN positive cells in HDL2 striatum.

α-polySer

CAUDATE    CAU WMB    INT CAPSULE    PUT WMB    PUTAMEN

HDL2

CONTROL

3 HDL2 cases
8 control cases

HDL2

Exon 1    Exon 2A    Exon 2B    Exon 3    Exon 4    Exon 5
(CTG)n    (CAG)n

ANTISENSE ORF

Serine frame (AGC)

SSSSS....SSSSRQLPGFRPRLCPECGGISV
RVGLGPVAVLQPVAPGPFVFGPVARALPH
PVAPLESVRPLALVHPLPLALQADAVALAL
RPGALVRVAAGPGVDAQHLEAVAPRAGV
FALALGAGADAMAV...

PolySER mostly accumulates in neurons and astrocytes of Caudate and Putamen.
Both soluble and aggregated forms are frequently found.

FIG. 21

Validation of α-PolyLEU antibody

α-polyLeu novel antibody selectively detects recombinant poly-Leu protein by IF and polyLeucine aggregates in HD frontal cortex by iHC Antisense polyLeu accumulates in the cerebellum of "polyGlutamine" SCAs Antisense polyLeu accumulates in the cerebellum of "polyGlutamine" SCAs PolyLEU antibody detects RAN positive cells in HDL2 striatum.

IMMUNOSTAINING SUMMARY

| | SAMPLE ID | Bergmann glia | WM | Deep WM | Observations |
|---|---|---|---|---|---|
| | | | PolySerine | | |
| SCA1 | CNGA-0018 | ++ | ++ | + | |
| | 2553 | +++ | +++ | ++++ | |
| | SCA1 HO | ++ | +++ | ++ | |
| SCA2 | CNGA-0005 | ++++ | ++++ | ++++ | |
| | CNGA-0023 | +++ | +++ | ++++ | |
| | 1959 | ++ | ++ | ++ | |
| SCA3 | CNGA-0007 | - | +++ | ++++ | |
| | CNGA-0010 | - | + | ++ | |
| | CNGA-0021 | ++++ | +++++ | ++++ | Macroaggregates in dentate |
| | CNGA-0022 | ++ | +++ | ++++ | |
| | 1980 | + | ++ | ++ | |
| | 2123 | +++ | +++ | +++ | |
| SCA6 | CNGA-0013 | +++ | +++ | +++ | |
| | CNGA-0025 | ++ | ++ | ++ | |
| | CNGA-0038 | ++ | ++ | +++ | |
| | 315 | + | + | +++ | Around vessels |
| SCA7 | CNGA-0004 | ++ | + | + | |
| | CNGA-0026 | +++ | +++ | ++++ | Macroaggregates in dentate |
| CTRL | 702 | - | - | - | |
| | 706 | - | - | - | |
| | 07-053 | - | - | - | |
| | 07-60 | - | - | - | |
| | atrophy 18-1527 | - | - | - | |
| | PSP 2588 | + | ++ | + | |
| | PSP 2623 | - | + | ++ | |
| | SCA5 IX-08 | - | - | - | |

Stainings using preinmune serum Are clean, not giving any significant signal

Both polySer polyclonals 713 and 714 gave similar stainings in the samples tested

Cerebellum

FIG. 36

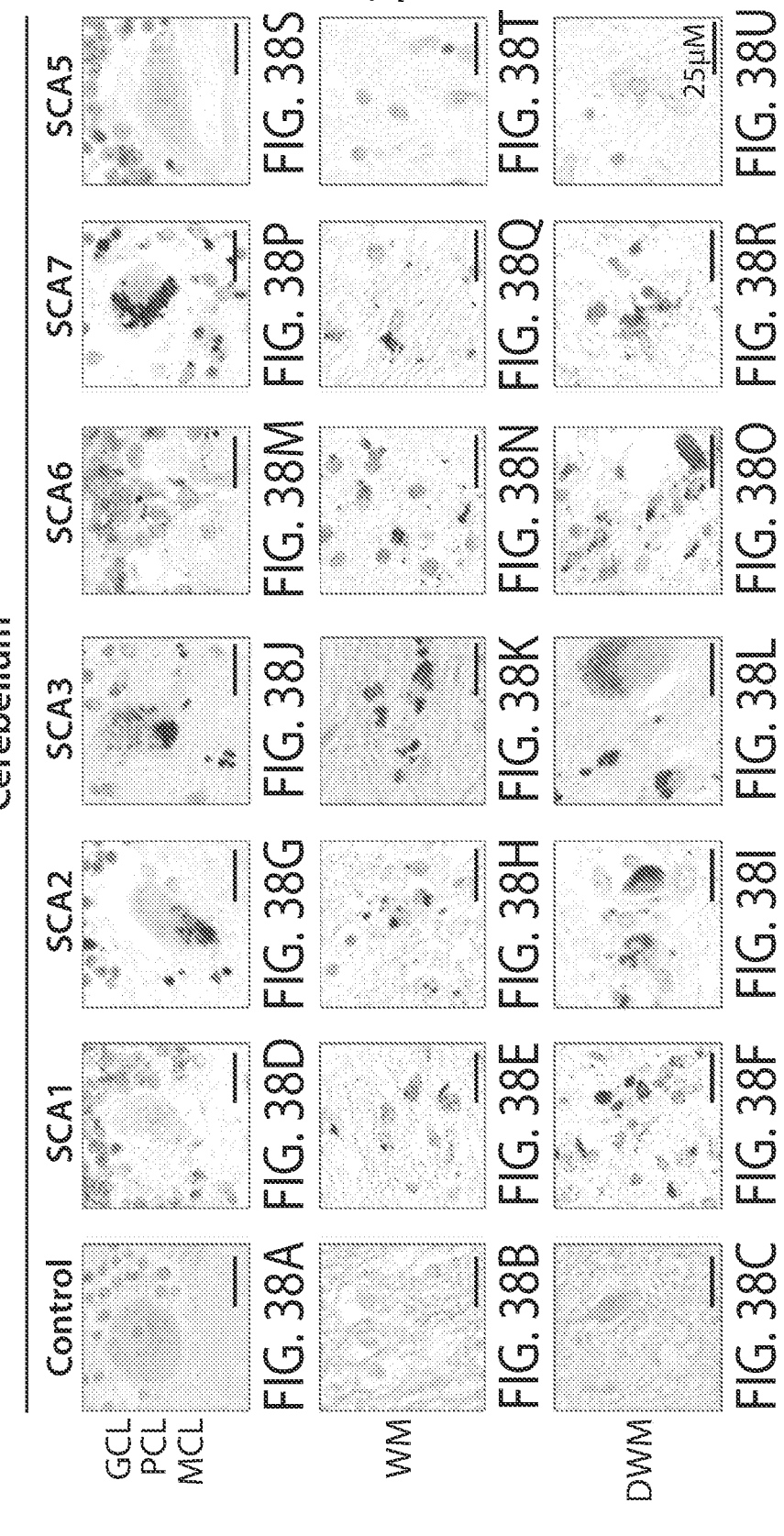
FIG. 38A  FIG. 38B  FIG. 38C  FIG. 38D  FIG. 38E  FIG. 38F  FIG. 38G  FIG. 38H  FIG. 38I  FIG. 38J  FIG. 38K  FIG. 38L  FIG. 38M  FIG. 38N  FIG. 38O  FIG. 38P  FIG. 38Q  FIG. 38R  FIG. 38S  FIG. 38T  FIG. 38U

PONS

SCA6 late stage — FIG. 44A
SCA6 presymtomatic — FIG. 44B
Control — FIG. 44C

α-polySer

α-polyLeu

70μM

RAN PROTEINS AS BIOMARKERS IN CAG/CTG EXPANSION DISORDERS

RELATED APPLICATIONS

This Application is a national stage filing under 35 U.S.C. § 371 of International Patent Application Serial No. PCT/US2020/054976, filed Oct. 9, 2020, which claims the benefit under 35 U.S.C. § 119 (e) of the filing date of U.S. provisional Application Ser. No. 62/913,662, filed Oct. 10, 2019, entitled "RAN PROTEINS AS BIOMARKERS IN CAG/CTG EXPANSION DISORDERS", the entire contents of each of which are incorporated herein by reference in their entirety.

FEDERALLY SPONSORED RESEARCH

This invention was made with government support under grant number NS040389 awarded by the National Institutes of Health. The government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Apr. 4, 2022, is named U120270072US01-SEQ-KSB and is 12,283 bytes in size.

BACKGROUND

Certain expansion mutations, such as CAG•CTG repeat expansions, have been shown to undergo a novel type of protein translation that occurs in multiple reading frames and does not require a canonical AUG initiation codon. This type of translation is called repeat associated non-ATG (RAN) translation and the proteins that are produced are called RAN proteins. There is growing evidence that RAN proteins are toxic and contribute to a growing number of diseases.

SUMMARY

Aspects of the disclosure relate to methods and kits for detecting certain RAN proteins, such as RAN proteins having a homopolymeric repeat region (e.g., a polyLeucine repeat region, a polySerine repeat region, etc.) in a sample. In some embodiments, an immunoassay is used to detect or measure levels of one or more RAN proteins in a biological sample (e.g., a serum sample) obtained from a subject.

The disclosure is based, in part, on anti-RAN protein antibodies that target (e.g., bind specifically) to homopolymeric repeat regions of certain RAN proteins, such as polyLeucine repeat RAN proteins and polySerine repeat RAN proteins. As described elsewhere herein, it was surprisingly discovered that polySerine and polyLeucine RAN proteins are translated from CAG and/or CTG repeat expansions of certain genes associated with neurodegenerative diseases, such as spinocerebellar ataxias (SCA) (e.g., SCA1, SCA2, SCA3, SCA6, SCAT, SCAB, SCA12, SCA17, etc.), Huntington's disease (HD), Huntington disease-like 2 (HDL2), Dentatorubral-pallidoluysian atrophy (DRPLA), Spinal-bulbar muscular atrophy (SBMA), Fuchs' endothelial corneal dystrophy (FBCD), and myotonic dystrophy (DM1). Thus, compositions and methods described by the disclosure are useful, in some embodiments, for diagnosing a subject as having a disease or disorder associated with CAG and/or CTG repeat expansions. In some embodiments, the compositions and methods of this disclosure may additionally or alternatively be useful for monitoring (e.g., longitudinally measuring) the levels of one or more RAN proteins (e.g., polyLeucine, polySerine, etc.) in a subject who has been or is being administered one or more therapeutic agents for the treatment of a disease or disorder associated with CAG and/or CTG repeat expansions.

In some aspects, the disclosure relates to a method for detecting one or more RAN proteins in a subject. In some embodiments, the method comprises: contacting a biological sample obtained from a subject with an anti-RAN protein antibody that targets a RAN protein homopolymeric repeat to form an anti-RAN antibody-target RAN protein complex; contacting the complex with an detectable agent to form a labeled complex; detecting the labeled complex; and identifying that the subject has a CAG and/or CTG expansion repeat-associated disease based on the presence of the labeled complex.

In some embodiments, a biological sample is a blood sample, serum sample, or a tissue sample. In some embodiments, a tissue sample is a CNS tissue sample. In some embodiments, a biological sample is a cerebrospinal fluid (CSF) sample.

In some embodiments, a subject is a mammalian subject. In some embodiments, a subject is a human or a mouse.

In some embodiments, an anti-RAN protein antibody targets (e.g., binds specifically to) a polySerine repeat region or a polyLeucine repeat region of a RAN protein. In some embodiments, an anti-RAN protein antibody is a polyclonal antibody. In some embodiments, an anti-RAN protein antibody is a monoclonal antibody. In some embodiments, an anti-RAN protein antibody does not bind to any other portion of a RAN protein (e.g., does not bind to a non-repeat, C-terminal region of a RAN protein).

In some embodiments, an expansion repeat-associated disease is a spinocerebellar ataxia (SCA) (e.g., SCA1, SCA2, SCA3, SCA6, SCAT, SCAB, SCA12, SCA17, etc.), Huntington's disease (HD), Huntington disease-like 2 (HDL2), Dentatorubral-pallidoluysian atrophy (DRPLA), Spinal-bulbar muscular atrophy (SBMA), Fuchs' endothelial corneal dystrophy (FECD), or myotonic dystrophy (DM1).

In some embodiments, a detectable agent is an antibody, a fluorophore, a chemiluminescent agent, or an electrochemiluminescent agent. In some embodiments, detecting comprises performing an immunoassay, for example an immunohistochemistry assay, an immunofluorescence assay, an electrochemiluminescent assay, or a Western blot. In some embodiments, an electrochemiluminescent assay is a Meso Scale Detection (MSD) assay.

In some embodiments, a method further comprises a step of administering a therapeutic agent to the subject. In some embodiments, a therapeutic agent is a small molecule, an antibody, a peptide, or an inhibitory nucleic acid. In some embodiments, a therapeutic antibody is an anti-RAN protein antibody.

In some embodiments, a method further comprises a step of obtaining a second biological sample from the subject after administration of a therapeutic agent and detecting one or more RAN proteins in the second biological sample.

In some aspects, the disclosure relates to a method for measuring pharmacokinetic changes in RAN protein levels in a subject. In some embodiments, the method comprises: detecting in a first biological sample obtained from a subject one or more RAN proteins using an immunoassay comprising an anti-RAN protein antibody that targets a RAN protein homopolymeric repeat; detecting in a second biological sample obtained from the subject one or more RAN proteins using an immunoassay comprising an anti-RAN protein antibody that targets a RAN protein homopolymeric repeat, wherein the second biological sample is obtained after administration of a therapeutic agent to the subject; and determining that administration of the therapeutic agent to the subject results in a change in one or more RAN protein levels in the subject if the amount of RAN proteins detected in the second biological sample is different than the amount of RAN proteins detected in the first biological sample.

In some embodiments, administration of the therapeutic agent to the subject results in a change in one or more RAN protein levels in the subject if the amount of RAN proteins detected in the second biological sample is more than the amount of RAN proteins detected in the first biological sample. In some embodiments, if the amount of RAN proteins detected in the second biological sample is more than the amount of RAN proteins detected in the first biological sample, administration of the therapeutic agent is stopped.

In some embodiments, administration of the therapeutic agent to the subject results in a change in one or more RAN protein levels in the subject if the amount of RAN proteins detected in the second biological sample is less than the amount of RAN proteins detected in the first biological sample. In some embodiments, if the amount of RAN proteins detected in the second biological sample is less than the amount of RAN proteins detected in the first biological sample, administration of the therapeutic agent is continued.

In some embodiments, a first and/or a second biological sample is a blood sample, a serum sample, or a tissue sample. In some embodiments, a tissue sample is a CNS tissue sample. In some embodiments, a first and/or a second biological sample is a cerebrospinal fluid (CSF) sample.

In some embodiments, an anti-RAN protein antibody targets (e.g., binds specifically to) a polySerine repeat region or a polyLeucine repeat region. In some embodiments, an anti-RAN protein antibody is a polyclonal antibody. In some embodiments, an anti-RAN protein antibody is a monoclonal antibody.

In some embodiments, a subject is characterized as having a CAG and/or a CTG expansion repeat disease. In some embodiments, the expansion repeat-associated disease selected from a spinocerebellar ataxia (SCA) (e.g., SCA1, SCA2, SCA3, SCA6, SCAT, SCAB, SCA12, SCA17, etc.), Huntington's disease (HD), Huntington disease-like 2 (HDL2), Dentatorubral-pallidoluysian atrophy (DRPLA), Spinal-bulbar muscular atrophy (SBMA), Fuchs' endothelial corneal dystrophy (FECD), and myotonic dystrophy (DM1). In some embodiments, a subject is a mammal. In some embodiments, a subject is a human or a mouse.

In some aspects, the disclosure relates to a kit comprising one or more anti-RAN protein antibodies that target a polySerine or polyLeucine repeat region of a RAN protein; and an immunoassay plate and/or reagents. In some embodiments, the kit further comprises a control sample. In some embodiments, the control sample comprises one or more RAN proteins. In some embodiments, the control sample does not comprise one or more RAN proteins. In some embodiments, an immunoassay plate and/or reagents is a MSD assay plate and/or MSD assay reagents.

In some aspects, the disclosure provides methods of producing anti-RAN protein antibodies. Methods of producing an antibody as described herein typically comprise administering to a cell or a subject one or more RAN protein peptide antigens. Thus, in some aspects, the disclosure provides a method of producing an antibody, the method comprising administering to a cell or a subject a peptide antigen comprising the sequence set forth in any one of SEQ ID NOs: 17-26. In some embodiments, the antibody specifically binds to a poly-(Ser) RAN protein or a poly-(Leu) RAN protein. In some embodiments, the method of producing an antibody further comprises the step of isolating the antibody from the subject. In some embodiments, the subject is a mammalian cell. In some embodiments, the mammalian cell is a B cell. In some embodiments, the subject is mammal, optionally wherein the mammal is a human, goat, rabbit, guinea pig, or mouse.

BRIEF DESCRIPTION OF DRAWINGS

FIG. 2 shows a schematic describing a strategy for production of novel RAN protein repeat-region targeting antibodies, and associated advantages. (From top to bottom SEQ ID NOS: 5-10).

FIG. 3 shows a schematic depicting CAG•CTG expansion disorders.

FIG. 8 shows representative data indicating that anti-POLYSER antibody detects RAN positive cells in patient-derived SCA1 tissue. (SEQ ID NO: 11).

FIG. 13 shows representative data indicating anti-POLYSER immunopositive cells in patient-derived SCA3 tissue. (SEQ ID NO: 13).

FIG. 16 shows representative data indicating that anti-POLYSER antibody detects RAN positive cells in patient-derived SCA6 tissue. (SEQ ID NO: 14).

FIG. 21 shows representative data indicating that anti-POLYSER antibody detects RAN positive cells in patient-derived HDL2 striatum. (SEQ ID NO: 16).

FIG. 33 shows a summary of immunostaining data described in the Example.

Figure 34:
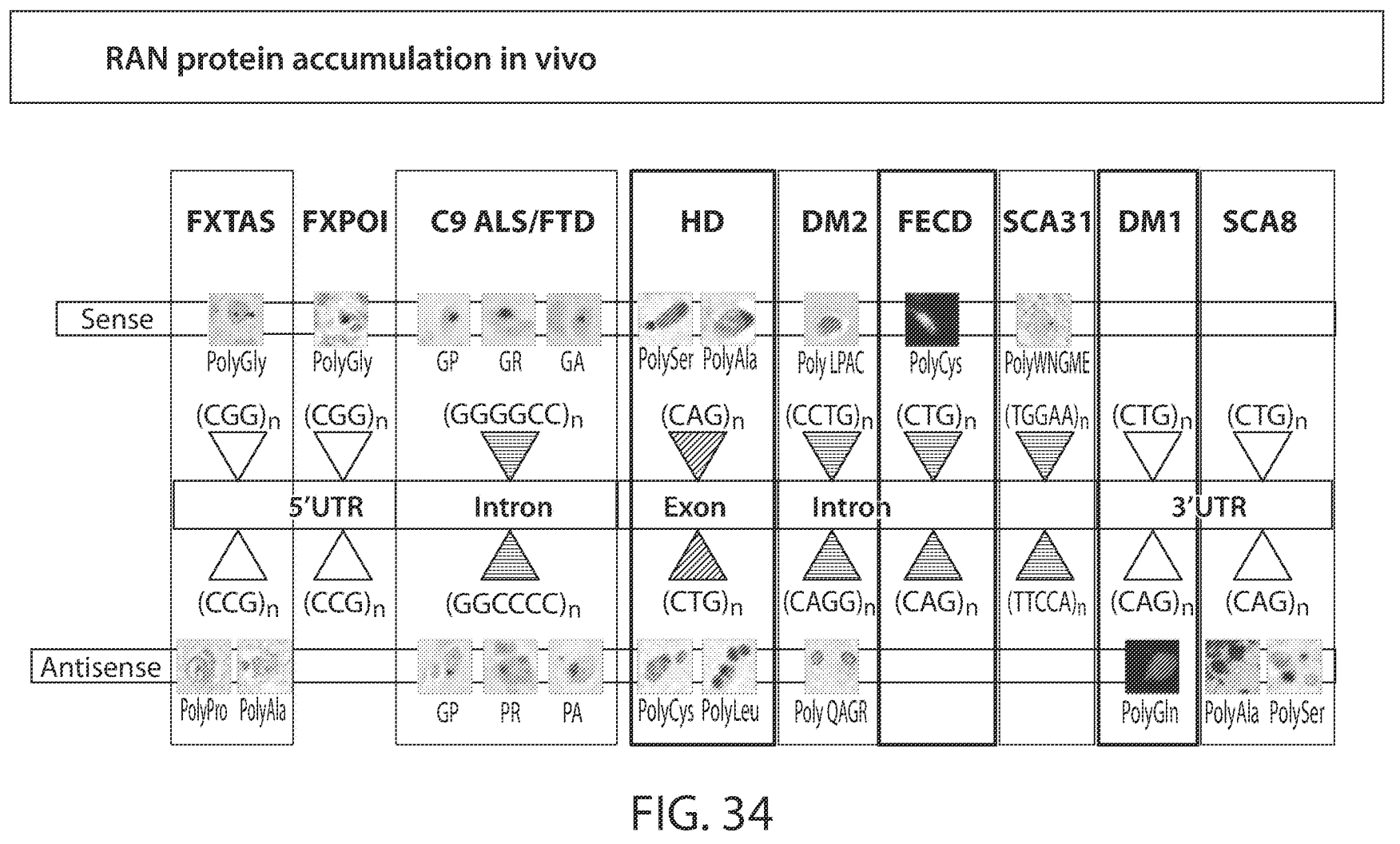

FIG. 34 shows a schematic depicting RAN protein accumulation in vivo.

FIGS. 35A and 35B show the immunofluorescence of transfected cells, which demonstrates co-localization of α-Flag (circled) and newly developed repeat antibodies: α-polySer (FIG. 35A) and α-polyLeu (FIG. 35B), shown with arrows. No signal was detected in cells transfected with an empty vector (middle row, FIGS. 35A and 35B) or when pre-immune sera were used as the primary antibody (bottom row, FIGS. 35A and 35B). FIGS. 35C and 35D show immunohistochemical experiments on HD frontal cortex, which validate the specificity of the newly generated repeat antibodies by comparing their signal with those obtained using the previously validated HD polySer and HD polyLeu C-terminal antibodies. Signal (arrows) was specifically detected in the HD samples (top row, FIGS. 35C and 35D), but not on the control samples (bottom row, FIGS. 35C and 35D).

FIG. 36 shows RAN-polySer staining in SCA1, SCA2, SCA3, SCA6, SCA7, and SCA5 (negative control) human cerebellum. Immunohistochemistry shows polySer accumulation across the cerebellum. Positive regions include Bergmann glia, white matter (WM), and deep white matter (DWM) regions around the dentate nucleus. No signal was detected in non-affected or SCA5 negative controls. *arrows (→)=positive staining, arrows (→)=nuclear counterstain.

FIGS. 38A-38U show RAN PolyLeu accumulation in SCA1, SCA2, SCA3, SCA6, SCA7, and SCA5 (negative control) cerebellum. Immunostaining using an antibody against the polyLeu repeat motif shows frequent polyLeu aggregates. PolyLeu positive regions include Purkinje cells and Bergman glia (FIGS. 38D, 38G, 38J, 38M, 38P), cortical white matter (FIGS. 38E, 38H, 38K, 38N, 38Q), and neurons and glial cells around the dentate nucleus (FIGS. 38F, 38I, 38L, 38O, 38R). PolyLeu accumulation is more prominent in white matter regions. PolyLeu aggregates can be nuclear, cytoplasmic, or in the neuropil. Negative controls include healthy (FIGS. 38A-38C) and SCA5 (FIGS. 38S-38U) cases.

FIG. 40A (SEQ ID NO: 17); FIG. 40B (SEQ ID NO: 18); FIG. 40C (SEQ ID NO: 19); FIG. 40D (SEQ ID NO: 20); FIG. 40E (SEQ ID NO: 21); FIG. 40F (SEQ ID NO: 22); FIG. 40G (SEQ ID NO: 23); FIG. 40H (SEQ ID NO: 24); FIG.

40I (SEQ ID NO: 25); and FIG. 40J (SEQ ID NO: 26) Immunohistochemistry using C-terminal antibodies demonstrates similar signal and RAN protein accumulation patterns as detected in immunohistochemical experiments that used the repeat antibodies.

FIGS. 41C and 41D show that PolySer is not detected on the pcp2-Atxn1 82Q mice, which specifically express the transgene in Purkinje cells, while polyGln detection in these cells is quite robust. FIGS. 41E and 41F show that polySer positive cells are detected in the cortex of HD knock-in mice. Immunohistochemistry on allelic series shows that polySer accumulation is more pronounced at longer CAG repeats (FIG. 41E) and increases with mouse age (FIG. 41F). Antisense RAN polyLeu aggregates are detected in SCA3 (FIG. 41G) and HD mice (FIG. 41H)

FIGS. 42A-42Y show that polySer and polyLeu RAN proteins accumulate in regions showing markers of pathology. Immunohistochemistry of serial sections shows that white matter regions with abundant RAN protein accumulation have increased microglial proliferation (ramified) and activation (ameboid), as indicated with Iba1 staining (FIGS. 42V-42Y). Regions with polySer and polyLeu RAN prominent accumulation display white matter integrity loss, as indicated with luxol fast blue staining (LFB) (FIGS. 42Q-42T). PolyGln aggregates are rare (1C2 staining; FIGS. 42B-42E)). FIGS. 42A-42E show IC2 staining of control (FIG. 42A), SCA1 (FIG. 42B), SCA2 (FIG. 42C), SCA3 (FIG. 42D), and SCA7 (FIG. 42E) tissue. FIGS. 42F-42J show polySer staining of control (FIG. 42F), SCA1 (FIG. 42G), SCA2 (FIG. 42H), SCA3 (FIG. 42I), and SCA7 (FIG. 42J). FIGS. 42K-42O show polyLeu staining of control (FIG. 42K), SCA1 (FIG. 42L), SCA2 (FIG. 42M), SCA3 (FIG. 42N), and SCA7 (FIG. 42O). FIGS. 42P-42T show LFB staining of control (FIG. 42P), SCA1 (FIG. 42Q), SCA2 (FIG. 42R), SCA3 (FIG. 42S), and SCA7 (FIG. 42T). FIGS. 42U-42Y show Iba1 staining of control (FIG. 42U), SCA1 (FIG. 42V), SCA2 (FIG. 42W), SCA3 (FIG. 42X), and SCA7 (FIG. 42Y).

FIGS. 43A-43Y show that polySer and polyLeu RAN proteins accumulate in regions showing markers of pathology. Images show low magnification fields showing the frequency of RAN polySer and RAN polyLeu aggregates, microglial positive cells, the extent of white matter damage, and the low abundance of polyGln aggregates. FIGS. 43A-43E show IC2 staining of control (FIG. 43A), SCA1 (FIG. 43B), SCA2 (FIG. 43C), SCA3 (FIG. 43D), and SCA7 (FIG. 43E) tissue. FIGS. 43F-43J show polySer staining of control (FIG. 43F), SCA1 (FIG. 43G), SCA2 (FIG. 43H), SCA3 (FIG. 43I), and SCA7 (FIG. 43J). FIGS. 43K-43O show polyLeu staining of control (FIG. 43K), SCA1 (FIG. 43L), SCA2 (FIG. 43M), SCA3 (FIG. 43N), and SCA7 (FIG. 43O). FIGS. 43P-43T show LFB staining of control (FIG. 43P), SCA1 (FIG. 43Q), SCA2 (FIG. 43R), SCA3 (FIG. 43S), and SCA7 (FIG. 43T). FIGS. 43U-43Y show Iba1 staining of control (FIG. 43U), SCA1 (FIG. 43V), SCA2 (FIG. 43W), SCA3 (FIG. 43X), and SCA7 (FIG. 43Y).

FIGS. 44A-44F show that polySer and polyLeu aggregates increase with disease progression Immunostaining of SCA6 human pons shows aggregates of RAN polySer and polyLeu proteins around pons white matter tracts (FIGS. 44A, 44B, 44D, and 44E). PolySer and polyLeu aggregates are variable in size and are frequently found in postmortem cases of late stage disease (FIGS. 44A and 44D). In contrast, postmortem cases with documented early death prior to disease show rare, smaller aggregates (FIGS. 44B and 44E). Healthy controls did not show any signal (FIGS. 44C and 44F).

DETAILED DESCRIPTION

Figure 1:
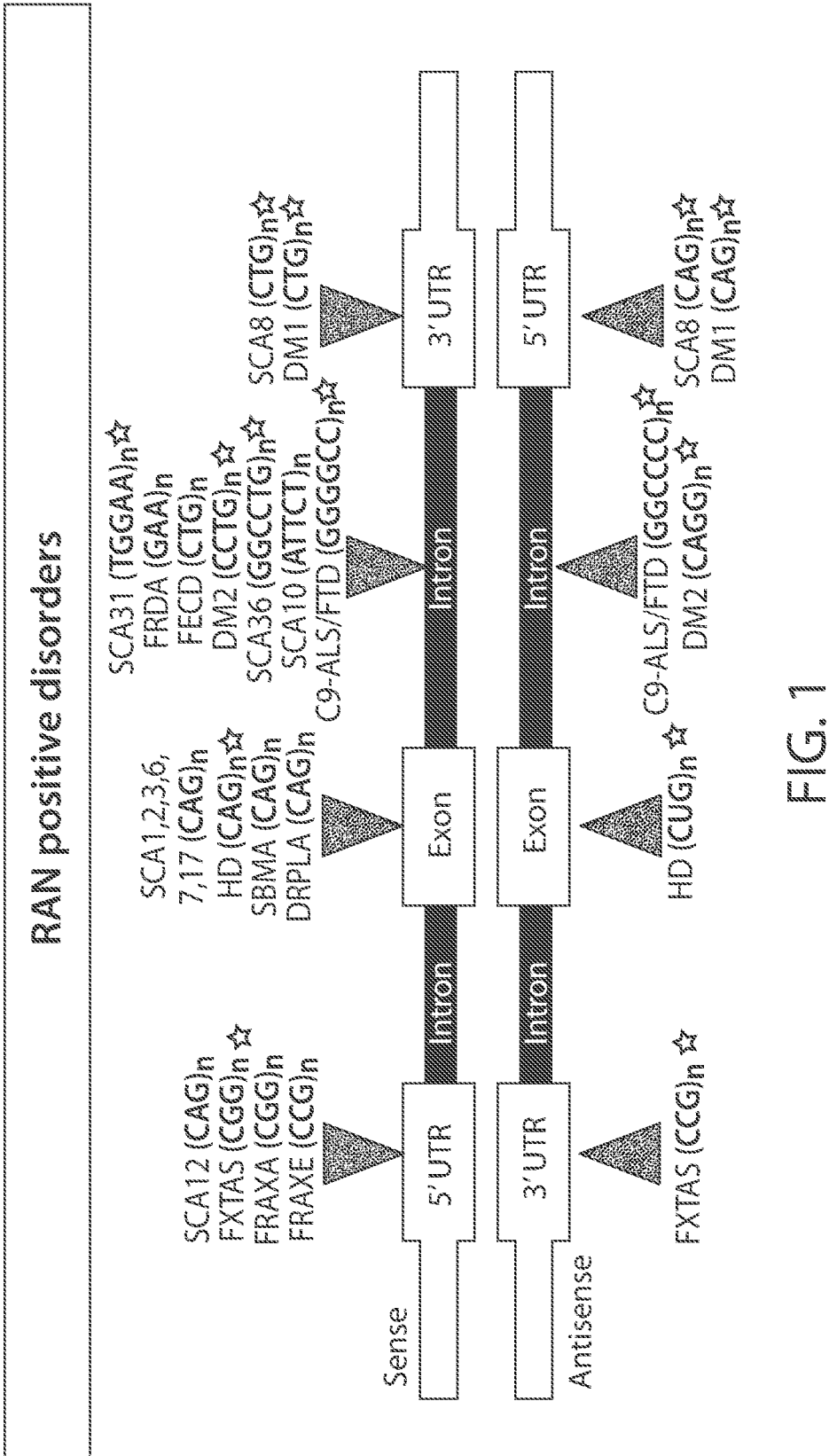
FIG. 1 shows a schematic depicting expansion repeat-associated disorders characterized by RAN protein expression.
Figure 4:
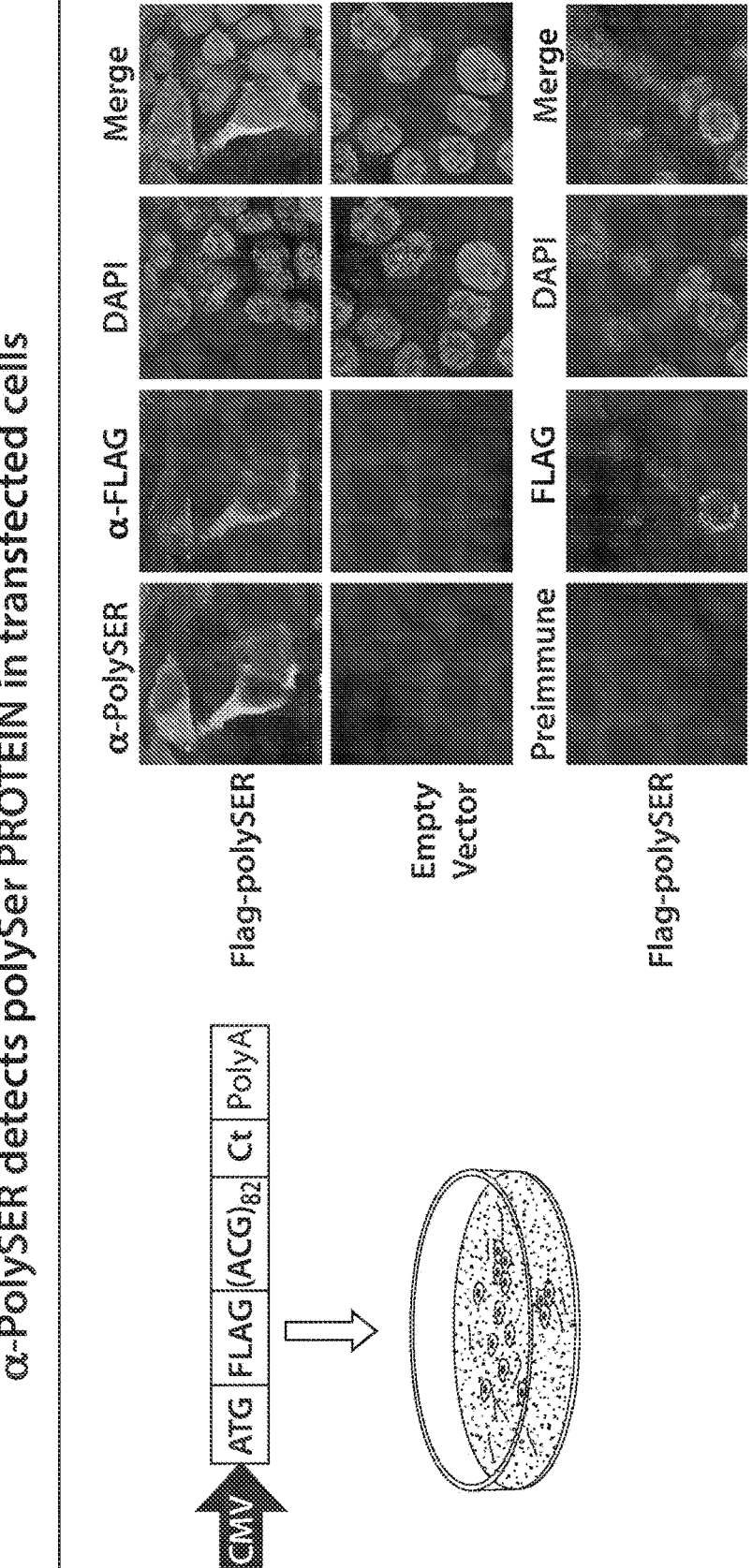
FIG. 4 shows representative data indicating that anti-POLYSER antibody, which targets the homopolymeric serine repeat of RAN proteins, detects polySerine RAN proteins in transfected cells.
Figure 5:
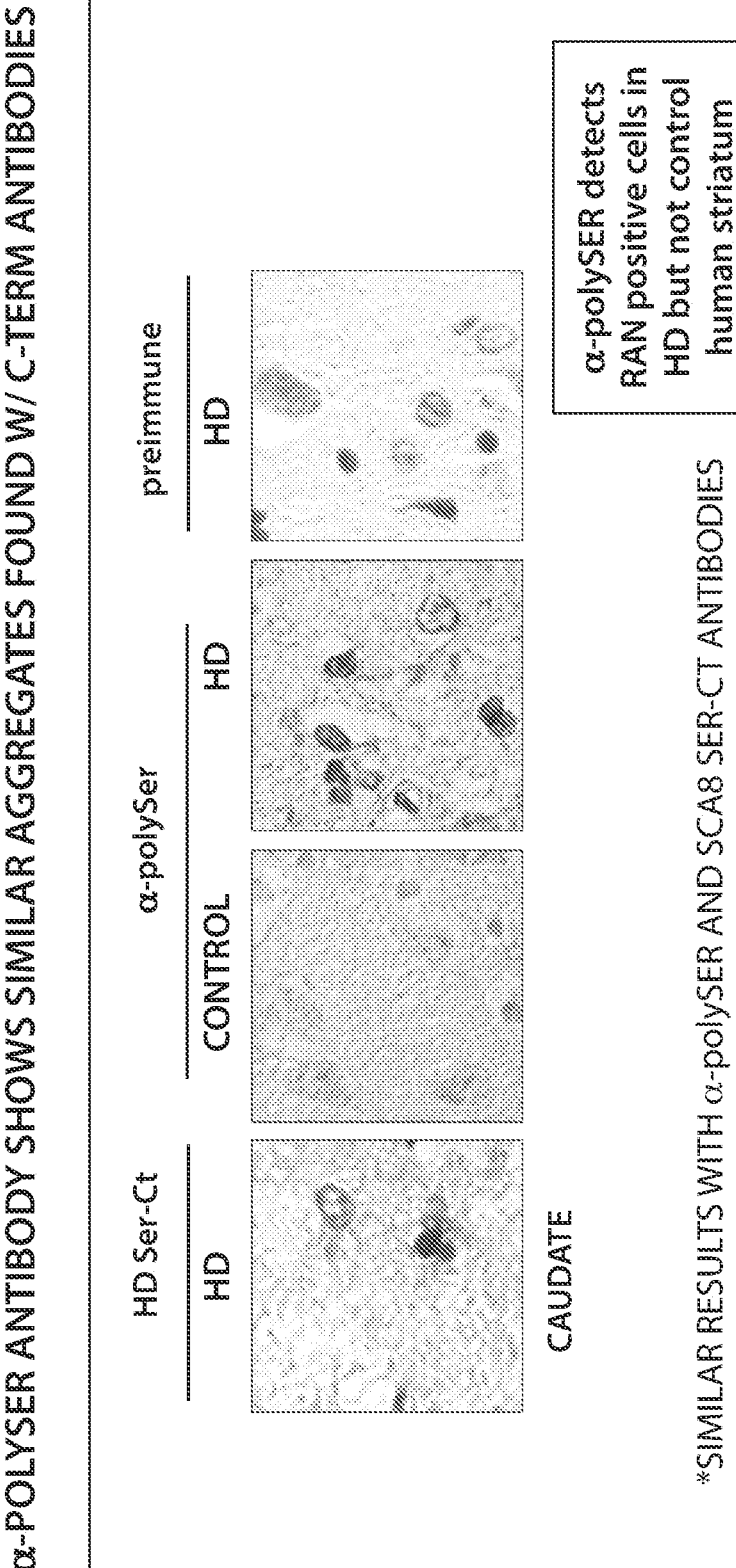
FIG. 5 shows representative data indicating that anti-POLYSER antibody, which targets a homopolymeric serine repeat, detects polySerine RAN proteins in patient-derived Huntington's disease tissue in a similar manner to anti-polySer antibodies that target unique C-terminal regions of polySerine RAN proteins. Neither antibody detected RAN positive cells in control human striatum.
Figure 6:
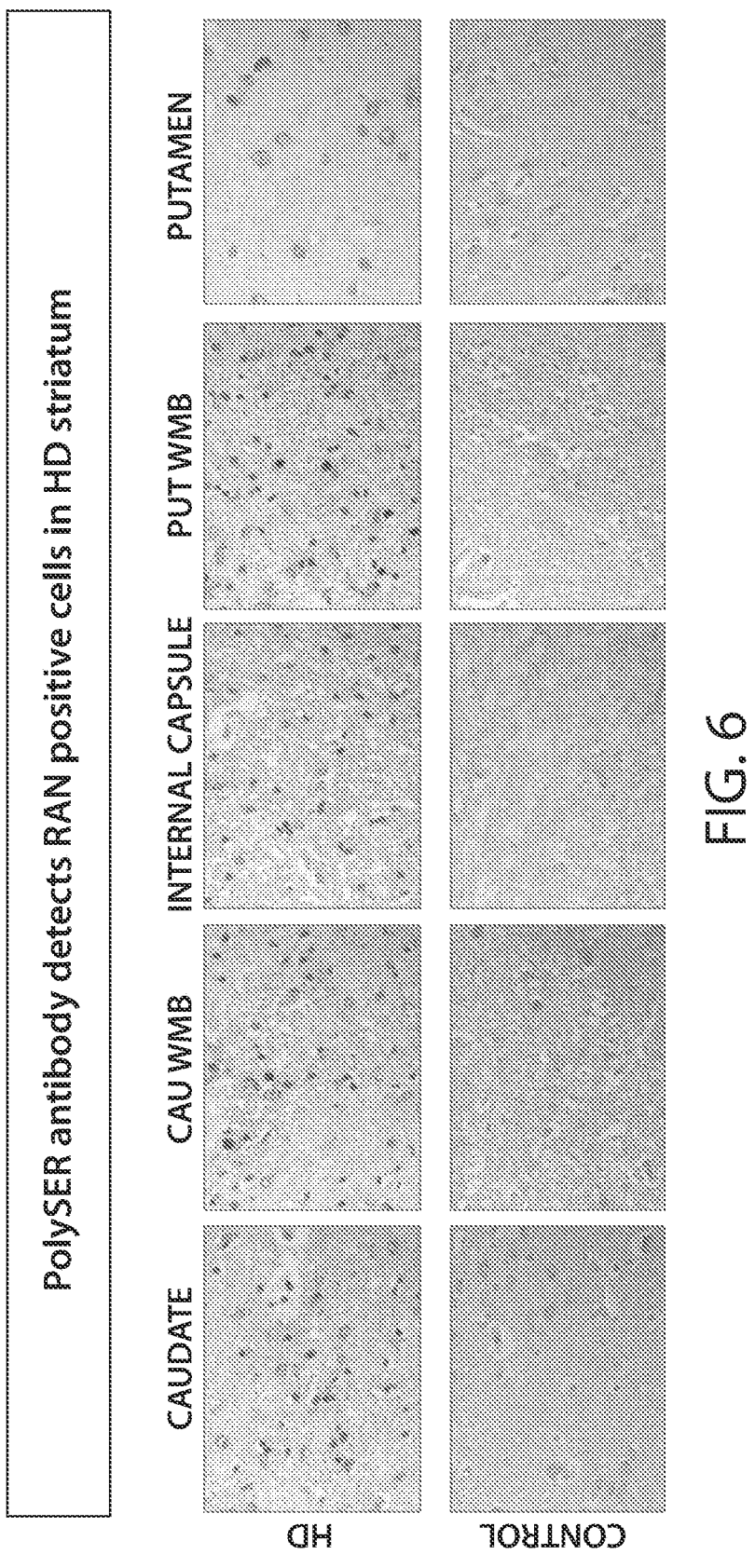
FIG. 6 shows representative data indicating that anti-POLYSER antibody detects RAN positive cells in patient-derived HD striatum.
Figure 7:
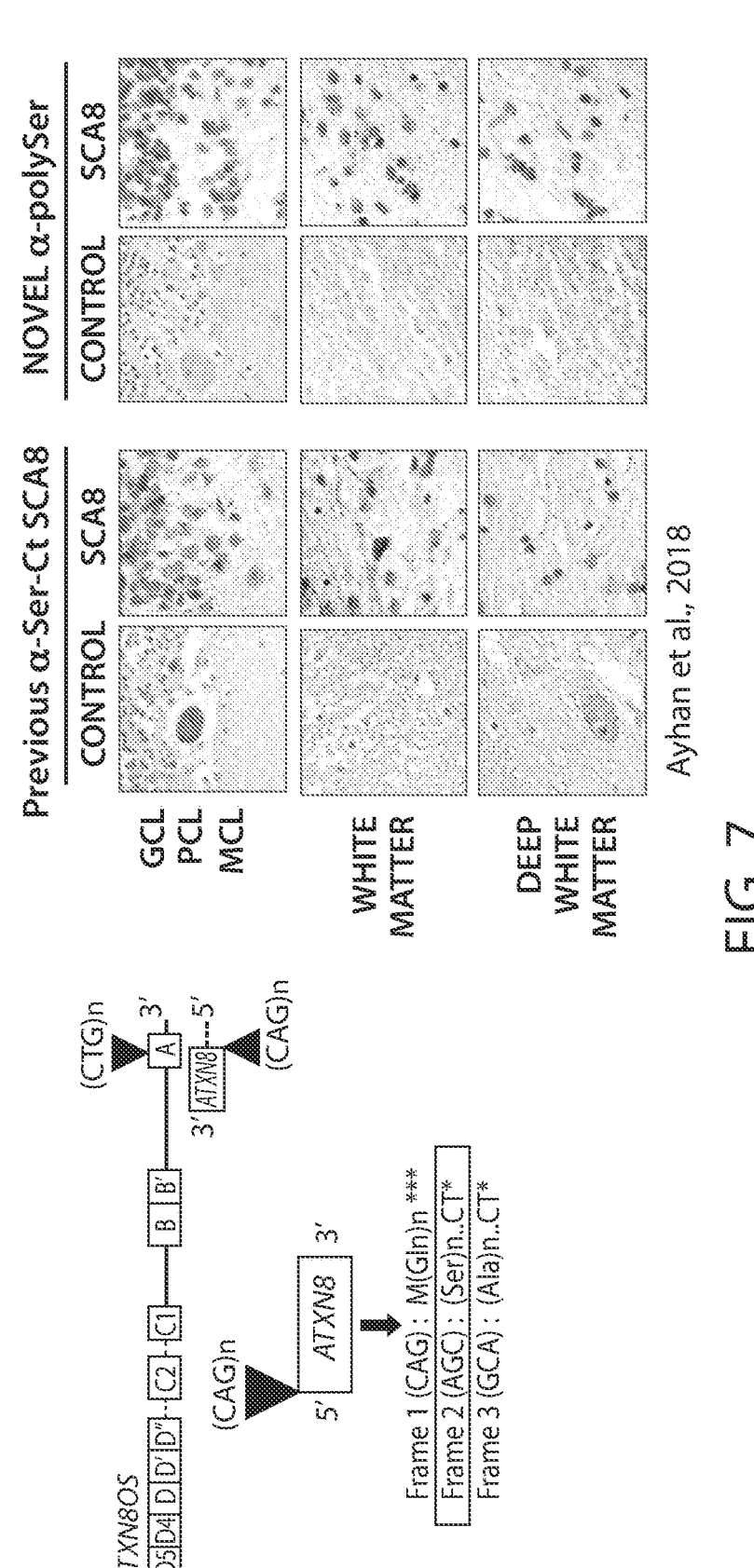
FIG. 7 shows representative data indicating that anti-POLYSER antibody detects RAN positive cells in patient-derived SCA8 cerebellum.
Figure 9:
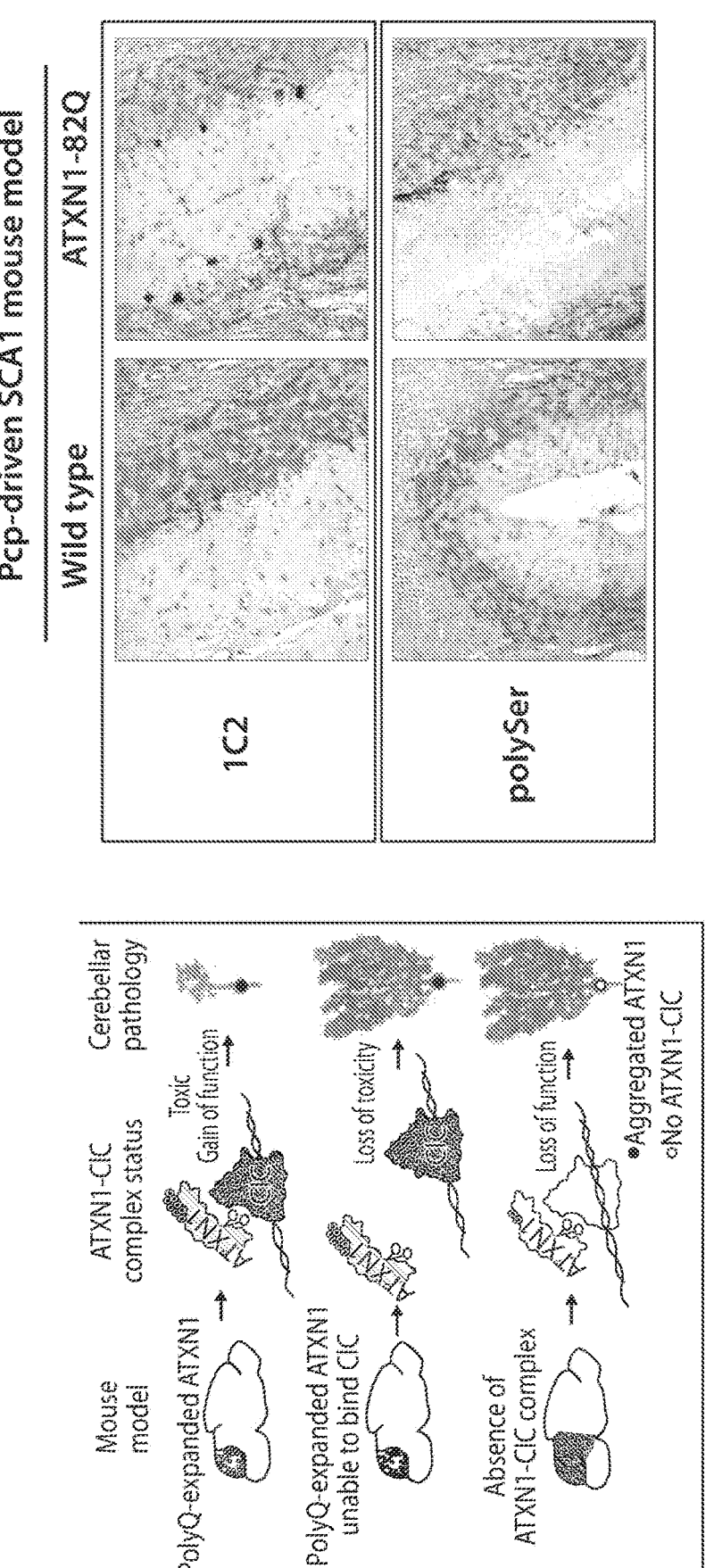
FIG. 9 shows representative data indicating that polySer RAN proteins do not accumulate in Prp-ATXN1 82Q mice.
Figure 10:
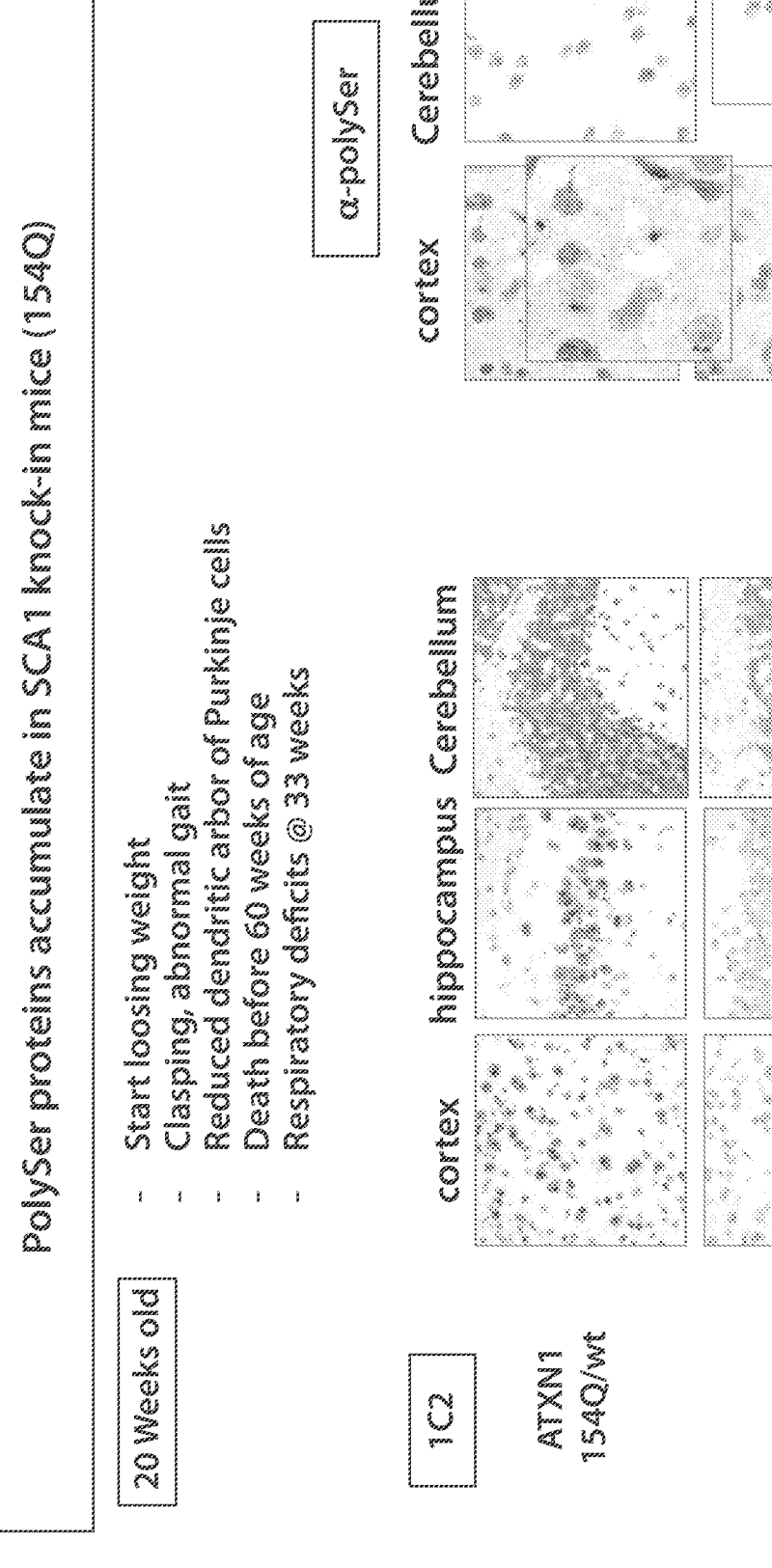
FIG. 10 shows representative data indicating that polySer RAN proteins accumulate in SCA1 knock-in mice (154Q), as detected by anti-POLYSER antibody.
Figure 11:
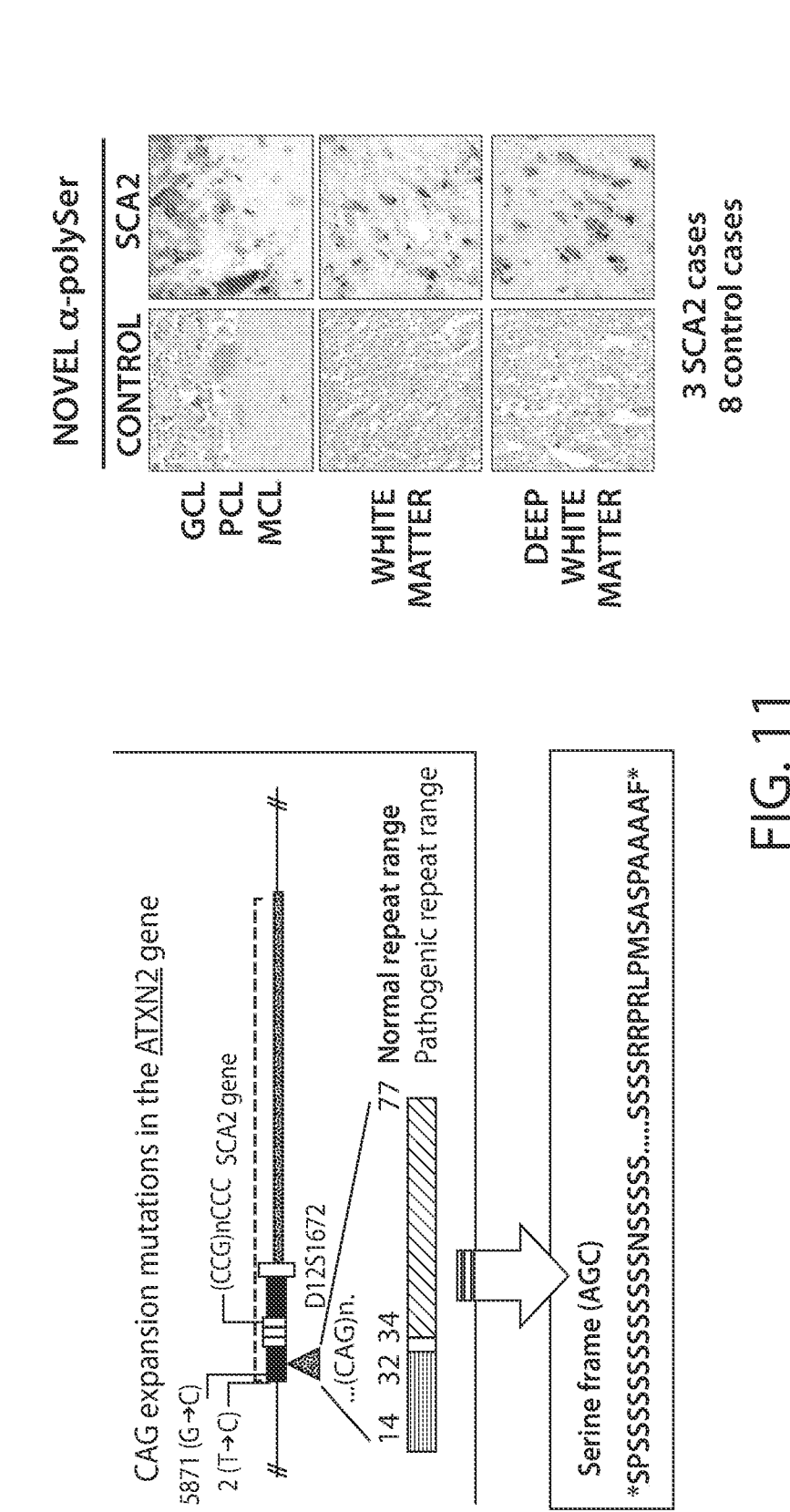
FIG. 11 shows representative data indicating that polySer RAN proteins accumulate in patient-derived SCA2 tissue, as detected by anti-POLYSER antibody. (SEQ ID NO: 12).
Figure 12:
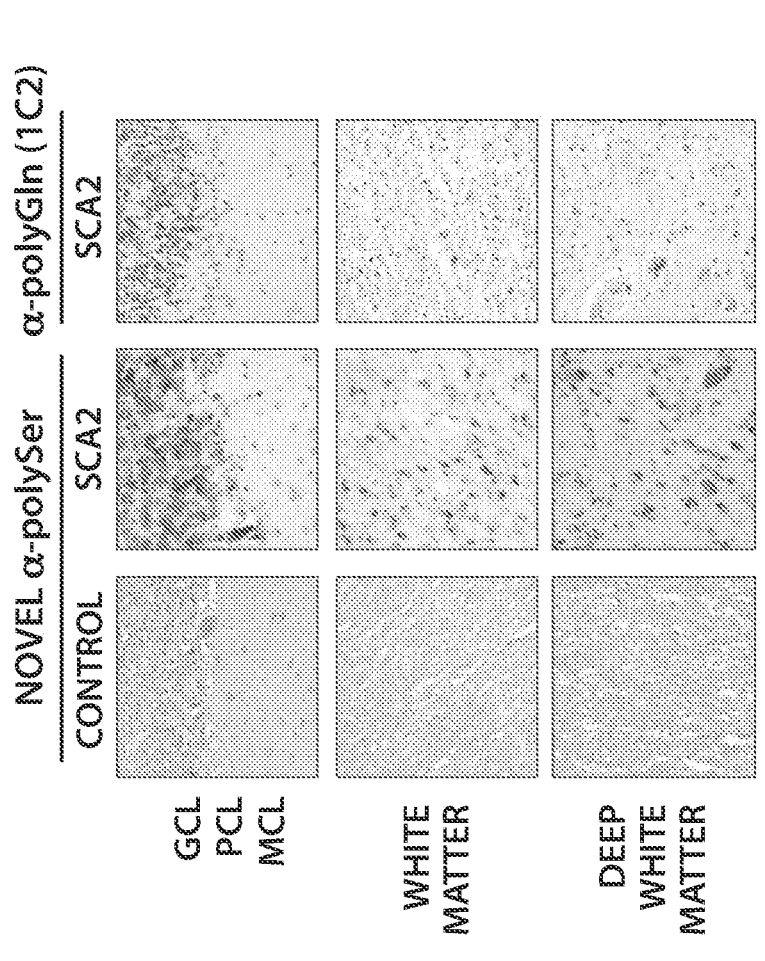
FIG. 12 shows representative data indicating that anti-POLYSER antibody and anti-polyGln antibodies show different distribution patterns in SCA2 tissue.
Figure 14:
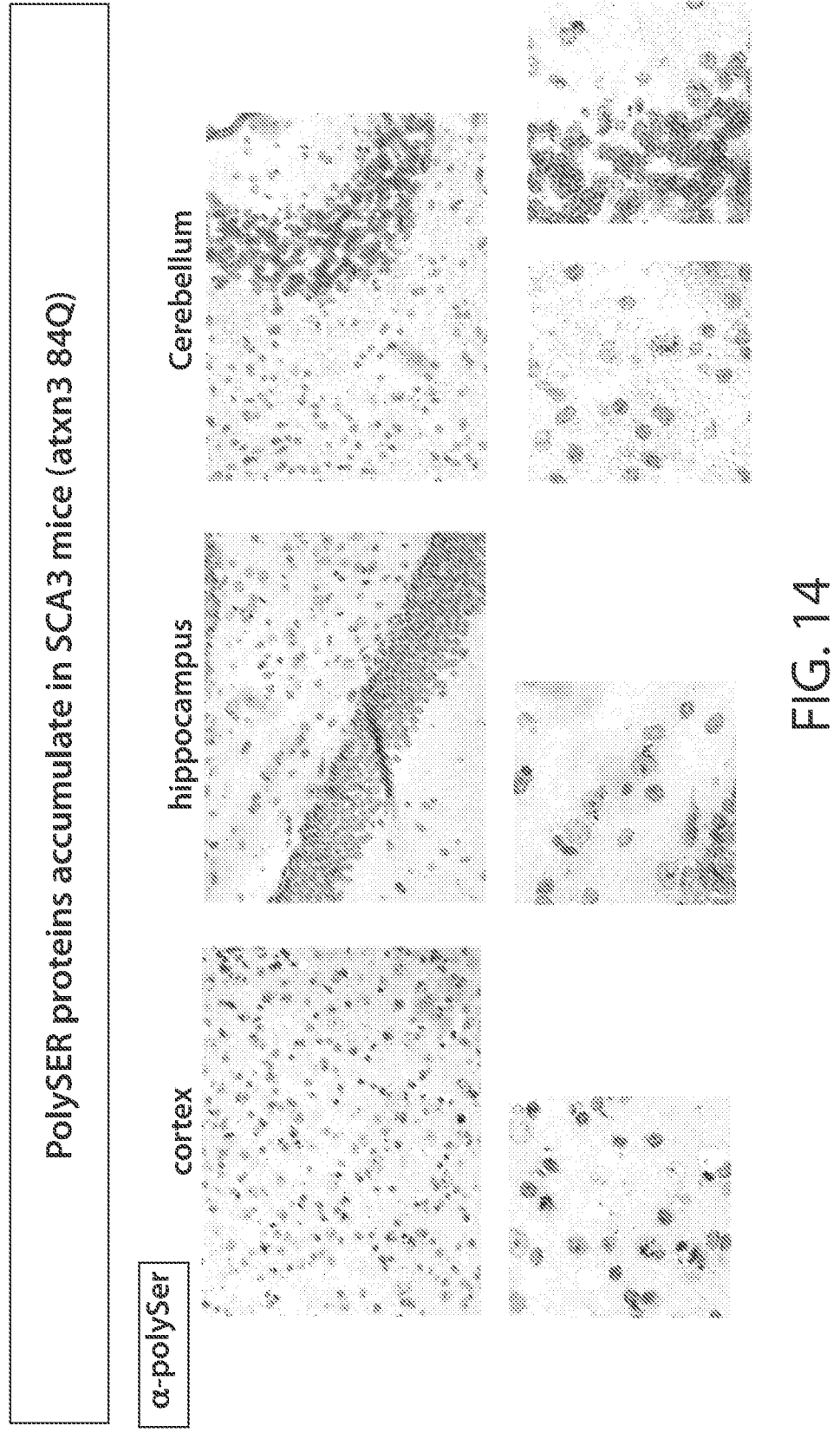
FIG. 14 shows representative data indicating that polySer RAN proteins accumulate in SCA3 mouse tissue (atxn3 84Q), as detected by anti-POLYSER antibody.
Figure 15:
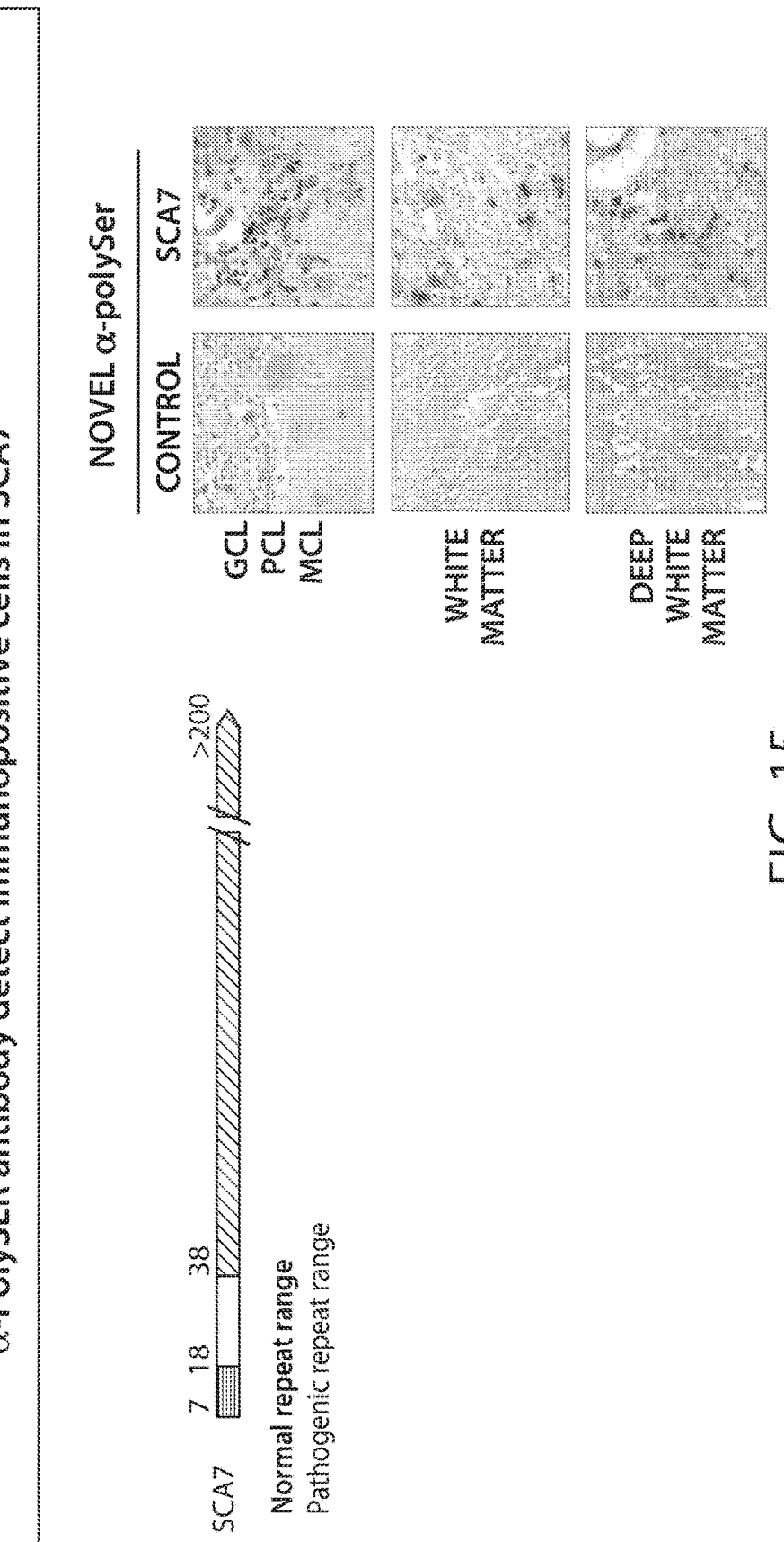
FIG. 15 shows representative data indicating that anti-POLYSER antibody detects RAN positive cells in patient-derived SCA7 tissue.
Figure 17:
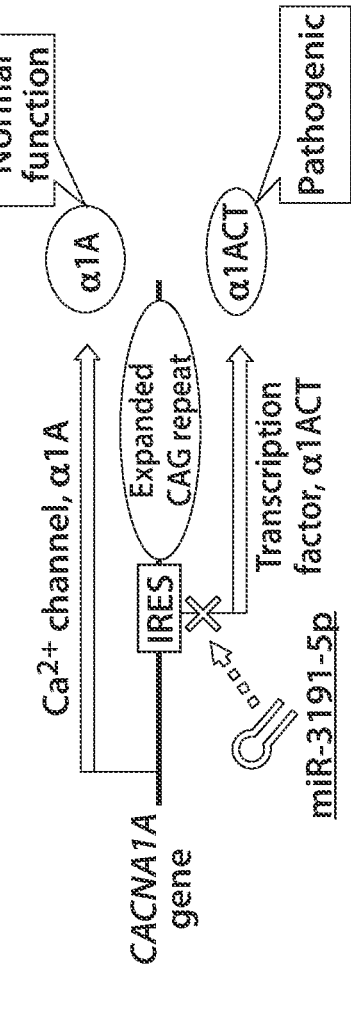
FIG. 17 shows a schematic indicating that anti-1-ACT is translated by an IRES-dependent mechanism and contains the CAG repeat expansion. (SEQ ID NO: 15).
Figure 18:
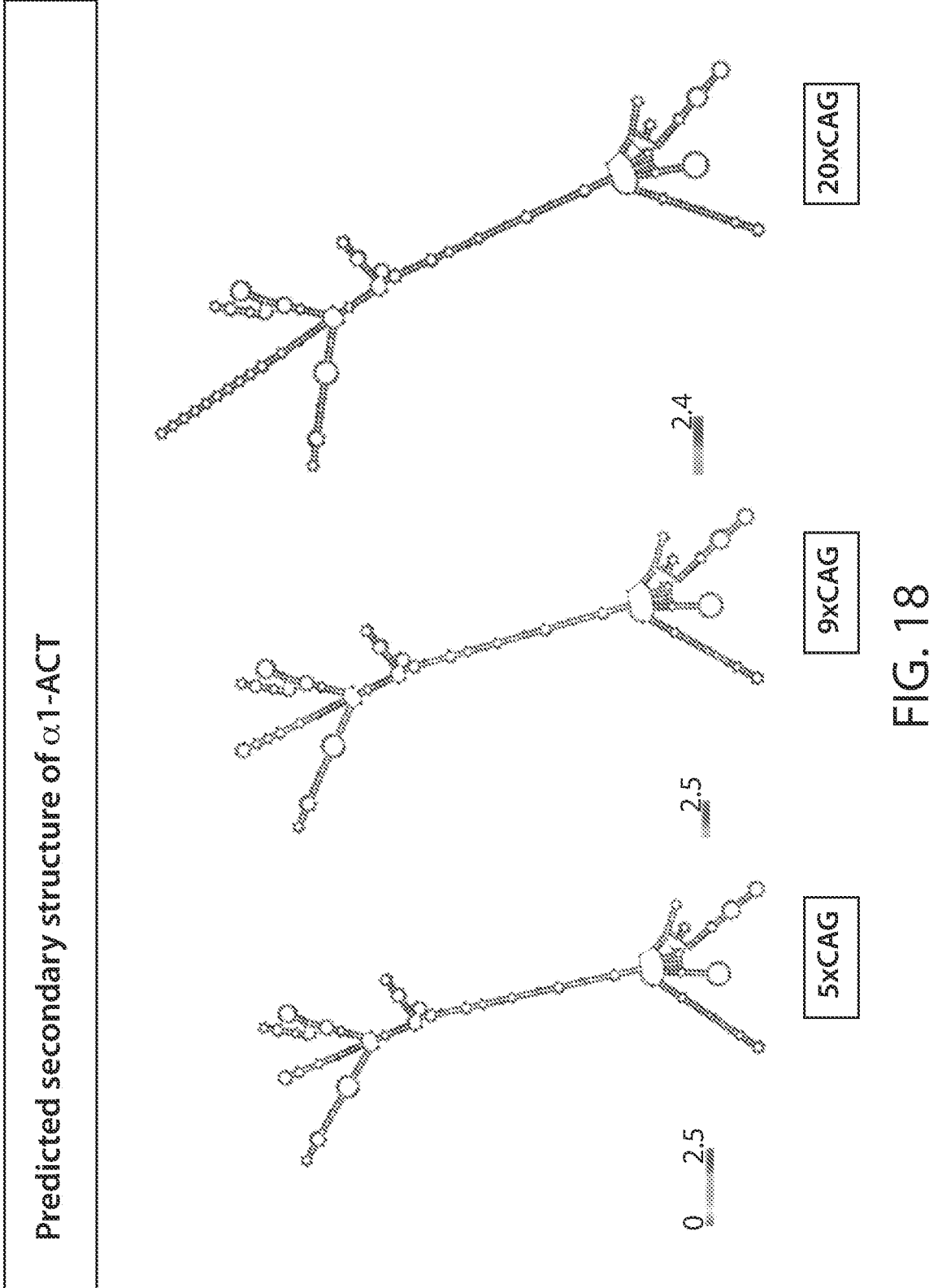
FIG. 18 shows the predicted secondary structure of anti-1-ACT carrying different repeat expansions.
Figure 19:
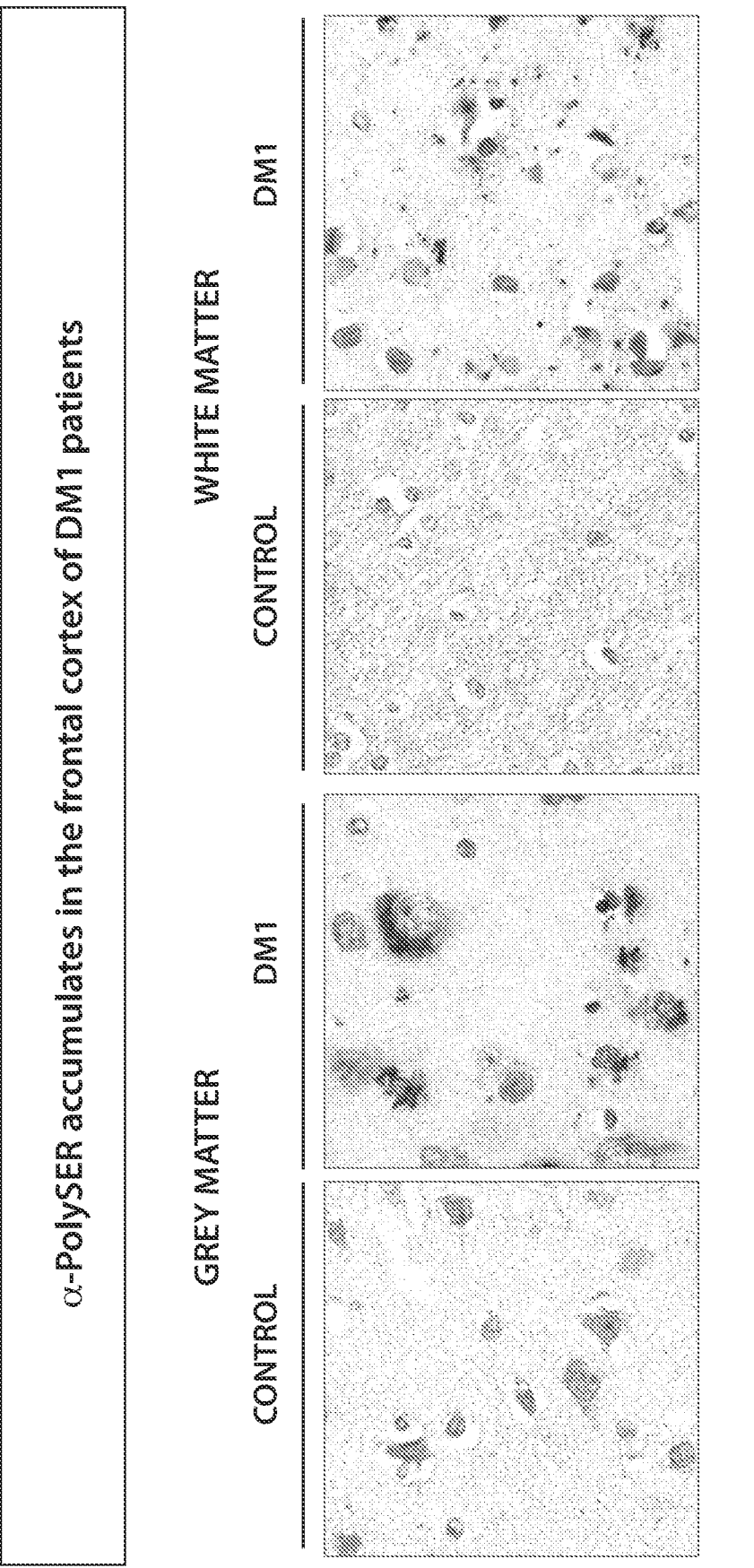
FIG. 19 shows representative data indicating that polySer RAN proteins accumulate in the frontal cortex of DM1 patients.
Figure 20:
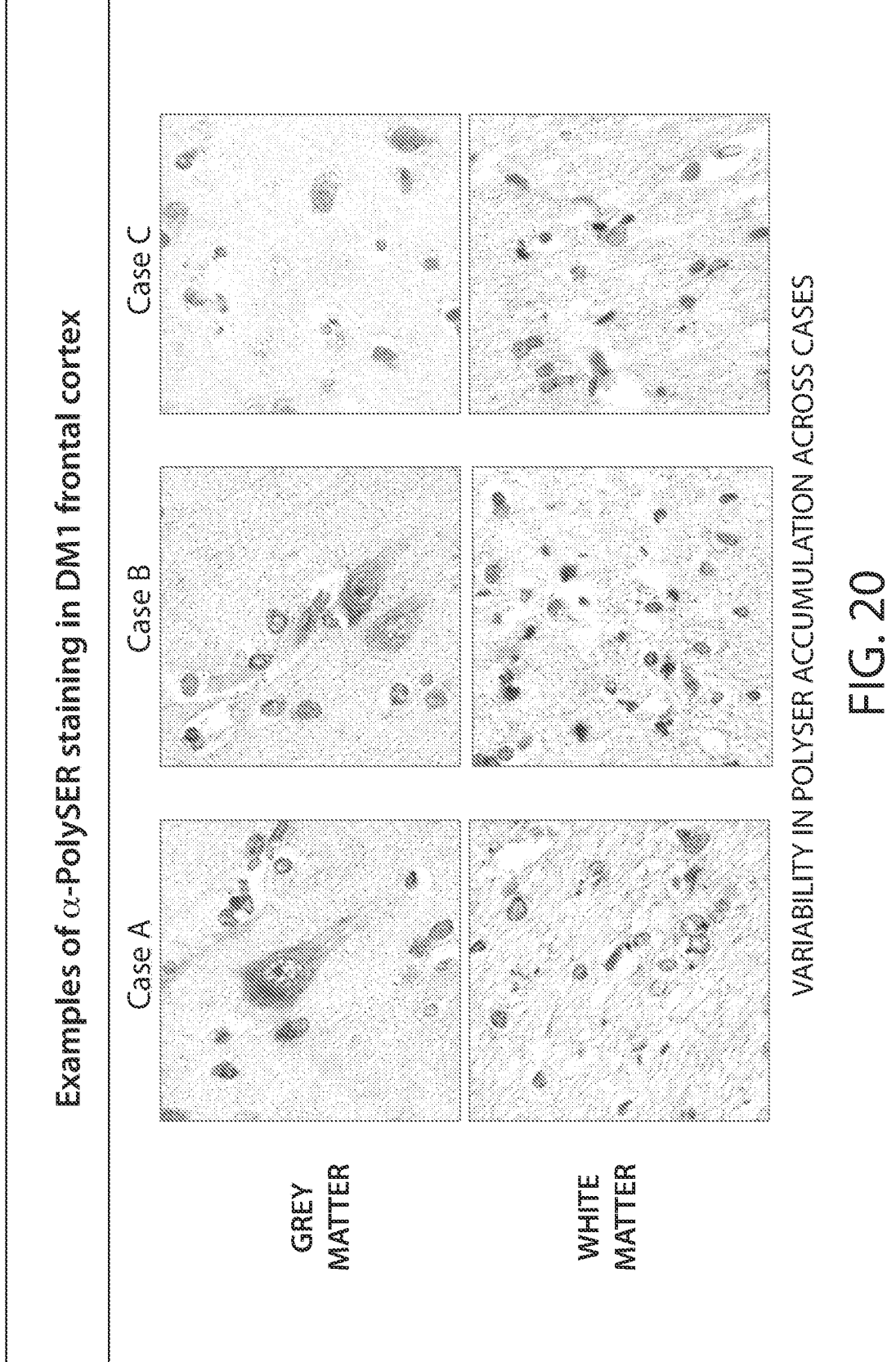
FIG. 20 shows representative data indicating that polySer RAN proteins accumulate in the frontal cortex of DM1 patients.
Figure 22:
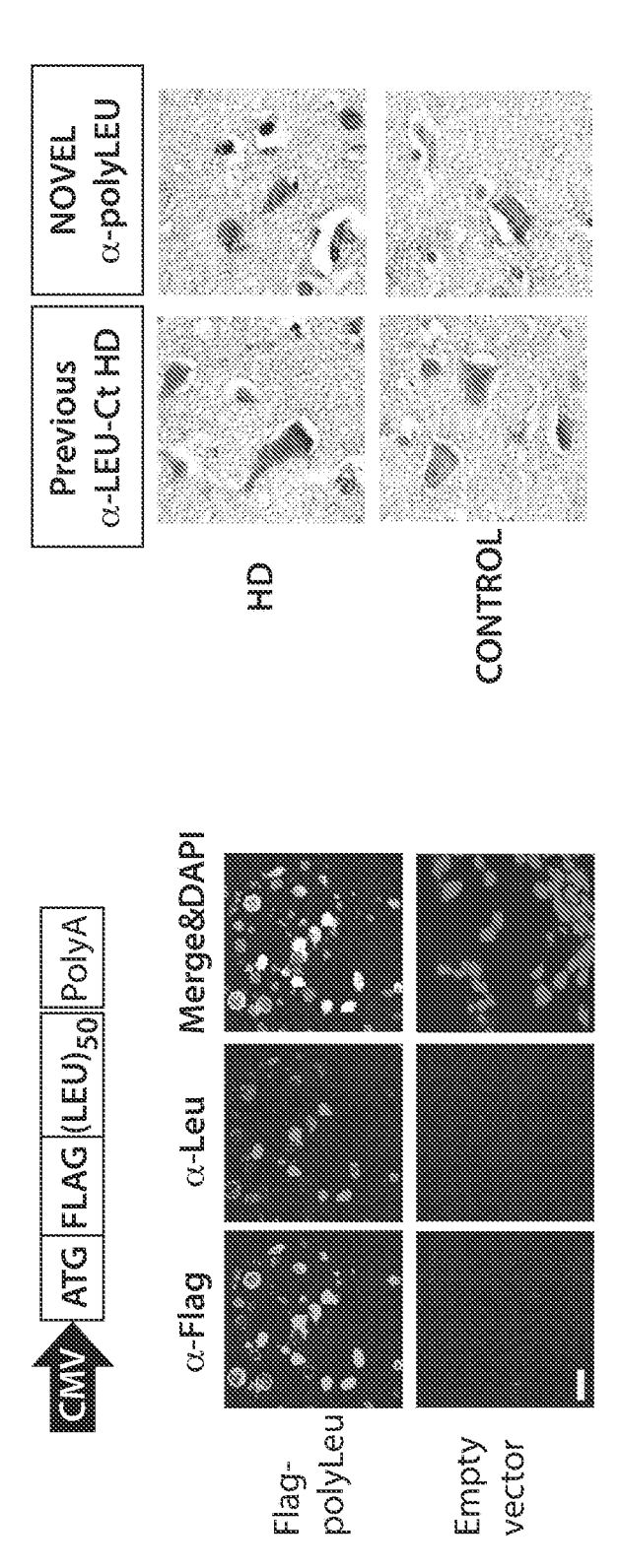
FIG. 22 shows representative data for validation of anti-POLYLEU antibody, which targets the homopolymeric leucine repeat of RAN proteins. anti-POLYLEU detects immunopositive cells in transfected cells and patient-derived HD tissue.
Figure 23:
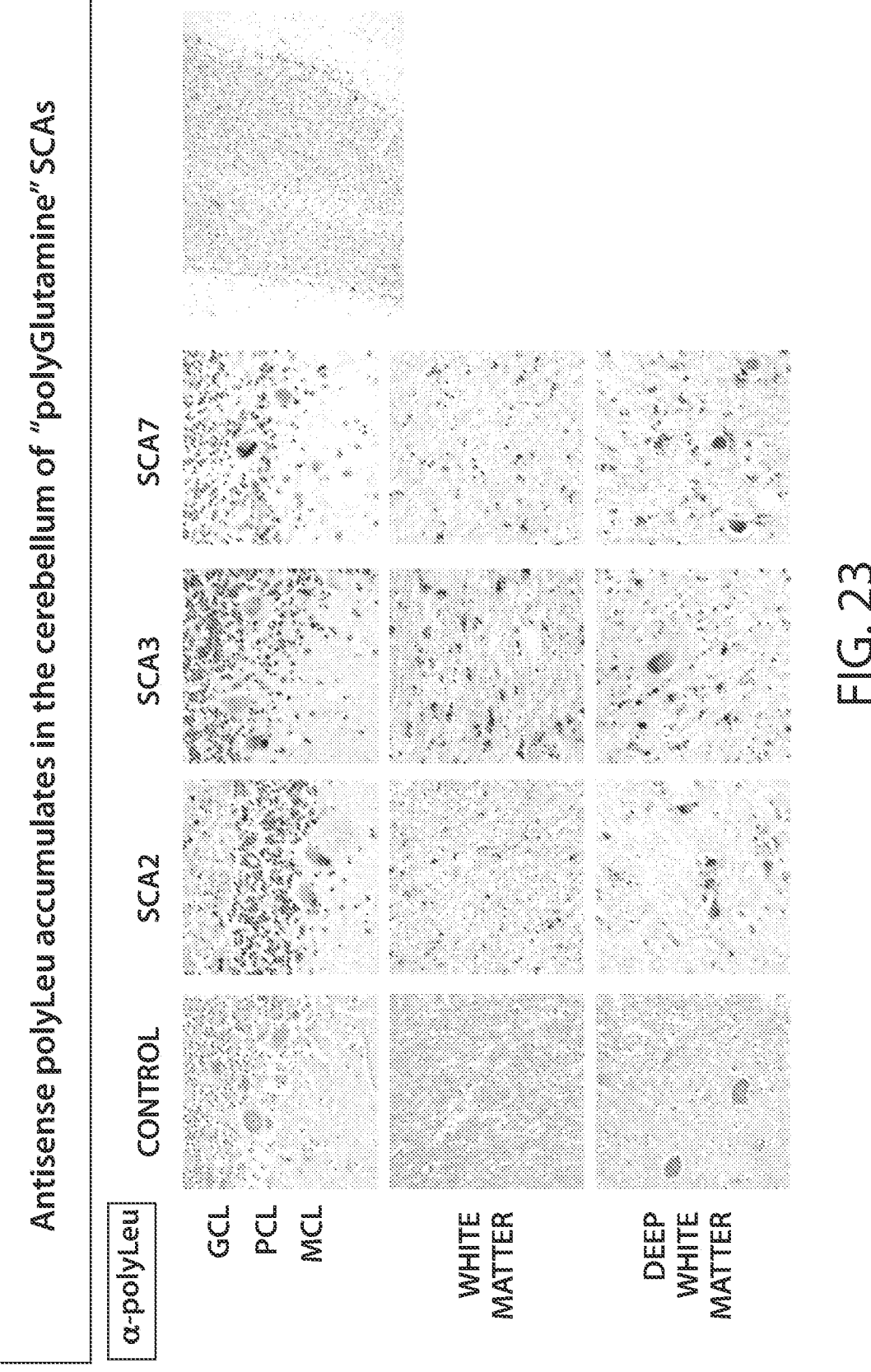
FIG. 23 shows representative data indicating that antisense translated polyLeu accumulates in the cerebellum of "polyGlutamine" SCAs (SCA2, SCA3, SCA7).
Figure 24:
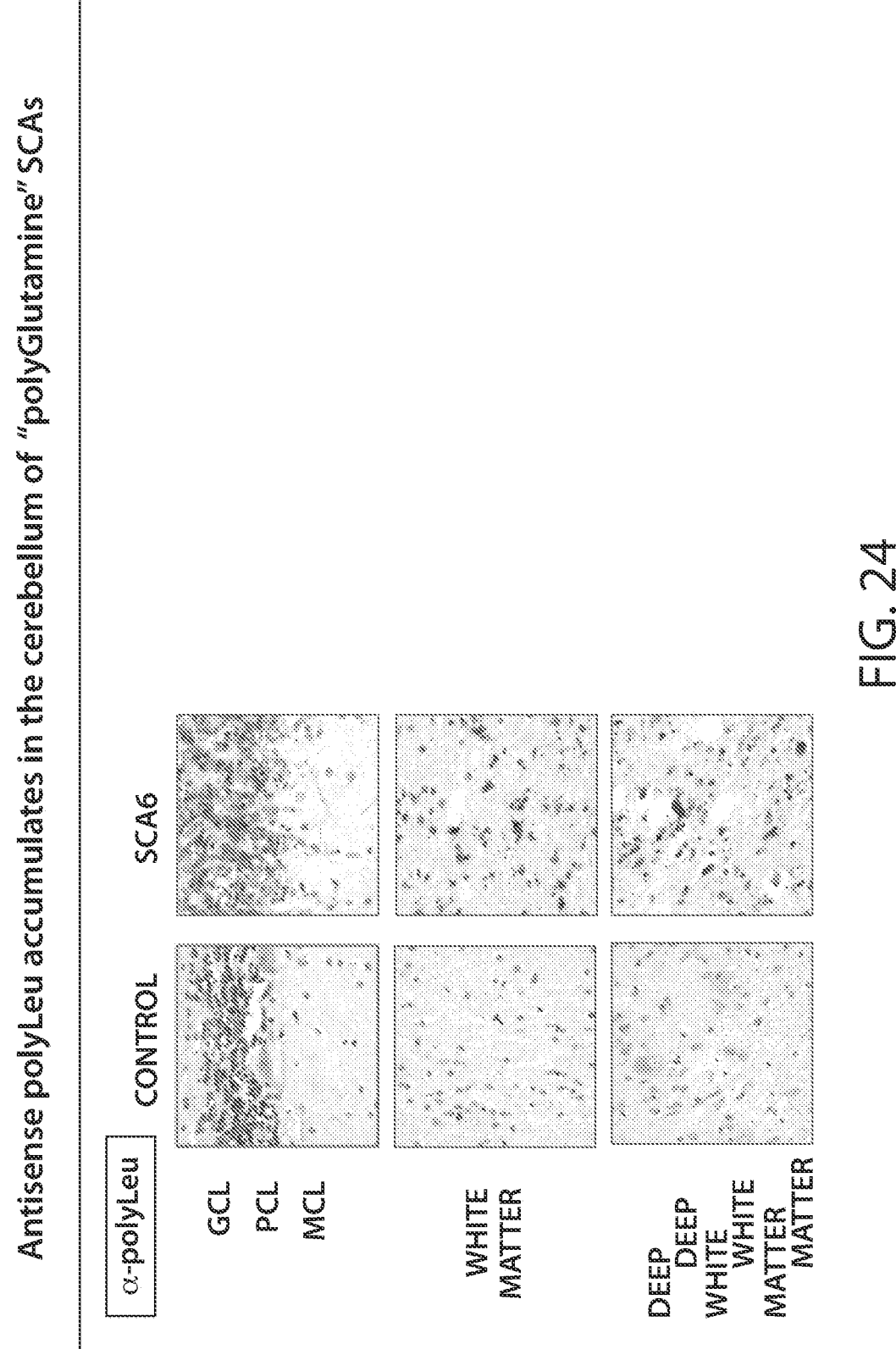
FIG. 24 shows representative data indicating that antisense translated polyLeu accumulates in the cerebellum of "polyGlutamine" SCA6.
Figure 25:
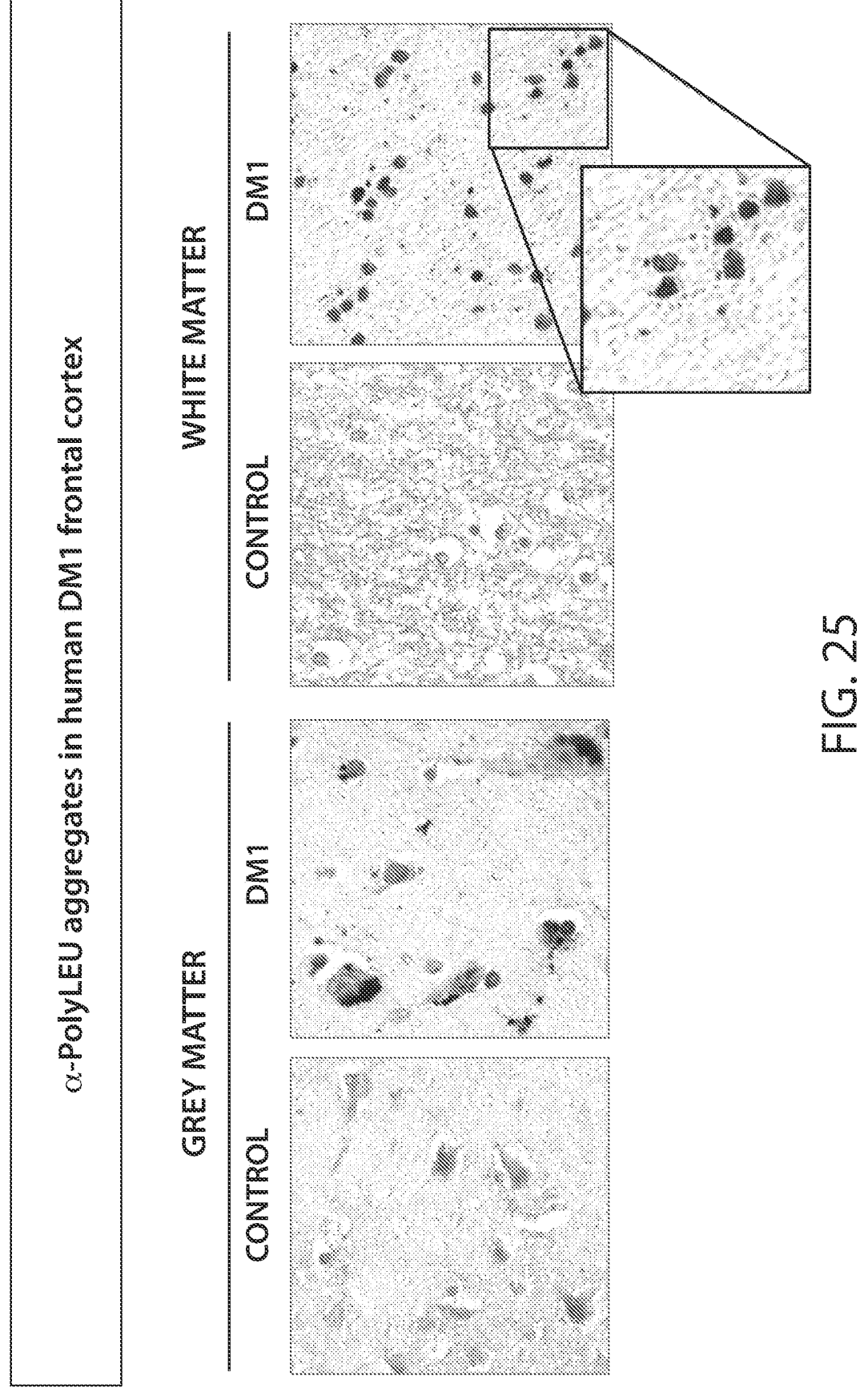
FIG. 25 shows representative data indicating that polyLeu RAN proteins accumulate in the frontal cortex of DM1 patients.
Figure 26:
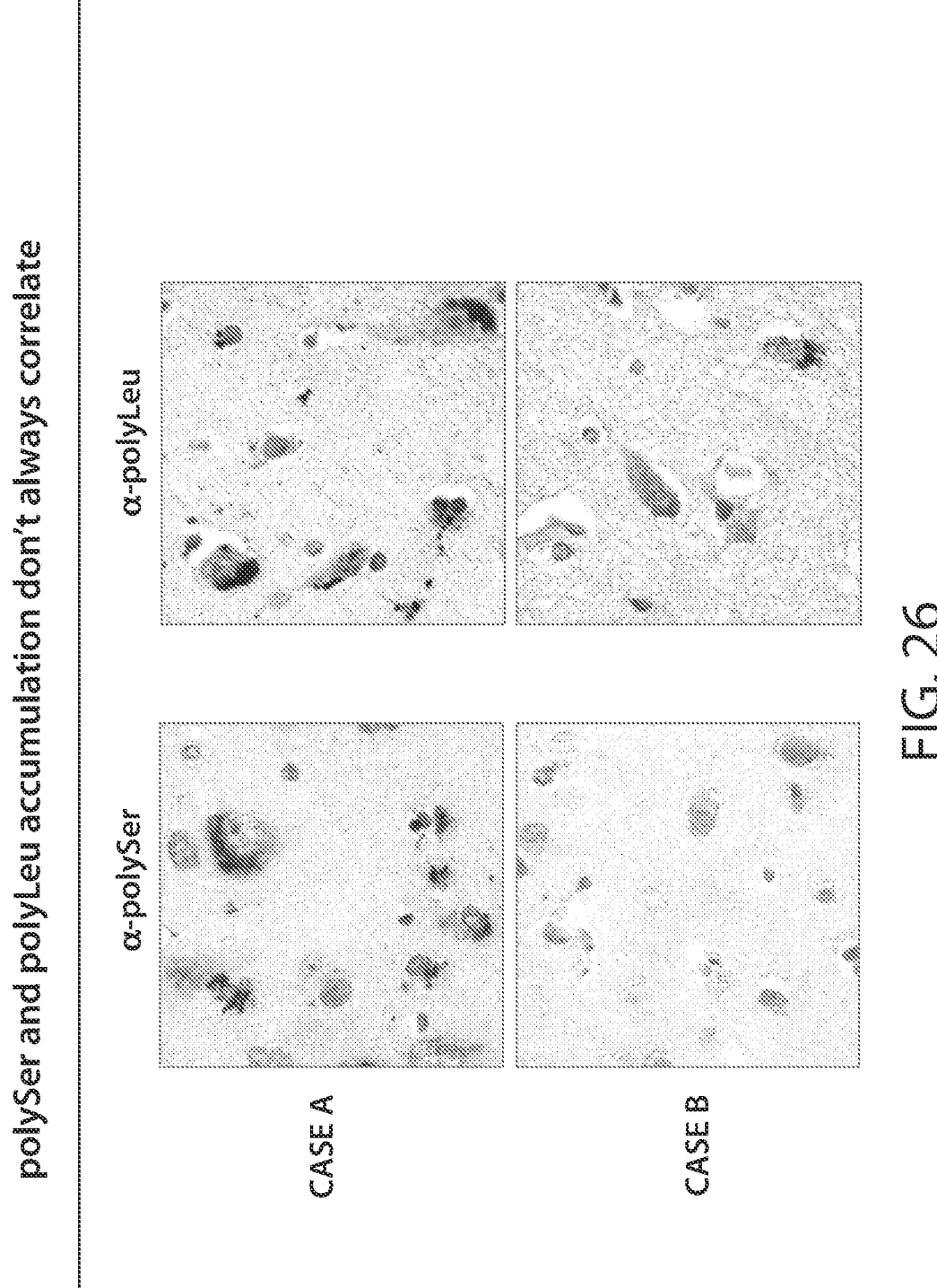
FIG. 26 shows representative data indicating that polyLeu and polySer RAN proteins do not always accumulate in the same regions.
Figure 27:
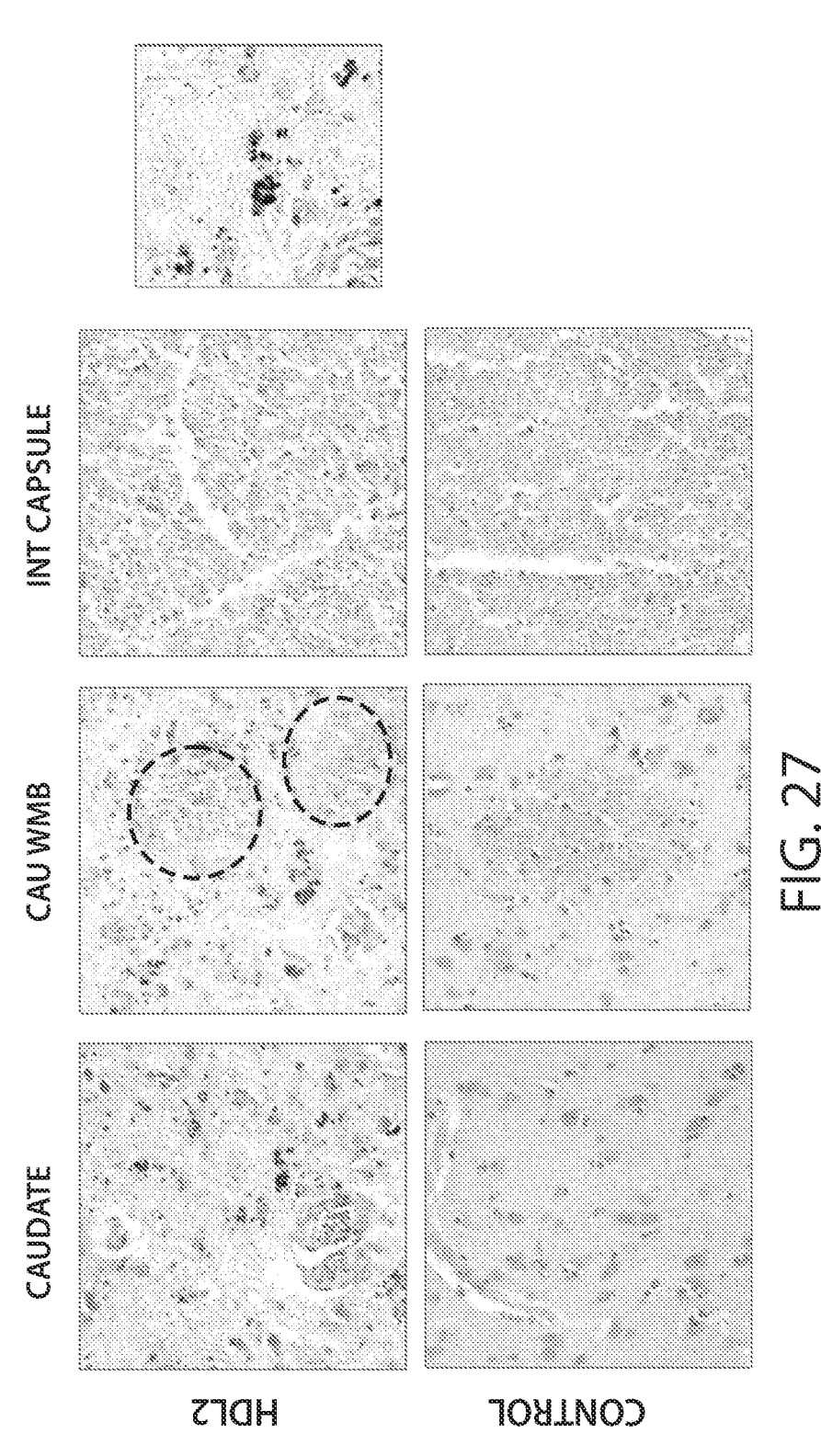
FIG. 27 shows representative data indicating that anti-POLYLEU antibody detects RAN positive cells in patient-derived HDL2 striatum.
Figure 28:
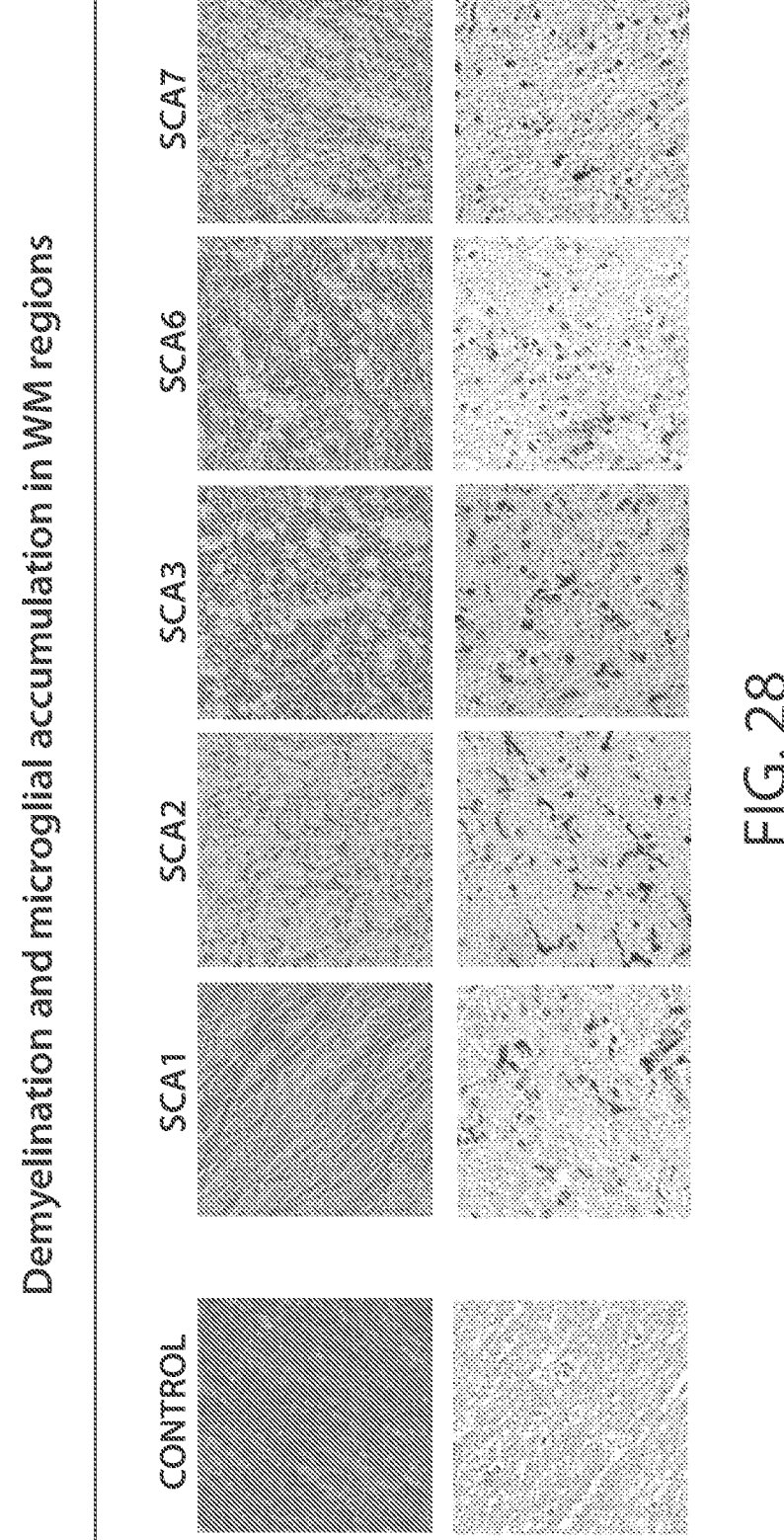
FIG. 28 shows representative data indicating demyelination and microglial accumulation in white matter (WM) regions of SCA patients.
Figure 29:
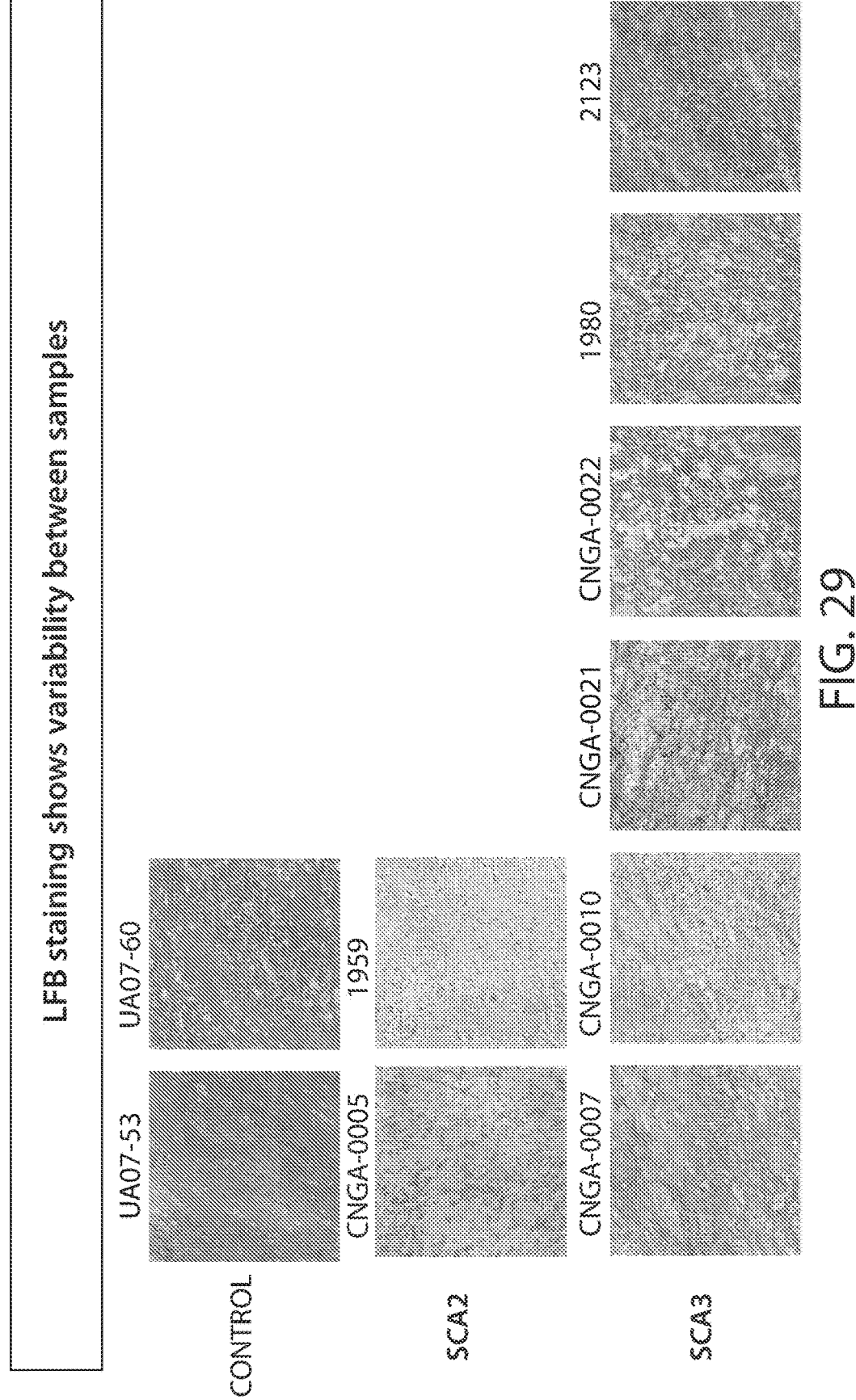
FIG. 29 shows representative luxol fast blue (LFB) staining data.
Figure 30:
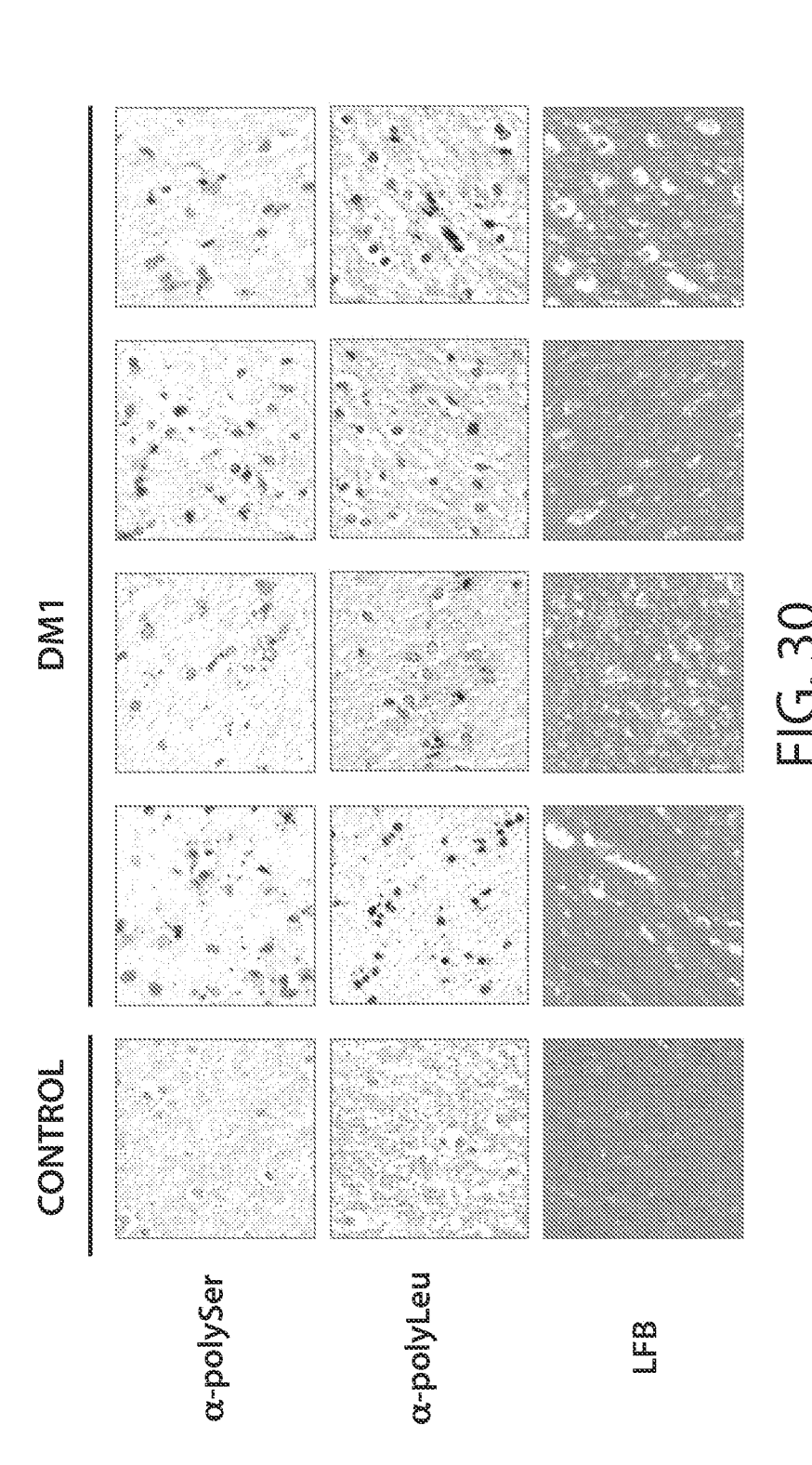
FIG. 30 shows representative data indicating polySer and polyLeu accumulation in regions with white matter abnormalities.
Figure 31:
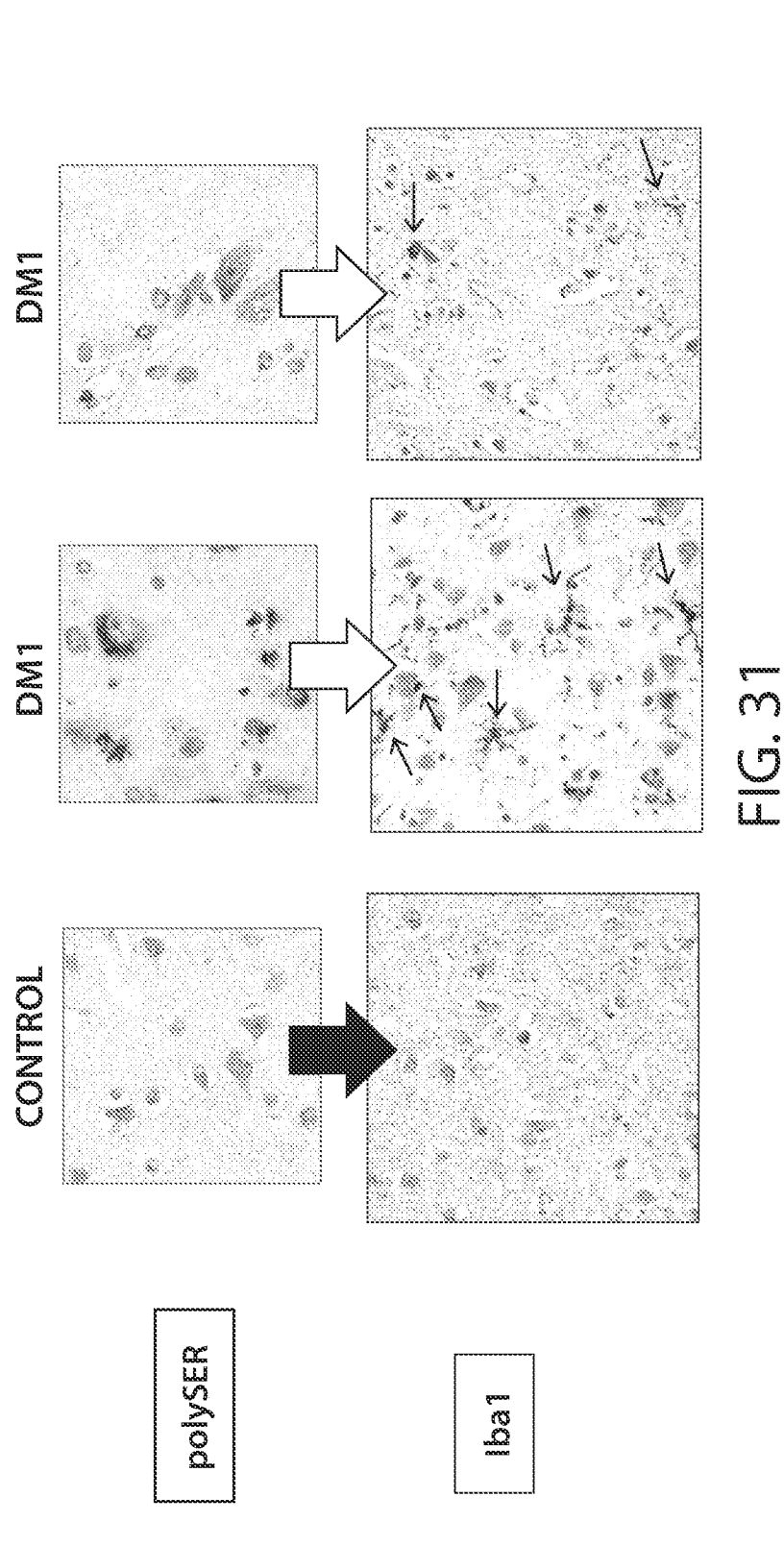
FIG. 31 shows representative data indicating DM1 polySer and polyLeu accumulation strongly associates with neuroinflammation.
Figure 32:
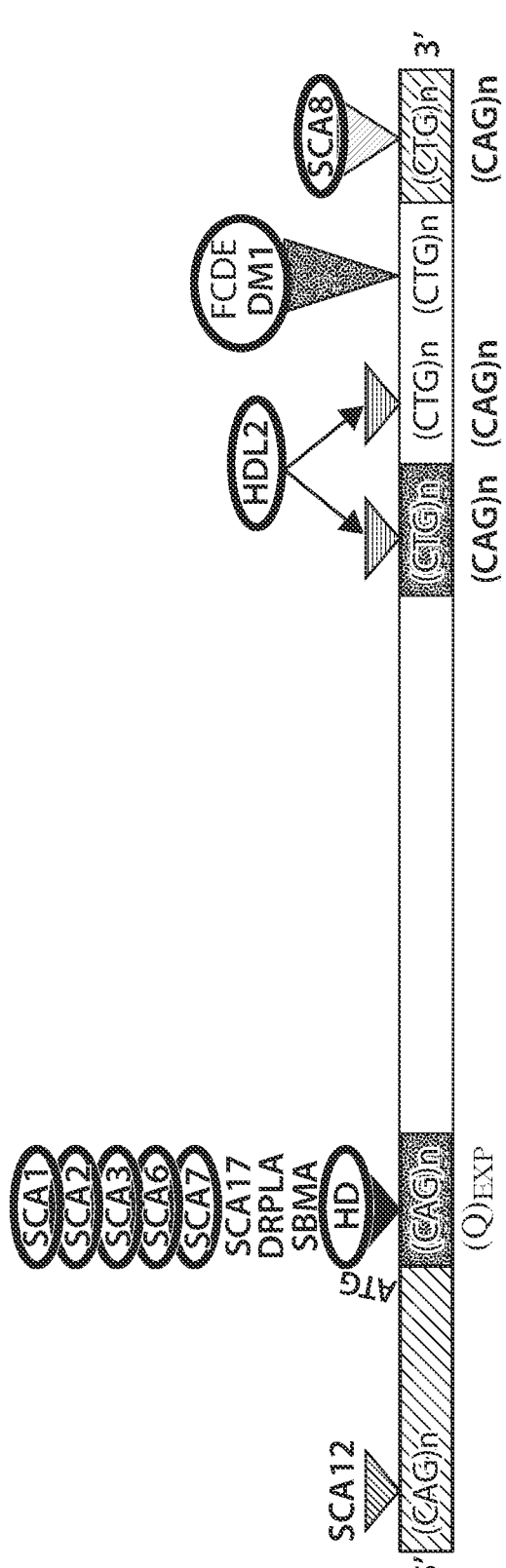
FIG. 32 shows a schematic depicting anti-POLYLEU and anti-POLYSER antibodies are tools for characterizing RAN proteins across all CAG•CTG expansion diseases.

Aspects of the disclosure relate to methods and kits for detecting certain RAN proteins, such as RAN proteins having a homopolymeric repeat region (e.g., a polyLeucine repeat region, a polySerine repeat region, etc.) in a sample. In some embodiments, an immunoassay is used to detect or measure levels of one or more RAN proteins in a biological sample (e.g., a serum sample) obtained from a subject.

In some aspects, the disclosure relates to a method for detecting one or more RAN proteins in a subject. In some embodiments, the method comprises: contacting a biological sample obtained from a subject with an anti-RAN protein antibody that targets a RAN protein homopolymeric repeat to form an anti-RAN antibody-target RAN protein complex; contacting the complex with an detectable agent to form a labeled complex; detecting the labeled complex; and identifying that the subject has a CAG and/or CTG expansion repeat-associated disease based on the presence of the labeled complex.

The disclosure is based, in part, on anti-RAN protein antibodies that target (e.g., bind specifically) to homopolymeric repeat regions of certain RAN proteins, such as polyLeucine repeat RAN proteins and polySerine repeat RAN proteins. It was surprisingly discovered that polySerine and polyLeucine RAN proteins are translated from CAG and/or CTG repeat expansions of certain genes associated with neurodegenerative diseases, such as spinocerebellar ataxias (SCA) (e.g., SCA1, SCA2, SCA3, SCA6, SCAT, SCA8, SCA12, SCA17, etc.), Huntington's disease (HD), Huntington disease-like 2 (HDL2), Dentatorubral-pallidoluysian atrophy (DRPLA), Spinal-bulbar muscular atrophy (SBMA), Fuchs' endothelial corneal dystrophy (FECD), and myotonic dystrophy (DM1).

RAN Proteins

In some aspects, the disclosure relates to methods of detecting one or more RAN proteins (e.g., detecting the level of one or more RAN proteins) in a biological sample obtained from a subject.

A "RAN protein (repeat-associated non-ATG translated protein)" is a polypeptide translated from mRNA sequence carrying a nucleotidic expansion in the absence of an AUG initiation codon. RAN proteins may comprise expansion repeats of one amino acid, termed homopolymeric amino acid repeats, two amino acids (di-amino acid repeats), three amino acids (tri-amino acid repeats), four amino acids (tetra-amino acid repeats), or five amino acids (penta-amino acid repeats).

Generally, a RAN protein may comprise between about 2 and about 10,000 amino acid repeats. In some embodiments, a RAN protein comprises between 20 and 100 amino acid repeats, 50 and 200 amino acid repeats, 100 and 500 amino acid repeats, 400 and 800 amino acid repeats, 700 and 1000 amino acid repeats, 800 and 1500 amino acid repeats, etc. In some embodiments, a RAN protein comprises a poly-amino acid repeat that is between 10 and 500 amino acid residues in length. In some embodiments, a RAN protein comprises a poly-amino acid repeat that is between 20 and 300 amino acid residues in length. In some embodiments, a RAN protein comprises a poly-amino acid repeat that is between 30 and 200 amino acid residues in length. In some embodiments, a RAN protein comprises a poly-amino acid repeat that is between 40 and 100 amino acid residues in length. In some embodiments, a RAN protein comprises a poly-amino acid repeat that is between 50 and 90 amino acid residues in length. In some embodiments, a RAN protein comprises a poly-amino acid repeat that is between 60 and 80 amino acid residues in length. In some embodiments, a RAN protein comprises a poly-amino acid repeat that is at least 20, at least 25, at least 30, at least 40, at least 50, at least 60, at least 70, at least 80, at least 90, at least 100, or at least 200 amino acid residues in length. In some embodiments, a RAN protein has a poly-amino acid repeat more than 200 amino acid residues (e.g., 500, 1000, 5000, 10,000, etc.) in length. In some embodiments, a RAN protein comprising a homopolymeric repeat region comprises one or more non-repeat regions (e.g., an N-terminal region, a C-terminal region, etc.).

In some embodiments, a RAN protein comprising a homopolymeric repeat region comprises a C-terminal region. A "C-terminal portion" or "C-terminus" of a RAN protein comprises the amino acid sequence encoded by a nucleotide sequence downstream of the poly-amino acid repeat region within the intron of a gene (e.g., Htt, HDL2, ATXN1, ATXN2, ATXN3, CACNA1A, ATXN7, ATXN8OS, and DMPK, etc.) for the sense transcript or a nucleotide sequence downstream of the poly-amino acid repeat region within the intron of a gene (e.g., Htt, HDL2, ATXN1, ATXN2, ATXN3, CACNA1A, ATXN7, ATXN8OS, and DMPK, etc.) for the antisense transcript.

In some embodiments, the C-terminal portion of a RAN protein comprises one or more contiguous amino acids in a sequence which begins at the amino acid immediately following the poly-amino acid repeat portion of the RAN protein and which is encoded by the sense transcript of the gene (e.g., Htt, HDL2, ATXN1, ATXN2, ATXN3, CACNA1A, ATXN7, ATXN8OS, and DMPK, etc.). In some embodiments, the C-terminal portion of a RAN protein comprises one or more contiguous amino acids in a sequence which begins at the amino acid immediately following the poly-amino acid repeat portion of the RAN protein and which is encoded by the antisense transcript of the gene (e.g., Htt, HDL2, ATXN1, ATXN2, ATXN3, CACNA1A, ATXN7, ATXN8OS, and DMPK, etc.).

In some embodiments, the C-terminal portion of a RAN protein comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, or more than 75 contiguous amino acids in a sequence which begins at the amino acid immediately following the poly-amino acid repeat portion of the RAN protein. In some embodiments, the C-terminal portion of a RAN protein comprises 1-5, 3-10, 5-15, 8-20, 10-25, 13-30, 15-35, 18-40, 20-45, 23-50, 25-55, 28-60, 30-65, 33-70, 35-75, or more than 75 contiguous amino acids in a sequence which begins at the amino acid immediately following the poly-amino acid repeat portion of the RAN protein.

RAN protein-encoding sequences can be found in a subject's genome (e.g., a human subject's genome) at multiple loci, including, but not limited to, Htt, HDL2, ATXN1, ATXN2, ATXN3, CACNA1A, ATXN7, ATXN8OS, and DMPK. In some embodiments, a RAN protein is translated by a CAG•CTG expansion repeat. In some embodiments, a CAG expansion repeat comprises between about 10 and about 10,000 CAG repeats (e.g., about 10, 20, 50, 100, 500, 1000, 2500, 5000, or 10000 CAG repeats). In some embodiments, a CAG expansion repeat comprises more than 10000

CAG repeats. In some embodiments, a CTG expansion repeat comprises between about 10 and about 10,000 CTG repeats (e.g., about 10, 20, 50, 100, 500, 1000, 2500, 5000, or 10000 CTG repeats). In some embodiments, a CTG expansion repeat comprises more than 10000 CTG repeats.

In some embodiments, RAN protein translation caused by a CAG•CTG expansion results in translation of one or more homopolymeric RAN proteins, for example polyAlanine, polySerine, polyLeucine, or polyCysteine (polyAla, polySer, polyLeu and polyCys), in addition to poly-Glutamine (polyGln or polyQ). Examples of homopolymeric RAN proteins include "AAAAAAAAAAAAAAAAAAAAA" (poly-Alanine) (SEQ ID NO: 1), "LLLLLLLLLLLLLLLLLLLLL" (poly-Leucine) (SEQ ID NO: 2), "SSSSSSSSSSSSSSSSSSSSS" (poly-Serine) (SEQ ID NO: 3), and "CCCCCCCCCCCCCCCCCCCCC" (poly-Cysteine) (SEQ ID NO: 4). RAN proteins may be expressed from a sense strand of an expansion repeat, an antisense strand of an expansion repeat, or both a sense strand and an antisense strand of an expansion repeat.

In the context of Huntington's disease (HD), RAN protein translation is caused by a CAG•CTG expansion in the Htt gene, which results in translation of RAN proteins polyAlanine, polySerine, polyLeucine, and polyCysteine (polyAla, polySer, polyLeu and polyCys), in addition to poly-Glutamine (polyGln or polyQ).

In the context of SCA8 and DM1, RAN protein translation is caused by a CTG•CAG repeat expansion. The SCA8 expansion mutation is bidirectionally transcribed and produces both CUG (ATXN8OS) and CAG (ATXN8) expansion RNAs, which are expressed in opposite directions across the expansion mutation. The CUG expansion transcripts form RNA foci, and the expanded CAG ATXN8 transcript expressed in the opposite direction produces a nearly pure polyGln protein from an unusually short ORF that contains an AUG-initiation codon directly upstream of the CAG repeat. This results in translation of the RAN proteins polyAlanine, polySerine, polyLeucine, and polyCysteine (polyAla, polySer, polyLeu and polyCys), in addition to poly-Glutamine (polyGln or polyQ).

Examples of additional RAN proteins and methods of identifying RAN proteins are described, for example, in International PCT Application PCT/US2020/040725, filed on Jul. 2, 2020, the entire contents of which are incorporated herein by reference.

Subjects and Biological Samples

In some embodiments, a biological sample is obtained from a subject having or that is suspected of having a disease associated with RAN protein translation. Generally, a biological sample can be blood, serum (e.g., plasma from which the clotting proteins have been removed), or cerebrospinal fluid (CSF). However, the skilled artisan will recognize other suitable biological samples, such as CNS tissue (e.g., brain tissue, spinal tissue, etc.) and cells (e.g., brain cells, neuronal cells, skin cells, etc.). In some embodiments, a biological sample is a cerebrospinal fluid (CSF) sample. In some embodiments, a biological sample is a blood sample or a tissue sample. In some embodiments, a blood sample is a sample of whole blood, a plasma sample, or a serum sample. In some embodiments, a tissue sample is a CNS tissue sample. In some embodiments, a blood sample is treated to remove white blood cells (e.g., leukocytes), such as the buffy coat of the sample.

In some embodiments, a biological sample obtained from a subject is stored at a temperature between −80° C. and about 23° C. (e.g., room temperature). In some embodiments, a biological sample obtained from a subject is stored at a temperature between 0° C. and about 23° C. (e.g., about 0, 1, 2, 3, 4, 5, 6, 7, 8, 9, 10, 11, 12, 13, 14, 15, 16, 17, 18, 19, 20, 21, 22, or 23° C.). In some embodiments, a biological sample obtained from a subject is stored at a temperature between 20° C. and about 25° C. (e.g., about 20, 21, 22, 23, 24, or 25° C.).

A subject can be a mammal (e.g., human, mouse, rat, goat, guinea pig, rabbit, dog, cat, or pig). In some embodiments, the subject is a human. In some embodiments, a subject is a mammalian subject. In some embodiments, a subject is a human or a mouse. In some embodiments, a subject is a mouse. In some embodiments, a subject is a C9-BAC mouse. The C9-BAC mouse model of ALS is described, for example, in International PCT Application PCT/US2014/022670, filed on Mar. 10, 2014, published as WO2014/159247, and Liu, et al., (2016) Neuron 90(3):521-34, the entire contents of each of which are incorporated herein by reference.

In some embodiments, a subject is characterized by a CAG repeat expansion and/or a CTG repeat expansion in a gene (e.g., a human gene or an orthologue thereof) selected from Htt, HDL2, ATXN1, ATXN2, ATXN3, CACNA1A, ATXN7, ATXN8OS, and DMPK. Generally, a RAN protein may be expressed from a sense strand of a repeat expansion, an antisense strand of a repeat expansion, or both a sense strand and an antisense strand of a repeat expansion (e.g., a sense and/or antisense strand of any of the foregoing: Htt, HDL2, ATXN1, ATXN2, ATXN3, CACNA1A, ATXN7, ATXN8OS, and DMPK).

In some embodiments, a subject has or is suspected of having a disease associated with a CAG•CTG expansion repeat. Examples of CAG•CTG expansion repeat-associated diseases include but are not limited to Huntington's disease (HD), spinocerebellar ataxias (SCA) (e.g., SCA1, SCA2, SCA3, SCA6, SCAT, SCAB, SCA12, SCA17, etc.), Huntington disease-like 2 (HDL2), Dentatorubral-pallidoluysian atrophy (DRPLA), Spinal-bulbar muscular atrophy (SBMA), Fuchs' endothelial corneal dystrophy (FECD), and myotonic dystrophy (DM1).

In some embodiments, a subject exhibits one or more signs or symptoms of a disease associated with RAN protein translation. For example, a "subject having or suspected of having myotonic dystrophy" (e.g., myotonic dystrophy type 1 (DM1) or myotonic dystrophy type 2 (DM2)) can be a subject exhibiting one or more signs or symptoms of DM1 and/or DM2, including but not limited to: delayed muscle relaxation, muscle weakness, prolonged involuntary muscle contraction, or loss of muscle; and/or abnormal heart rhythm, cataracts, or difficulty swallowing.

A "subject having or suspected of having spinocerebellar ataxia" (e.g., spinocerebellar ataxia types 1, 2, 3, 6, 7, 8, 10, 12, 17, 31, or 36) can be a subject exhibiting one or more signs or symptoms of spinocerebellar ataxia, including but not limited to: speech and swallowing difficulties, muscle stiffness (e.g., spasticity), weakness in the muscles that control eye movement (e.g., ophthalmoplegia), rapid, involuntary eye movements (e.g., nystagmus), uncoordinated movement and poor balance (e.g., ataxia), muscle wasting, slow eye movement, dementia, uncontrolled muscle tensing (e.g., dystonia), rigidity, tremors, bulging eyes, double vision, loss of coordination in arms, progressive vision loss, blindness, changes in sensation or reflexes, truncal instability, hyperactive tendon reflexes, scanning dysarthria characterized by a drawn-out slowness of speech, cerebellar ataxia, unsteady gait, upper-limb ataxia, dysphagia, gait dysfunction, extrapyramidal features, pyramidal weakness, cognitive and behavioral disturbances, chorea, psychiatric disturbances, sensorineural hearing impairment, impaired vibratory sensation, rapid eye movements (e.g., saccades), trouble moving the eyes side-to-side (e.g., oculomotor apraxia), and/or droopy eyelids (e.g., ptosis).

A "subject having or suspected of having spinal bulbar muscular atrophy" can be a subject exhibiting one or more signs or symptoms of spinal bulbar muscular atrophy, including but not limited to: speech impairment, difficulty chewing and swallowing, impaired sleep, difficulty breathing, facial muscle weakness, difficulty conveying emotion, weakness and atrophy of the arm and leg muscles, twitching and cramping of muscles, enlarged breasts (in male subjects), reduced fertility and atrophy (e.g., shrinkage) of the testicles, abnormal processing of male hormones, muscle wasting, and/or difficulty walking.

A subject "having or suspected of having dentatorubral-pallidoluysian atrophy (DRPLA)" can be a subject exhibiting one or more signs or symptoms of DRPLA, including but not limited to: ataxia, uncontrollable movements of the limbs (e.g., choreoathetosis), psychiatric symptoms (e.g., delusions), and/or deterioration of intellectual function (e.g., dementia).

A subject "having or suspected of having Huntington's disease (HD)" can be a subject exhibiting one or more signs or symptoms of HD, including but not limited to: abnormality walking, increased muscle activity, involuntary movements, problems with coordination, loss of muscle, muscle spasms, amnesia, delusion, lack of concentration, mental confusion, slowness in activity, difficulty thinking and understanding, compulsive behavior, fidgeting, irritability, lack of restraint, delirium, depression, hallucination, paranoia, anxiety, apathy, mood swings, difficulty speaking, memory loss, tremor, and/or weight loss.

A subject "having or suspected of having Huntington's disease-like 2 syndrome (HDL2)" can be a subject exhibiting one or more signs or symptoms of HDL2, including but not limited to: progressive movement disorder (e.g., parkinsonism, chorea), cognitive and emotional decline (e.g., dementia, psychiatric disturbances), epileptic seizure(s), and/or any other signs or symptoms associated with HD.

A subject "having or suspected of having Fuchs' endothelial corneal dystrophy (FECD)" can be a subject exhibiting one or more signs or symptoms of FECD, including but not limited to: blurred or cloudy vision (e.g., a general lack of clarity of vision), fluctuation in vision (e.g., worse symptoms in the morning after awakening and gradually improving during the day), permanent vision impairment, glare, seeing halos around lights, and/or pain or grittiness from tiny blisters on the surface of cornea.

In some embodiments, a "subject having or suspected of having an expansion-repeat associated disease" can be a subject that is known or determined to have more than 19 (e.g., 20, 25, 30, 35, or more) repeats in a gene selected from Htt, HDL2, ATXN1, ATXN2, ATXN3, CACNA1A, ATXN7, ATXN8OS, and DMPK, or a subject exhibiting signs and symptoms of a neurodegenerative disease (e.g., HD, SCA1, SCA2, SCA3, SCA6, SCA7, SCA8, SCA12, SCA17, Huntington disease-like 2 (HDL2), DRPLA, SBMA, Fuchs' endothelial corneal dystrophy (FECD), DM1, etc.), including but not limited to motor dysfunction (e.g., spasticity), muscle atrophy, and/or neuropsychiatric manifestations (e.g., compulsive behavior, apathy, anxiety, etc.).

Therapeutic Agents

Methods of the disclosure are useful in some embodiments, for investigating the efficacy of a therapeutic agent (e.g., a therapeutic agent candidate) in an animal model of a disease or disorder associated with RAN protein translation. A "therapeutic agent candidate" generally refers to an agent (e.g., small molecule, interfering RNA, protein, peptide, antibody, vaccine, etc.) that is being tested for the ability to reduce or inhibit RAN protein translation in a cell or subject. Generally, a therapeutic agent can be a small molecule (e.g., metformin or a metformin derivative), an interfering RNA (e.g., dsRNA, siRNA, miRNA, amiRNA, ASO, aptamer, etc.), protein or fragment thereof, peptide, antibody (e.g., an anti-RAN protein antibody), etc. In some embodiments, a therapeutic agent is a small molecule, interfering nucleic acid, modified interfering nucleic acid, DNA aptamer, RNA aptamer, peptide, protein, antibody, antibody drug conjugate, other large molecule, gene therapy (including a gene therapy designed to deliver one or more of the other enumerated types of therapeutic agents), a natural product, or an herbal medicine. In some embodiments, a therapeutic agent modulates RAN protein expression, for example by modulating a pathway that controls RAN protein expression, such as the protein kinase R (PKR) pathway, EIF2 pathway, or EIF3 pathway.

In some embodiments, a small molecule is a modifier of eukaryotic initiation factor 2 (eIF2), eukaryotic initiation factor 3 (eIF3), protein kinase R (PKR), p62 (sequestome-1 or ubiquitin binding protein), LC3 (microtubule associated protein 1 light chain 3) I subunit, LC3 II subunit, or Toll-like receptor 3 (TLR3). In some embodiments, a small molecule is metformin or a pharmaceutically acceptable salt, co-crystal, tautomer, stereoisomer, solvate, hydrate, polymorph, isotopically enriched derivative, or prodrug thereof. In some embodiments, a small molecule is buformin, phenformin, metformin, or a derivative or functional analogue thereof. In some embodiments, a small molecule is an inhibitor of PKR such as TARBP2.

In some embodiments, an interfering nucleic acid is a dsRNA, siRNA, shRNA, miRNA, artificial miRNA (amiRNA), or antisense oligonucleotide (ASO). In some embodiments, an interfering nucleic acid modifies expression of eukaryotic initiation factor 2 (eIF2), eukaryotic initiation factor 3 (eIF3), protein kinase R (PKR), p62, LC3 I subunit, LC3 II subunit, or Toll-like receptor 3 (TLR3). In some embodiments, an interfering nucleic acid modifies expression of eIF2A or eIF2a. In some embodiments, an interfering nucleic acid inhibits expression of one or more eIF3 subunits selected from the group consisting of eIF3a, eIF3b, eIF3c, eIF3d, eIF3e, eIF3f, eIF3g, eIF3h, eIF3i, eIF3j, eIF3k, eIF3l, and eIF3m. In some embodiments, an interfering nucleic acid inhibits expression of protein kinase R (PKR). In some embodiments, an interfering nucleic acid inhibits expression of a gene (e.g., Htt, HDL2, ATXN1, ATXN2, ATXN3, CACNA1A, ATXN7, ATXN8OS, and DMPK, etc.). In some embodiments, an interfering nucleic acid binds directly to a repeat sequence as described herein.

In some embodiments, a protein (e.g., a therapeutic protein) modifies eukaryotic initiation factor 2 (eIF2), eukaryotic initiation factor 3 (eIF3), protein kinase R (PKR), p62, LC3 I subunit, LC3 II subunit, or Toll-like receptor 3 (TLR3). In some embodiments, a protein (e.g., a therapeutic protein) is a dominant-negative variant of protein kinase R (PKR) or a dominant-negative variant of TLR3 protein. In some embodiments, a dominant-negative variant comprises a mutation at amino acid position 296. In some embodiments, the mutation is K296R.

In some embodiments, a therapeutic agent (e.g., a nucleic acid encoding a therapeutic protein, interfering nucleic acid, etc.) is delivered to the subject by a vector. In some embodiments, the vector is a viral vector. In some embodiments, the vector is a lentiviral vector, retroviral vector, adenoviral vector, or adeno-associated virus (AAV) vector. In some embodiments, a viral vector is a recombinant adeno-associated virus (rAAV). In some embodiments, an rAAV comprises an AAV8 capsid protein or variant thereof. In some embodiments, an anti-RAN protein peptide vaccine is delivered by a viral vector. In some embodiments, one or more viral vectors encoding an anti-RAN protein antibody or fragment thereof is delivered by a viral vector.

In some embodiments, a therapeutic agent candidate is an antibody. In some embodiments, an antibody targets eukaryotic initiation factor 2 (eIF2), eukaryotic initiation factor 3 (eIF3), protein kinase R (PKR), p62, LC3 I subunit, LC3 II subunit, or Toll-like receptor 3 (TLR3). Such antibodies are known in the art (see, e.g., Duffy et al. Cell Immunol. 2007 August; 248(2):103-14. PubMed PMID: 18048020). Those skilled in the art will understand how to make antibodies binding to the enumerated protein targets and to screen for the desired modulation of the functions of the target proteins.

In some embodiments, an antibody is an anti-RAN protein antibody. In some embodiments, an anti-RAN protein antibody specifically binds to the poly-amino acid repeat of the RAN protein. In some embodiments, an anti-RAN protein antibody specifically binds to one or more polyLeu repeats of the RAN protein. In some embodiments, an anti-RAN protein antibody specifically binds to one or more polySer repeats of the RAN protein. In some embodiments, an anti-RAN protein antibody specifically binds to the C-terminus of the RAN protein. In some embodiments, an anti-RAN protein antibody specifically binds to an amino acid sequence comprising any one of SEQ ID NOs: 17-26.

In some embodiments, an anti-RAN protein antibody is a monoclonal antibody. In some embodiments, an anti-RAN protein antibody is a polyclonal antibody. In some embodiments, anti-RAN antibodies are generated with binding activity to newly identified RAN proteins occurring in the RAN protein-associated neurological disease which are predicted by the sequences of the novel enriched repeat expansion mutations. In some embodiments, the loci comprise known risk factors for the RAN protein-associated neurological disease, now identified as containing novel repeat-expansion mutations capable of producing one or more types of RAN proteins. Examples of anti-RAN antibodies are disclosed, for example, in International Patent Application No. PCT/US2020/051671, filed Sep. 18, 2020, and in U.S. Publication No. 2013/0115603, the entire contents of each of which are incorporated herein by reference.

In some embodiments, a therapeutic agent candidate is a vaccine configured to elicit an immune response against one or more RAN proteins (e.g., polySer, polyLeu, etc.) expressed from an expansion repeat in the subject. Examples of vaccines configured to elicit an immune response against one or more RAN proteins are described, for example, in International Patent Application No. PCT/US2020/051670, filed Sep. 18, 2020, the entire contents of which are incorporated herein by reference.

In some embodiments, a therapeutic agent candidate is an antisense oligonucleotide (ASO).

The identification and selection of appropriate additional therapeutic agents is within the capabilities of a person of ordinary skill in the art, and will depend upon the disease from which the subject is suffering. For example, in some embodiments one or more therapeutic agents for Fragile X Syndrome (e.g., selective serotonin reuptake inhibitors, carbamazepine, methylphenidate, Trazodone, sertraline, metformin, cannabidiol (CBD), acamprosate, lovastatin, minocycline, etc.), Spinocerebellar Ataxia (e.g., baclofen, riluzole, amantadine, varenicline, etc.), amyotrophic lateral sclerosis (ALS) (e.g., riluzole, etc.), myotonic dystrophy type 1 (tideglusib, mexiletine, etc.), or Huntington's disease (tetrabenazine (Xenazine), baclofen, deutetrabenazine (Austedo), haloperidol, chlorpromazine, risperidone, quetiapine, amantadine, levetiracetam, clonazepam, citalopram, fluoxetine, sertraline, olanzapine, alproate, carbamazepine, lamotrigine, cysteamine, PBT2, PDE10A inhibitor, pridopidine, laquinimod, etc.) are administered to the subject.

Administration of a treatment may be accomplished by any method known in the art (see, e.g., Harrison's Principle of Internal Medicine, McGraw Hill Inc.). Administration may be local or systemic. A therapeutic agent can be administered by any route, including enteral (e.g., oral), parenteral, intravenous, intramuscular, intra-arterial, intramedullary, intrathecal, intratracheal, subcutaneous, intraventricular, transdermal, intradermal, ocular, rectal, intravaginal, intraperitoneal, topical (as by powders, ointments, creams, and/or drops), mucosal, nasal, buccal, sublingual, intratracheal instillation, bronchial instillation, inhalation, as an oral spray, as a nasal spray, and/or as an aerosol. Systemic routes include oral and parenteral. Specifically contemplated routes are oral administration, intravenous administration (e.g., systemic intravenous injection), regional administration via blood and/or lymph supply, and/or direct administration to an affected site. In some embodiments, a treatment as described by the disclosure is administered to a subject by intramuscular injection. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject. Compositions for different routes of administration are well known in the art (see, e.g., Remington's Pharmaceutical Sciences by E. W. Martin). Dosage will depend on the subject and the route of administration. Dosage can be determined by the skilled artisan.

Immunoassays

In some embodiments, compositions and methods described by the disclosure are useful for diagnosing a subject as having a disease or disorder associated with CAG and/or CTG repeat expansions. In some embodiments, compositions and methods described by the disclosure are additionally or alternatively useful for monitoring (e.g., longitudinally measuring) levels of one or more RAN proteins (e.g., polyLeucine, polySerine, etc.) in a subject who has been or is being administered one or more therapeutic agents for treatment of a disease or disorder associated with CAG and/or CTG repeat expansions.

In some embodiments, the tissue distribution of one or more RAN proteins can be used to diagnose a subject as having an expansion repeat-associated disease. In some embodiments, the tissue distribution of one or more RAN proteins can be used to detect the presence or severity of an expansion repeat-associated disease in a subject.

The disclosure is based, in part, on certain immunoassays (e.g., immunohistochemistry assays, electrochemiluminescence-based immunoassays, Western blots, immunofluorescence assays) that can be used to detect one or more RAN proteins (e.g., homopolymeric RAN proteins, such as polySer, polyLeu, etc.) in a biological sample (e.g., serum) obtained from a subject. In some embodiments, sample processing time and conditions (e.g., incubation time and incubation temperature) affect the amount of background signal observed in a given blood sample. For example if a serum sample is incubated (e.g., held or stored) at room temperature for more than 24 hours after being obtained from the subject, the levels of RAN proteins in the sample are, in some embodiments, indistinguishable from control samples due to high background signal.

In some embodiments, an immunoassay is performed on a biological sample (e.g., a blood sample) within two days of being obtained from a subject. In some embodiments, an immunoassay is performed on a biological sample (e.g., a blood sample) between about 1 minute and about 48 hours after being obtained from a subject. In some embodiments, an immunoassay is performed on a biological sample (e.g., a blood sample) between about 10 minutes and about 45 hours after being obtained from a subject. In some embodiments, an immunoassay is performed on a biological sample (e.g., a blood sample) between about 20 minutes and about 40 hours after being obtained from a subject. In some embodiments, an immunoassay is performed on a biological sample (e.g., a blood sample) between about 30 minutes and about 32 hours after being obtained from a subject. In some embodiments, an immunoassay is performed on a biological sample (e.g., a blood sample) between about 40 minutes and about 30 hours after being obtained from a subject. In some embodiments, an immunoassay is performed on a biological sample (e.g., a blood sample) between about 50 minutes and about 26 hours after being obtained from a subject. In some embodiments, an immunoassay is performed on a biological sample (e.g., a blood sample) between about 60 minutes and about 24 hours after being obtained from a subject. In some embodiments, an immunoassay is performed on a biological sample (e.g., a blood sample) between about 1 minute, 2 minutes, 3 minutes, 4 minutes, 5 minutes, 6 minutes, 7 minutes, 8 minutes, 9 minutes, 10 minutes, 15 minutes, 20 minutes, 25 minutes, 30 minutes, 35 minutes, 40 minutes, 45 minutes, 50 minutes, 60 minutes (e.g., 1 hour), 90 minutes, 120 minutes (e.g., 2 hours), 3 hours, 4 hours, 5 hours, 6 hours, 7 hours, 8 hours, 9 hours, 10 hours, 12 hours, 14 hours, 16 hours, 18 hours, 20 hours, 25 hours, 30 hours, 40 hours, or 48 hours after being obtained from a subject.

In some embodiments of the immunoassay methods described by the disclosure, a sample (e.g., a biological sample) is treated by an antigen retrieval process to render one or more antigens within the sample accessible to detection agents (e.g., antibodies). As used herein, "antigen retrieval" (also referred to as epitope retrieval, or antigen unmasking) refers to a process in which a biological sample (e.g., blood, serum, CSF, etc.) is treated under conditions which expose antigens (e.g., epitopes) that were previously inaccessible to detection agents (e.g., antibodies, aptamers, and other binding molecules) prior to the process. Generally, antigen retrieval methods comprise steps including but not limited to heating, pressure treatment, enzymatic digestion, treatment with reducing agents, treatment with oxidizing agents, treatment with crosslinking agents, treatment with denaturing agents (e.g., detergents, ethanol, acids), or changes in pH, or any combination of the foregoing. Several antigen retrieval methods are known in the art, including, but not limited to, protease-induced epitope retrieval (PIER) and heat-induced epitope retrieval (HIER). In some embodiments, antigen retrieval procedures reduce the background signal and increase the sensitivity of detection techniques (e.g., immunohistochemistry (IHC), immuno-blot (such as Western Blot), ELISA, etc.).

For example, in some embodiments, antigen retrieval techniques increase the reproducibility of detection of RAN proteins by reducing instances of false positives. This allows the detection of "positive" samples with low levels of a target protein that may not otherwise be identified as "positive". In some embodiments, an antigen retrieval process is performed on the biological sample prior to the detection of one or more RAN proteins (e.g., detection by immuno-blot, such as Western blot, immunohistochemistry, ELISA, etc.).

In some embodiments, detection of RAN proteins in a biological sample is performed by Western blot. Western blots generally employ the use of a detection agent or probe to identify the presence of a protein or peptide. In some embodiments, detection of one or more RAN proteins is performed by immunoblot (e.g., dot blot, 2-D gel electrophoresis, etc.), immunohistochemistry (IHC), or ELISA. In some embodiments, detection of one or more RAN proteins is performed by an electrochemiluminescence-based immunoassay. In some embodiments, detection of one or more RAN proteins is performed by an immunofluorescence assay.

Generally, an "electrochemiluminescence-based immunoassay" refers to a biological assay in which the binding of one or more RAN proteins present in a biological sample to one or more anti-RAN protein antibodies (e.g., an anti-RAN protein antibody that binds specifically to a homopolymeric repeat region of a RAN protein, such as a polySer repeat or a polyLeu repeat) that are bound to a substrate, such as a microplate, are detected using electrochemiluminescent labels (e.g., detectable moieties which emit light when stimulated by electricity in the appropriate chemical environment (e.g., in the presence of tripropylamine, TPrA)). Electrochemiluminescent labels are described, for example by Muzyka (2014) *Biosens Bioelectron* 15(54):393-407.

In some embodiments, an electrochemiluminescence-based immunoassay is a Meso Scale Detection (MSD) assay. As used herein the term "meso scale detection (MSD) assay" refers to an immunoassay used for detection of analytes by electrochemiluminescence (e.g., using one or more detectable reagents, such as SULFO-TAG™ labels (e.g., labels comprising one or more Ruthenium complexes) that emit light upon electrochemical stimulation), for example as described by Moxness et al. (2005) *Clin. Chem.* 51(10): 1983-5, and U.S. Pat. No. 7,008,796, which is incorporated by reference with respect to its description of MSD assay steps.

Generally, a MSD assay comprises contacting a solid substrate, for example a multi-well assay plate comprising one or more target antibodies (e.g. one or more anti-RAN protein antibodies, such as anti-POLYLEU, anti-POLYSER, etc.) attached to the substrate, with a biological sample (e.g., a blood sample obtained from a subject that contains one or more RAN proteins having a homopolymeric repeat region) under conditions in which anti-RAN protein antibodies bind to the one or more RAN proteins to form a complex, and subsequently contacting the complexes with one or more secondary antibodies (e.g., an antibody that binds to the anti-RAN protein antibody portion of the complex, such as an anti-human antibody, anti-mouse antibody, anti-rabbit antibody, etc.) that are conjugated to a detectable reagent.

A detectable reagent may be a fluorescent label, chemiluminescent label, a radiolabel, or an electrochemiluminescent label. In some embodiments, a detectable reagent comprises an electrochemiluminescent moiety, for example as described in U.S. Pat. No. 5,310,687, which is incorporated herein by reference with respect to disclosure regarding such electrochemiluminescent moieties. In some embodiments, a detectable reagent comprises a Ruthenium complex, for example Ruthenium (II) tris-bipyridine-(4-methylsulfone), also referred to as $[Ru(Bpy)_3]^{+2}$, or a salt thereof.

A detectable reagent (e.g., a detectable moiety, for example a Ruthenium complex, such as a SULFO-TAG™) is generally conjugated to a secondary antibody. In some embodiments, a secondary antibody is a detection antibody. In some embodiments, a detection antibody is an antibody that binds to an anti-RAN protein antibody or to an antigen present in the species from which the sample has been obtained, such as an anti-human antibody, anti-mouse antibody, anti-rat antibody, anti-guinea pig antibody, etc.

Antibodies

Aspects of the disclosure relate to methods for detecting homopolymeric RAN proteins in a biological sample by using one or more anti-RAN protein antibodies (e.g., an anti-RAN protein antibody that binds specifically to a homopolymeric repeat region of a RAN protein, such as a polySer repeat or a polyLeu repeat). Further aspects of the disclosure relate to anti-RAN protein antibodies specific for a di-amino acid repeat-containing protein (e.g., a RAN protein) selected from a poly-Ser or a polyLeu repeat-containing protein. The anti-RAN protein antibody may recognize a region or regions of the di-amino acid repeat-containing protein (such as a repeat sequence or the C-terminus) or may recognize the entire di-amino acid repeat-containing protein.

In some embodiments, an anti-RAN protein antibody is an anti-poly-Serine or anti-poly-Leucine antibody. In some embodiments, an anti-RAN antibody targets (e.g., specifically binds to) a homopolymeric repeat region of a RAN protein. In some embodiments, an anti-RAN antibody does not target (e.g., does not specifically bind to) any portion of a RAN protein that does not comprise the poly amino acid repeat. In some embodiments a set (or combination) of anti-RAN antibodies (e.g., a combination of two or more anti-RAN antibodies, such as anti-POLYLEU and anti-POLYSER) is used to detect one or more RAN proteins in a biological sample.

In some embodiments, the disclosure provides methods of producing anti-RAN protein antibodies. Methods of producing an antibody as described herein typically comprise administering to a cell or a subject one or more RAN protein peptide antigens. In some embodiments, a RAN protein peptide antigen comprises a unique C-terminal region of a RAN protein encoded by a CAG/CTG repeat expansion. In some embodiments, an anti-RAN protein antibody is an anti-polySer antibody or an anti-polyLeu antibody. In some embodiments, a RAN protein peptide antigen comprises a sequence set forth in any one of SEQ ID NOs: 17-26. In some embodiments, a subject is a mammalian cell, for example a B-cell or a hybridoma cell. In some embodiments, a subject is a mammal, for example a non-human primate, rodent (e.g., mouse rat, guinea pig, etc.), or a human.

An anti-RAN antibody can be a polyclonal antibody or a monoclonal antibody. Typically, polyclonal antibodies are produced by inoculation of a suitable mammal, such as a mouse, rabbit or goat. Larger mammals are often preferred as the amount of serum that can be collected is greater. An antigen is injected into the mammal. This induces the B-lymphocytes to produce IgG immunoglobulins specific for the antigen. This polyclonal IgG is purified from the mammal's serum. Monoclonal antibodies are generally produced by a single cell line (e.g., a hybridoma cell line). In some embodiments, an anti-RAN antibody is purified (e.g., isolated from serum). Examples of anti-RAN antibodies are disclosed, for example, in International Patent Application No. PCT/US2020/051671, filed Sep. 18, 2020, and in U.S. Publication No. 2013/0115603, the entire contents of each of which are incorporated herein by reference.

Numerous methods may be used for obtaining anti-RAN antibodies. For example, antibodies can be produced using recombinant DNA methods. Monoclonal antibodies may also be produced by generation of hybridomas (see e.g., Kohler and Milstein (1975) Nature, 256: 495-499) in accordance with known methods. Hybridomas formed in this manner are then screened using standard methods, such as enzyme-linked immunosorbent assay (ELISA) and surface plasmon resonance (e.g., OCTET or BIACORE) analysis, to identify one or more hybridomas that produce an antibody that specifically binds with a specified antigen. Any form of the specified antigen (e.g., a RAN protein) may be used as the immunogen, e.g., recombinant antigen, naturally occurring forms, any variants or fragments thereof. One exemplary method of making antibodies includes screening protein expression libraries that express antibodies or fragments thereof (e.g., scFv), e.g., phage or ribosome display libraries. Phage display is described, for example, in Ladner et al., U.S. Pat. No. 5,223,409; Smith (1985) Science 228:1315-1317; Clackson et al. (1991) Nature, 352: 624-628; Marks et al. (1991) J. Mol. Biol., 222: 581-597WO92/18619; WO 91/17271; WO 92/20791; WO 92/15679; WO 93/01288; WO 92/01047; WO 92/09690; and WO 90/02809.

In addition to the use of display libraries, the specified antigen (e.g., one or more RAN proteins) can be used to immunize a non-human animal, e.g., a rodent, e.g., a mouse, hamster, or rat. In one embodiment, the non-human animal is a mouse.

In another embodiment, a monoclonal antibody is obtained from the non-human animal, and then modified, e.g., made chimeric, using recombinant DNA techniques known in the art. A variety of approaches for making chimeric antibodies have been described. See e.g., Morrison et al., Proc. Natl. Acad. Sci. U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B.

Antibodies can also be humanized by methods known in the art. For example, monoclonal antibodies with a desired binding specificity can be commercially humanized (Scotgene, Scotland; and Oxford Molecular, Palo Alto, Calif.). Fully humanized antibodies, such as those expressed in transgenic animals, are within the scope of the invention (see, e.g., Green et al. (1994) Nature Genetics 7, 13; and U.S. Pat. Nos. 5,545,806 and 5,569,825).

For additional antibody production techniques, see Antibodies: A Laboratory Manual, Second Edition. Edited by Edward A. Greenfield, Dana-Farber Cancer Institute, ©2014. The present disclosure is not necessarily limited to any particular source, method of production, or other special characteristics of an antibody.

Also encompassed by the disclosure are hybridoma cell lines producing a monoclonal antibody specific for a di-amino acid repeat-containing protein selected from polySer or polyLeu, a C-terminal peptide of a di-amino acid repeat-containing protein as described herein, and/or a combination of two or more thereof.

Methods

Aspects of the disclosure relate to methods for identifying a subject (e.g., a human subject) as having or being at risk of developing certain neurodegenerative diseases, for example CAG•CTG expansion repeat-associated diseases.

In some embodiments, the disclosure provides a method for identifying a subject as having a CAG. CTG expansion repeat-associated disease, the method comprising detecting in a biological sample obtained from a subject one or more RAN proteins using an immunoassay that comprises an anti-RAN protein antibody that binds to a homopolymeric repeat region of the RAN protein; and determining that the subject has the disease based upon the presence of anti-RAN protein antibodies in the biological sample.

The disclosure relates, in some aspects, to methods of monitoring a therapeutic treatment course for a disease associated with a CAG•CTG expansion repeat, for example a spinocerebellar ataxia (SCA) (e.g., SCA1, SCA2, SCA3, SCA6, SCAT, SCAB, SCA12, SCA17, etc.), Huntington's disease (HD), Huntington disease-like 2 (HDL2), Dentato-rubral-pallidoluysian atrophy (DRPLA), Spinal-bulbar muscular atrophy (SBMA), Fuchs' endothelial corneal dystrophy (FECD), myotonic dystrophy (DM1), etc. In some aspects, the disclosure provides methods of treating a disease associated with a CAG•CTG expansion repeat comprising administering an effective amount of a therapeutic agent to a subject who has been determined to exhibit increased RAN protein translation (e.g., relative to a subject not having a disease or disorder associated with RAN protein translation) and determining (e.g., detecting) levels of one or more anti-RAN protein antibodies as measured by an immunoassay as described herein.

In some embodiments, the subject has previously been administered a therapeutic agent (e.g., prior to the determining). In some embodiments, the therapeutic agent administered to the subject according to the methods of the present invention is different from the previously administered therapeutic agent. In some embodiments, a subject is administered an increased or decreased dose of a therapeutic agent based on detection of an elevated or reduced level of RAN proteins in a biological sample as measured by an immunoassay.

Methods and kits described by the disclosure are capable of measuring levels of RAN proteins in a subject over a specified time period (e.g., longitudinally over a course of treatment), thereby providing an assessment of therapeutic efficacy of certain treatments (e.g., therapeutic agents for treating a CAG•CTG expansion repeat-associated disease).

In some aspects, the disclosure relates to a method for measuring pharmacokinetic changes in RAN protein levels in a subject. In some embodiments, the method comprises detecting in a first biological sample obtained from a subject one or more RAN proteins using an immunoassay comprising an anti-RAN protein antibody that targets a RAN protein homopolymeric repeat; detecting in a second biological sample obtained from the subject one or more RAN proteins using an immunoassay comprising an anti-RAN protein antibody that targets a RAN protein homopolymeric repeat, wherein the second biological sample is obtained after administration of a therapeutic agent to the subject; and determining that administration of the therapeutic agent to the subject results in a change in one or more RAN protein levels in the subject if the amount of RAN proteins detected in the second biological sample is different than the amount of RAN proteins detected in the first biological sample. In some embodiments, administration of the therapeutic agent to the subject results in a change in one or more RAN protein levels in the subject if the amount of RAN proteins detected in the second biological sample is less than the amount of RAN proteins detected in the first biological sample. administration of the therapeutic agent to the subject results in a change in one or more RAN protein levels in the subject if the amount of RAN proteins detected in the second biological sample is more than the amount of RAN proteins detected in the first biological sample.

Without wishing to be bound by any particular theory, detection (e.g., quantification of RAN protein levels) in the biological samples can be used to determine the effectiveness of a therapeutic agent or regime in the subject from which the samples are obtained. For example, measuring a decreased level of one or more RAN proteins in a subject after administration of a therapeutic agent for treatment of a CAG•CTG expansion repeat-associated disease (e.g., relative to the level of RAN proteins measured in the subject prior to the administration) is indicative of the therapeutic agent effectively treating the subject for the CAG•CTG expansion repeat-associated disease. Measuring an elevated level of one or more RAN proteins in a subject after administration of a therapeutic agent for treatment of a CAG. CTG expansion repeat-associated disease (e.g., relative to the level of RAN proteins measured in the subject prior to the administration) is indicative of the therapeutic agent not effectively treating the subject for the CAG•CTG expansion repeat-associated disease.

As used herein, "unchanged or elevated" means that the level of one or more RAN proteins present in a biological sample (e.g., a serum sample) is at or above (e.g., more than) a control level, such as a pre-determined threshold or a level of one or more RAN proteins in a control sample. Controls and control levels include RAN protein levels obtained (e.g., detected) from a subject that does not have or is not suspected of having a disease or disorder associated with RAN protein expression, translation, and/or accumulation (e.g., HD, SCA, DM1, etc.). In some embodiments, a control or control level includes RAN protein levels prior to administration of a therapeutic agent (e.g., an anti-RAN protein antibody). An unchanged level is a level that is the same as a control level. An elevated level includes a level that is, for example, 1%, 5%, 10%, 20%, 30%, 40%, 50%, 60%, 70%, 80%, 90%, 100%, 150%, 200%, 300%, 400%, 500%, or more than 500% above a control level. An elevated level also includes increasing a phenomenon from a zero state (e.g., no or undetectable RAN protein expression or level) to a non-zero state (e.g., some or detectable level of RAN antibody expression or presence). In some embodiments, a lack of change or an increase (e.g., lack of change or increase in the level of one or more RAN protein levels in the sample relative to a control or a prior sample) can be indicative of the lack of therapeutic efficacy of a therapeutic agent (e.g., lack of therapeutic efficacy in the subject from which the sample was obtained). In some embodiments, measuring a lack of change or an elevated level of one or more RAN proteins in a subject after administration of a therapeutic agent for treatment of a disease or disorder associated with RAN protein expression, translation, and/or accumulation (e.g., HD, SCA, DM1, etc.) (e.g., relative to the level of RAN proteins measured in the subject prior to the administration) is indicative of the therapeutic agent not effectively treating the subject for the disease or disorder associated with RAN protein expression, translation, and/or accumulation.

As used herein, "decreased" means that the level of one or more RAN proteins is below (e.g., less than) a control level, such as a pre-determined threshold or a level of one or more RAN proteins in a control sample. Controls and control levels include RAN protein levels obtained (e.g., detected) from a subject that does not have or is not suspected of having a disease or disorder associated with RAN protein expression, translation, and/or accumulation (e.g., HD, SCA, DM1, etc.). In some embodiments, a control or control level includes RAN protein levels prior to administration of a therapeutic agent (e.g., an anti-RAN protein antibody). A decreased level includes a level that is, for example, 1%, 5%, 10%, 20%, 30%, 40%, 50%, 60%, 70%, 80%, 90%, 100%, 150%, 200%, 300%, 400%, 500%, or more than 500% below a control level. A decreased level also includes decreasing a phenomenon from a non-zero state (e.g., some or detectable RAN protein expression or presence) to a zero state (e.g., no or undetectable RAN protein expression or presence). In some embodiments, a decrease (e.g., decrease in the level of one or more RAN protein levels in the sample relative to a control or a prior sample) can be indicative of the therapeutic efficacy of a therapeutic agent (e.g., therapeutic efficacy in the subject from which the sample was obtained). In some embodiments, measuring a decreased level of one or more RAN proteins in a subject after administration of a therapeutic agent for the treatment of a disease or disorder associated with RAN protein expression, translation, and/or accumulation (e.g., HD, SCA, DM1, etc.) (e.g., relative to the level of RAN proteins measured in the subject prior to the administration) is indicative of the therapeutic agent effectively treating the subject for the disease or disorder associated with RAN protein expression, translation, and/or accumulation.

As used herein, a "change" in one or more RAN protein levels in the subject occurs if the amount of RAN proteins detected in the first biological sample is different than the amount of RAN proteins detected in the second biological sample. The amount of RAN proteins detected in the first biological sample is considered "different" than the amount of RAN proteins detected in the second biological sample when either an elevated or a decreased level of one or more RAN proteins is observed in the second biological sample relative to the first biological sample.

In some embodiments, if the level (e.g., amount) of RAN proteins detected in the post-treatment sample is decreased compared to the pre-treatment level (e.g., amount) of RAN proteins, the therapeutic regimen is successful. In some embodiments, if the level (e.g., amount) of RAN proteins detected in the post-treatment sample is unchanged or increased compared to the pre-treatment level (e.g., amount) of RAN proteins, the therapeutic regimen is not successful. In some embodiments, the level of RAN proteins in biological samples (e.g., 1, 2, 3, 4, 5, 6, 7, 8, 9, 10, or more than 10 samples) obtained from a subject are continuously monitored during a therapeutic regimen (e.g., measured on 1, 2, 3, 4, 5, 6, 7, 8, 9, 10, or more than 10 separate occasions).

The time between which a first biological sample and a second biological sample are obtained may vary. In some embodiments, a first biological sample is obtained between 1 week and 1 minute prior to administration of a therapeutic agent (e.g., the first administration of a therapeutic agent). In some embodiments, a first biological sample is obtained between 1 day (e.g., 24 hours) and 1 minute prior to administration of a therapeutic agent (e.g., the first administration of a therapeutic agent). In some embodiments, a second biological sample is obtained from the subject between 1 minute and six months after administration of a therapeutic agent (e.g., the first administration of a therapeutic agent). In some embodiments, a second biological sample is obtained from the subject between 1 day and 1 week after administration of a therapeutic agent (e.g., the first administration of a therapeutic agent). In some embodiments, a second biological sample is obtained from the subject between 1 day and 1 week after administration of a therapeutic agent (e.g., the most recent or last administration of a therapeutic agent).

In some embodiments, a second biological sample may be collected about 1 hour, 5 hours, 10 hours, 24 hours (e.g., 1 day), 48 hours (e.g., 2 days), 120 hours (e.g., 5 days), 30 days, 45 days, or six months after administration of the therapeutic agent. In some embodiments, several biological samples (e.g., 2, 3, 4, 5, 6, 7, 8, 9, 10, or more biological samples) are obtained from the subject, for example over a specified timeframe (e.g., during a therapeutic course) and one or more RAN proteins are detected.

In some embodiments, methods described by the disclosure comprise a step of administering, continuing to administer, or stopping administration of a therapeutic agent (e.g., an agent for treatment of a CAG•CTG expansion repeat-associated disease) to the subject if the level of RAN proteins detected in the biological sample (e.g., a second biological sample) is changed relative to a level of RAN proteins detected in a control sample (e.g., a first biological sample). In some embodiments, methods described by the disclosure comprise a step of administering or continuing to administer a therapeutic agent (e.g., an agent for treatment of a CAG•CTG expansion repeat-associated disease) to the subject if the level of RAN proteins detected in the biological sample (e.g., a second biological sample) is decreased compared to a level of RAN proteins detected in a control sample (e.g., a first biological sample) (e.g., if the level of RAN proteins detected did not change or decreased following administration of the therapeutic agent). In some embodiments, methods described by the disclosure comprise a step of stopping the administration of a therapeutic agent (e.g., an agent for treatment of a CAG•CTG expansion repeat-associated disease) to the subject if the level of RAN proteins detected in the biological sample (e.g., a second biological sample) is elevated compared to a level of RAN proteins detected in a control sample (e.g., a second biological sample) (e.g., if the level of RAN proteins detected increased following administration of the therapeutic agent).

As used herein, "treat" or "treatment" refers to (a) preventing or delaying the onset of a disease or disorder associated with RAN proteins; (b) reducing the severity of a disease or disorder associated with RAN proteins; (c) reducing or preventing development of symptoms characteristic of a disease or disorder associated with RAN proteins; (d) preventing worsening of symptoms characteristic of a disease or disorder associated with RAN proteins; and/or (e) reducing or preventing recurrence of symptoms in subjects that were previously symptomatic for a disease or disorder associated with RAN proteins.

For example, in the context of HD, "treat" or "treatment" refers to (a) preventing or delaying the onset of HD; (b) reducing the severity of HD; (c) reducing or preventing development of symptoms characteristic of HD; (d) preventing worsening of symptoms characteristic of HD; and/or (e) reducing or preventing recurrence of HD symptoms in subjects that were previously symptomatic for HD.

A subject may be administered a therapeutically effective amount of one or more therapeutic agents. As used herein, an "effective amount" is a dosage of a therapeutic agent sufficient to provide a medically desirable result, such as treatment or amelioration of one or more signs or symptoms caused by a disease or disorder associated with RAN protein translation or accumulation (e.g., a neurodegenerative disease).

In certain embodiments, the effective amount is an amount effective in reducing the level of RAN proteins by at least 10%, at least 20%, at least 30%, at least 40%, at least 50%, at least 60%, at least 70%, at least 80%, at least 90%, at least 95%, or at least 98% (e.g., the level of RAN proteins relative to the level of RAN proteins in a cell or subject that has not been administered a therapeutic agent). In certain embodiments, the effective amount is an amount effective in reducing the translation of RAN proteins by at least 10%, at least 20%, at least 30%, at least 40%, at least 50%, at least 60%, at least 70%, at least 80%, at least 90%, at least 95%, or at least 98% (e.g., the level of RAN proteins relative the level of RAN proteins in a cell or subject that has not been administered a therapeutic agent). In certain embodiments, the effective amount is an amount effective in reducing RAN protein expression by at least 10%, at least 20%, at least 30%, at least 40%, at least 50%, at least 60%, at least 70%, at least 80%, at least 90%, at least 95%, or at least 98% (e.g., the level of RAN proteins relative the level of RAN proteins in a cell or subject that has not been administered a therapeutic agent). In certain embodiments, the effective amount is an amount effective in reducing RAN protein aggregation by at least 10%, at least 20%, at least 30%, at least 40%, at least 50%, at least 60%, at least 70%, at least 80%, at least 90%, at least 95%, or at least 98% (e.g., the level of RAN proteins relative the level of RAN proteins in a cell or subject that has not been administered a therapeutic agent).

The effective amount will vary with the age and physical condition of the subject being treated, the severity of the disease or disorder (e.g., the amount of RAN protein accumulation, or cellular toxicity caused by such an accumulation) in the subject, the duration of the treatment, the nature of any concurrent therapy, the specific route of administration and the like factors within the knowledge and expertise of the health practitioner. In some embodiments, a therapeutically effective amount is an amount of a vaccine sufficient to elicit production of anti-RAN protein antibodies in a subject.

Kits

In some aspects, the disclosure provides a kit comprising a first container containing one or more anti-RAN protein antibodies as described herein, and a second container containing one or more detectable reagents. In some embodiments, one or more anti-RAN antibodies bind to one or more homopolymeric repeat regions of a RAN protein, for example a polyLeucine repeat region or a polySerine repeat region. In some embodiments, the one or more detectable reagents comprise a Ruthenium complex, for example Ruthenium (II) tris-bipyridine-(4-methylsulfone), also referred to as $[Ru(Bpy)_3]^{+2}$, or a salt thereof. In some embodiments, a kit comprises a third container containing a control sample. A control sample may be a negative control sample (e.g., a control sample that does not contain, or lacks, one or more RAN proteins) or a positive control sample (e.g., a control sample that comprises one or more RAN proteins, optionally wherein the amount of the one or more RAN proteins in the sample is known).

EXAMPLE

This example describes detection of repeat associated non-ATG (RAN) protein translation in biological samples of a subject. RAN proteins may be translated from expansion repeat regions associated with several neurodegenerative diseases, as shown in FIG. 1. In some embodiments, an expansion repeat region comprises a CAG repeat expansion and/or a CTG repeat expansion. Novel antibodies (e.g., polyclonal antibodies) that target homopolymeric repeat regions of RAN proteins, such as polySerine and polyLeucine RAN proteins, were produced. The antibodies that target the repeat-regions are referred to herein as "anti-POLYSER" and "anti-POLYLEU". Antibodies targeting homopolymeric repeat regions offer the advantage of being able to detect RAN proteins produced in variety of CAG•CTG repeat associated diseases (FIG. 3). However, it is generally difficult to produce such antibodies because homopolymeric repeat proteins often lack the structural complexity required to elicit an immunogenic response in a host organism.

FIGS. 4-21 describe detection of polySerine RAN proteins in several neurodegenerative diseases, such as spinocerebellar ataxias (SCA) (e.g., SCA1, SCA2, SCA3, SCA6, SCA7, SCA8, etc.), Huntington's disease (HD), Huntington disease-like 2 (HDL2), Dentatorubral-pallidoluysian atrophy (DRPLA), Spinal-bulbar muscular atrophy (SBMA), Fuchs' endothelial corneal dystrophy (FECD), and myotonic dystrophy (DM1). RAN proteins were detected in both transfected cells and patient-derived samples by immunohistochemistry, immunofluorescence microscopy, and Western blot.

FIGS. 22-32 describe detection of polyLeucine RAN proteins in several neurodegenerative diseases, such as spinocerebellar ataxias (SCA) (e.g., SCA1, SCA2, SCA3, SCA6, SCA7, SCA8, etc.), Huntington's disease (HD), Huntington disease-like 2 (HDL2), Dentatorubral-pallidoluysian atrophy (DRPLA), Spinal-bulbar muscular atrophy (SBMA), Fuchs' endothelial corneal dystrophy (FECD), and myotonic dystrophy (DM1). RAN proteins were detected in both transfected cells and patient-derived samples by immunohistochemistry, immunofluorescence microscopy, and Western blot.

FIGS. 33 and 34 provide a summary of representative data shown in FIGS. 1-32.

The data contained herein demonstrate that novel polyLeu and polySer proteins are made from sense and antisense transcripts in seven CAG/CTG expansion disorders. It was also demonstrated that polyLeu and polySer proteins aggregate in human autopsy brains in SCA1, SCA2, SCA3, SCA6, SCA7, HDL2, and DM1 patients. Both the polyLeu and polySer proteins show frequent staining in affected brain regions—cerebellum for the SCAs, frontal cortex for DM1, and striatum for HDL2. Serial section staining as shown in the Figures shows that polyLeu and polySer repeats are present in regions with white matter alterations in SCA1, SCA2, SCA3, SCA6, SCA7, and DM1, with an established pathogenic abnormality in DM1. It is also shown herein that polyLeu and polySer are found in regions with microglial activation.

Figures 35A, 35B, 35C, 35D:
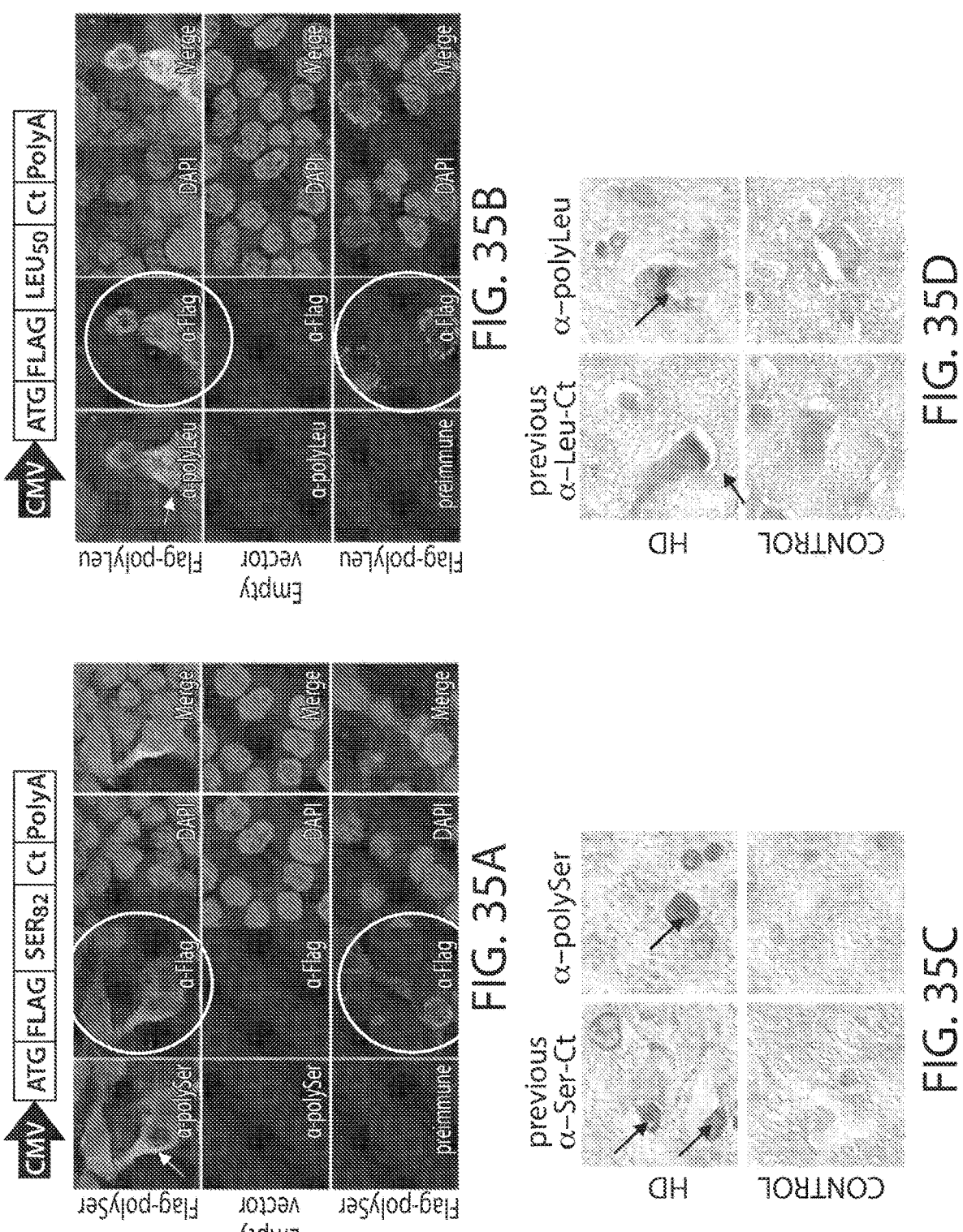
FIGS. 35A-35D show the validation of novel repeat antibodies against the Ser and Leu repeat motifs. Constructs used to express flag-tagged polySer and polyLeu repeat proteins were transfected on HEK293T cells.

FIGS. 35A-35D show the validation of novel repeat antibodies against the Ser and Leu repeat motifs. Constructs used to express flag-tagged polySer and polyLeu repeat proteins were transfected on HEK293T cells. FIGS. 35A and 35B show the immunofluorescence of transfected cells, which demonstrates co-localization of α-Flag (circled) and newly developed repeat antibodies: α-polySer (FIG. 35A) and α-polyLeu (FIG. 35B), shown with arrows. No signal was detected in cells transfected with an empty vector (middle row, FIGS. 35A and 35B) or when pre-immune sera were used as the primary antibody (bottom row, FIGS. 35A and 35B). FIGS. 35C and 35D show immunohistochemical experiments on HD frontal cortex, which validate the specificity of the newly generated repeat antibodies by comparing their signal with those obtained using the previously validated HD polySer and HD polyLeu C-terminal antibodies. Signal (arrows) was specifically detected in the HD samples (top row, FIGS. 35C and 35D), but not on the control samples (bottom row, FIGS. 35C and 35D).

Figure 36:
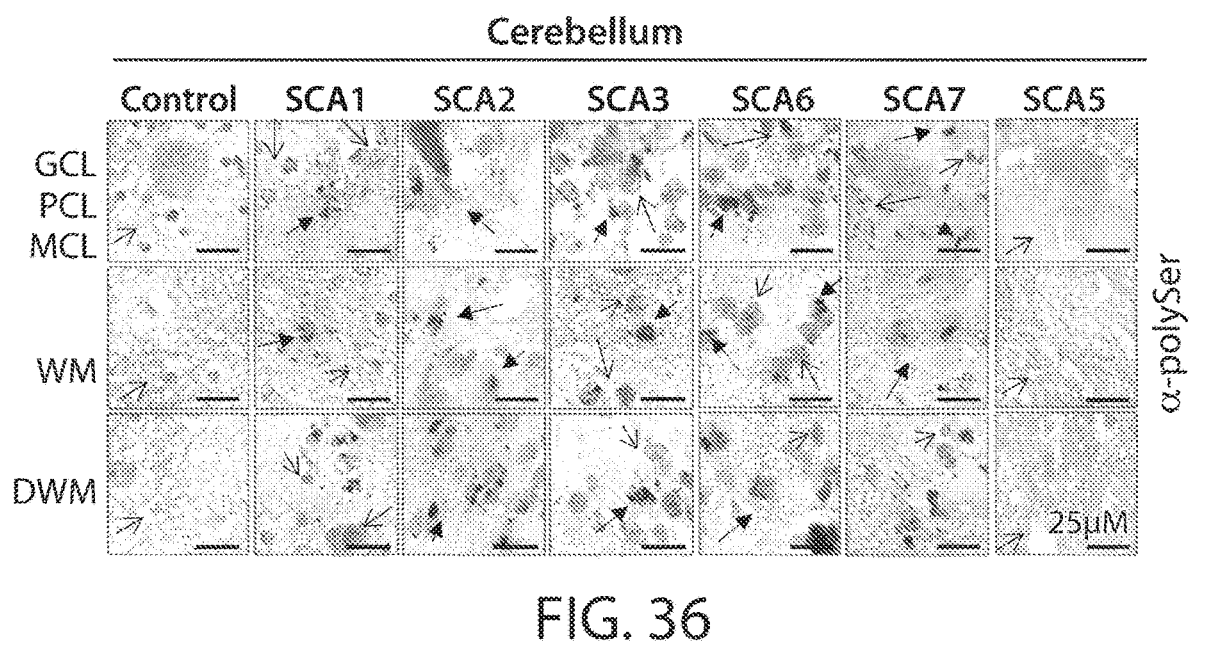

FIG. 36 shows RAN-polySer staining in SCA1, SCA2, SCA3, SCA6, SCA7, and SCA5 (negative control) human cerebellum. Immunohistochemistry shows polySer accumulation across the cerebellum. Positive regions include Bergmann glia, white matter (WM), and deep white matter (DWM) regions around the dentate nucleus. No signal was detected in non-affected or SCA5 negative controls. *arrows (→)=positive staining, arrows (→)=nuclear counterstain.

Figures 37A, 37B, 37C, 37D, 37E, 37F, 37G, 37H, 37I, 37J, 37K, 37L, 37M, 37N, 37O, 37P, 37Q, 37R, 37S, 37T, 37U:
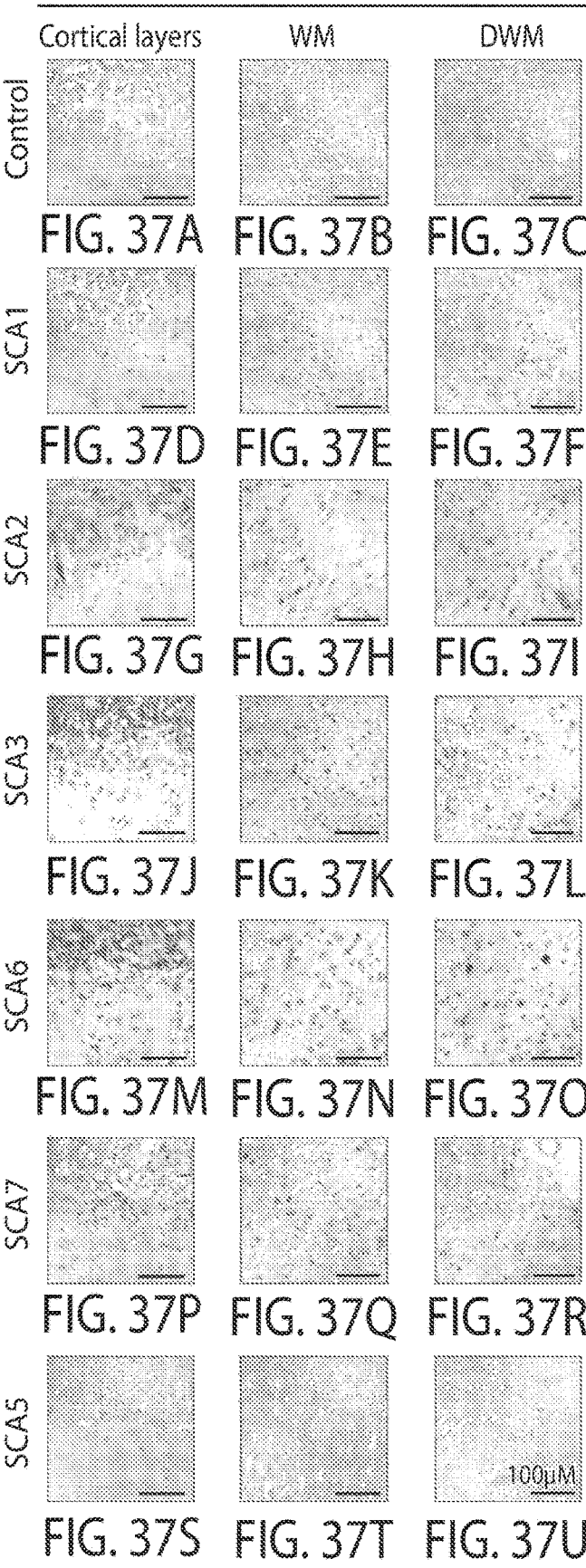
FIGS. 37A-37U show PolySer RAN proteins in SCA1, SCA2, SCA3, SCA6, SCA7, and SCA5 (negative control) human cerebellum. Immunohistochemical staining with α-Ser antibody shows intense and frequent nuclear and cytoplasmic signal in SCA1, SCA2, SCA3, SCA6, and SCA7 cerebellar regions. PolySer aggregates are prominently detected around the Bergmann glia (FIGS. 37D, 37G, 37J, 37M, 37P), cortical white matter regions (FIGS. 37E, 37H, 37K, 37N, 37Q), and more frequently in deep white matter regions close to the dentate nucleus (FIGS. 37F, 37I, 37L, 37O, 37R), with some variability between diseases and between cases. Healthy controls (FIGS. 37A-37C) and SCA5 (FIGS. 37S-37U) cases are negative for polyLeu signal.

FIGS. 37A-37U show PolySer RAN proteins in SCA1, SCA2, SCA3, SCA6, SCA7, and SCA5 (negative control) human cerebellum. Immunohistochemical staining with α-Ser antibody shows intense and frequent nuclear and cytoplasmic signal in SCA1, SCA2, SCA3, SCA6, and SCA7 cerebellar regions. PolySer aggregates are prominently detected around the Bergmann glia (FIGS. 37D, 37G, 37J, 37M, 37P), cortical white matter regions (FIGS. 37E, 37H, 37K, 37N, 37Q), and more frequently in deep white matter regions close to the dentate nucleus (FIGS. 37F, 37I, 37L, 37O, 37R), with some variability between diseases and between cases. Healthy controls (FIGS. 37A-37C) and SCA5 (FIGS. 37S-37U) cases are negative for polyLeu signal.

FIGS. 38A-38U show RAN PolyLeu accumulation in SCA1, SCA2, SCA3, SCA6, SCA7, and SCA5 (negative control) cerebellum. Immunostaining using an antibody against the polyLeu repeat motif shows frequent polyLeu aggregates. PolyLeu positive regions include Purkinje cells and Bergman glia (FIGS. 38D, 38G, 38J, 38M, 38P), cortical white matter (FIGS. 38E, 38H, 38K, 38N, 38Q), and neurons and glial cells around the dentate nucleus (FIGS. 38F, 38I, 38L, 38O, 38R). PolyLeu accumulation is more prominent in white matter regions. PolyLeu aggregates can be nuclear, cytoplasmic, or in the neuropil. Negative controls include healthy (FIGS. 38A-38C) and SCA5 (FIGS. 38S-38U) cases.

Figures 39A, 39B, 39C, 39D, 39E, 39F, 39G, 39H, 39I, 39J, 39K, 39L, 39M, 39N, 39O, 39P, 39Q, 39R, 39S, 39T, 39U:
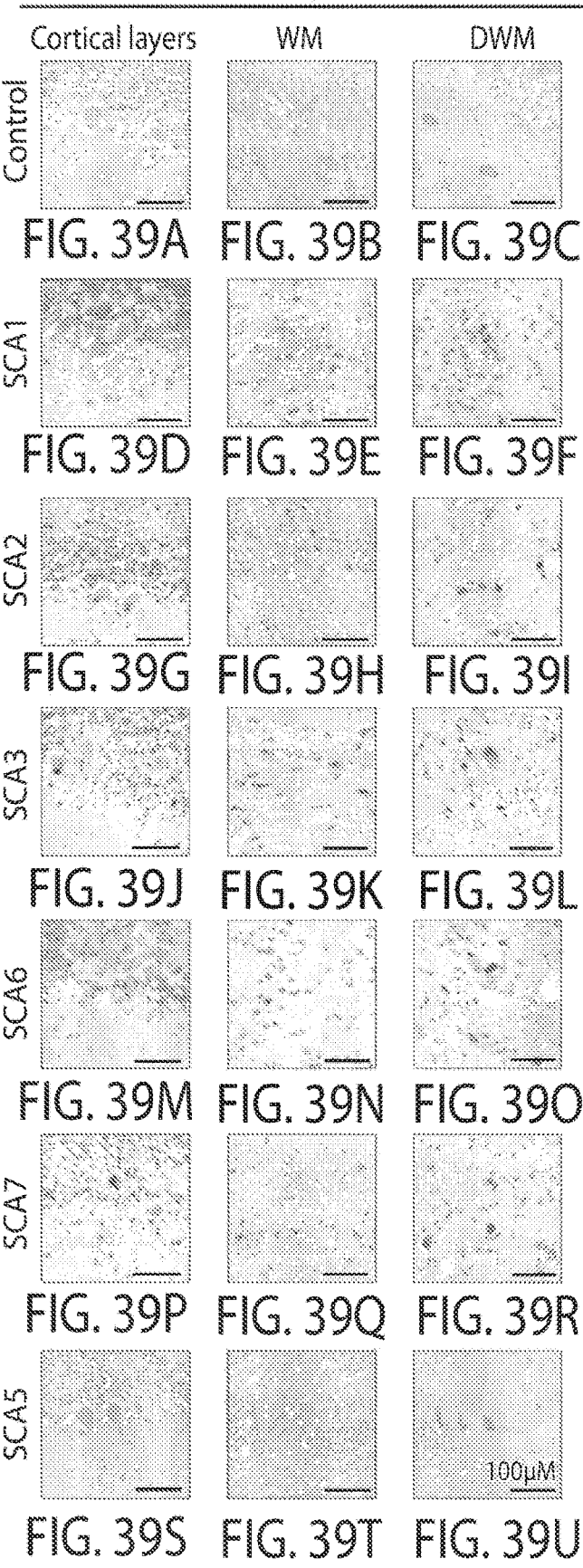
FIGS. 39A-39U show that RAN PolyLeu aggregates accumulate in the cerebellum of SCA1, SCA2, SCA3, SCA6, SCA7, and SCA5 (negative control) cases Immunohistochemistry shows polyLeu accumulation pattern and frequency. PolyLeu accumulates as nuclear, cytoplasmic, or neuropil aggregates. PolyLeu positive regions include Purkinje cells and Bergman glia (FIGS. 39D, 39G, 39J, 39M, 39P), cortical white matter (FIGS. 39E, 39H, 39K, 39N, 39Q), and neurons and glial cells around the dentate nucleus (FIGS. 39F, 39I, 39L, 39O, 39R). Negative controls include healthy (FIGS. 39A-39C) and SCA5 (FIGS. 39S-39U) cases.

FIGS. 39A-39U show that RAN PolyLeu aggregates accumulate in the cerebellum of SCA1, SCA2, SCA3, SCA6, SCA7, and SCA5 (negative control) cases Immunohistochemistry shows polyLeu accumulation pattern and frequency. PolyLeu accumulates as nuclear, cytoplasmic, or neuropil aggregates. PolyLeu positive regions include Purkinje cells and Bergman glia (FIGS. 39D, 39G, 39J, 39M, 39P), cortical white matter (FIGS. 39E, 39H, 39K, 39N, 39Q), and neurons and glial cells around the dentate nucleus (FIGS. 39F, 39I, 39L, 39O, 39R). Negative controls include healthy (FIGS. 39A-39C) and SCA5 (FIGS. 39S-39U) cases.

Figures 40A, 40B, 40C, 40D, 40E, 40F, 40G, 40H, 40I, 40J:
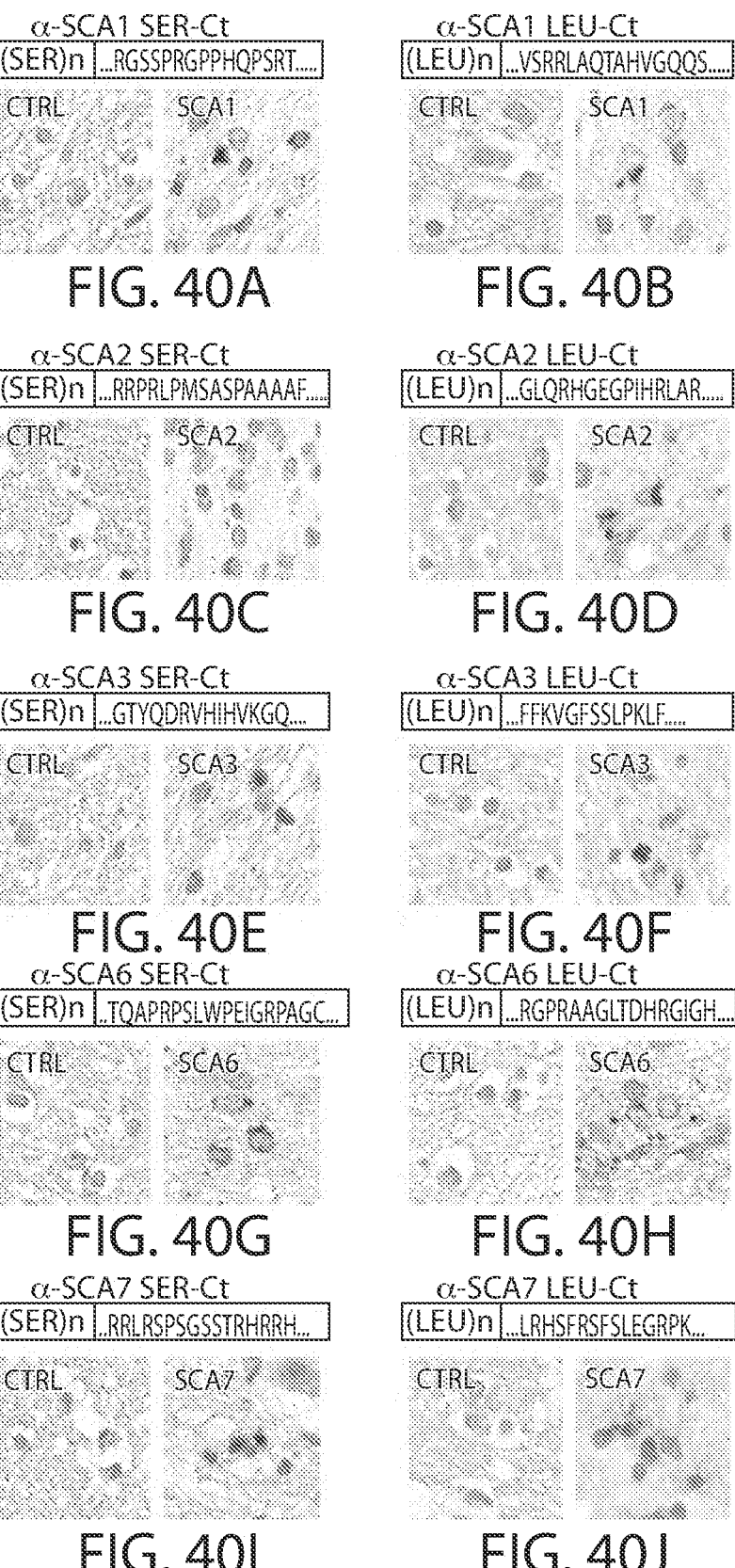
FIGS. 40A-40J show the detection of polySer and polyLeu RAN proteins in patient cerebellum using C-terminal antibodies. Immunohistochemistry shows polySer (FIGS. 40A, 40C, 40E, 40G, 40I) and polyLeu (FIGS. 40B, 40D, 40F, 40H, 40J) accumulation in white matter regions of SCA1, SCA2, SCA3, SCA6, and SCA7 cerebellum using antibodies against the unique C-terminal region for each protein. The epitope for each antibody is indicated in the grey box, and by the following sequence identifiers.

FIGS. 40A-40J show the detection of polySer and polyLeu RAN proteins in patient cerebellum using C-terminal antibodies. Immunohistochemistry shows polySer (FIGS. 40A, 40C, 40E, 40G, 40I) and polyLeu (FIGS. 40B, 40D, 40F, 40H, 40J) accumulation in white matter regions of SCA1, SCA2, SCA3, SCA6, and SCA7 cerebellum using antibodies against the unique C-terminal region for each protein. The epitope for each antibody is indicated in the grey box, and by the following sequence identifiers: FIG. 40A (SEQ ID NO: 17); FIG. 40B (SEQ ID NO: 18); FIG. 40C (SEQ ID NO: 19); FIG. 40D (SEQ ID NO: 20); FIG. 40E (SEQ ID NO: 21); FIG. 40F (SEQ ID NO: 22); FIG. 40G (SEQ ID NO: 23); FIG. 40H (SEQ ID NO: 24); FIG. 40I (SEQ ID NO: 25); and FIG. 40J (SEQ ID NO: 26) Immunohistochemistry using C-terminal antibodies demonstrates similar signal and RAN protein accumulation patterns as detected in immunohistochemical experiments that used the repeat antibodies.

Figures 41A, 41B, 41C, 41D, 41E, 41F, 41G, 41H:
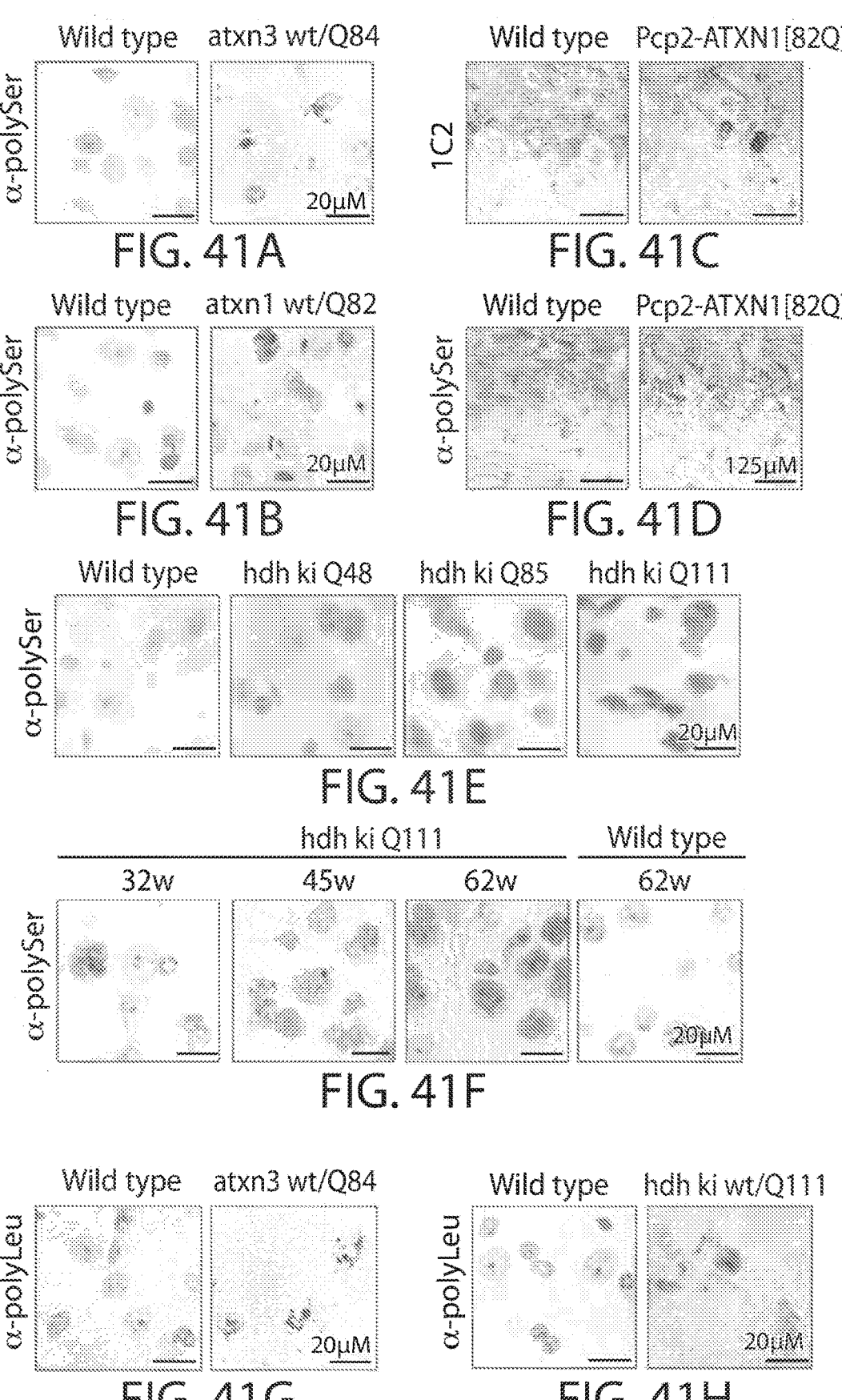
FIGS. 41A-41H show that polySer and polyLeu RAN proteins accumulate in SCA1, SCA3 and HD mice. Immunohistochemical staining of cortical regions of SCA3 (FIG. 41A) and SCA1 (FIG. 41B) mice show polySer accumulation as punctate aggregates.

FIGS. 41A-41H show that polySer and polyLeu RAN proteins accumulate in SCA1, SCA3 and HD mice. Immunohistochemical staining of cortical regions of SCA3 (FIG. 41A) and SCA1 (FIG. 41B) mice show polySer accumulation as punctate aggregates. FIGS. 41C and 41D show that PolySer is not detected on the pcp2-Atxn1 82Q mice, which specifically express the transgene in Purkinje cells, while polyGln detection in these cells is quite robust. FIGS. 41E and 41F show that polySer positive cells are detected in the cortex of HD knock-in mice. Immunohistochemistry on allelic series shows that polySer accumulation is more pronounced at longer CAG repeats (FIG. 41E) and increases with mouse age (FIG. 41F). Antisense RAN polyLeu aggregates are detected in SCA3 (FIG. 41G) and HD mice (FIG. 41H)

Figures 42A, 42B, 42C, 42D, 42E, 42F, 42G, 42H, 42I, 42J, 42K, 42L, 42M, 42N, 42O, 42P, 42Q, 42R, 42S, 42T, 42U, 42V, 42W, 42X, 42Y:
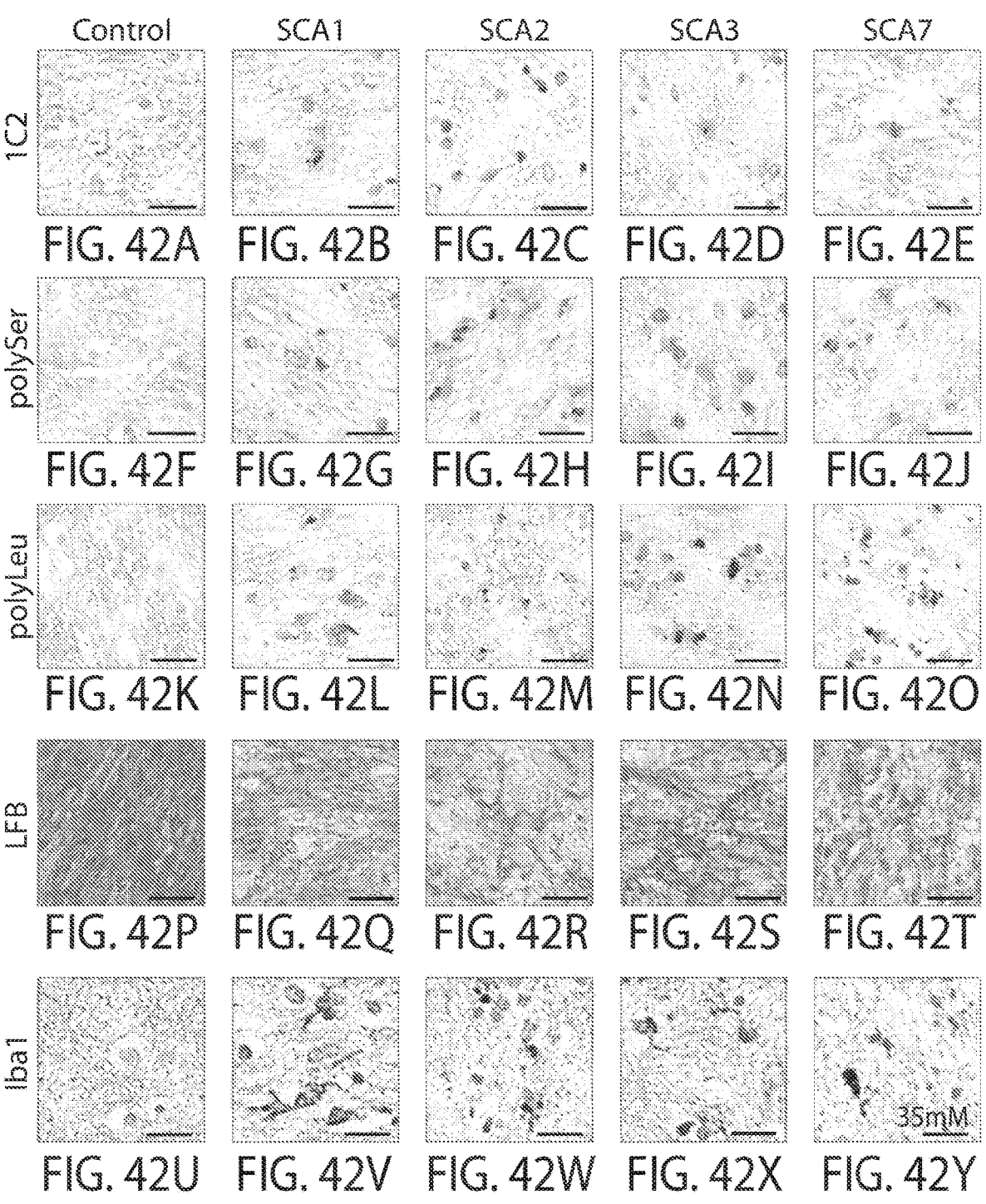

FIGS. 42A-42Y show that polySer and polyLeu RAN proteins accumulate in regions showing markers of pathology. Immunohistochemistry of serial sections shows that white matter regions with abundant RAN protein accumulation have increased microglial proliferation (ramified) and activation (ameboid), as indicated with Iba1 staining (FIGS. 42V-42Y). Regions with polySer and polyLeu RAN prominent accumulation display white matter integrity loss, as indicated with luxol fast blue staining (LFB) (FIGS. 42Q-42T). PolyGln aggregates are rare (1C2 staining; FIGS. 42B-42E)). FIGS. 42A-42E show IC2 staining of control (FIG. 42A), SCA1 (FIG. 42B), SCA2 (FIG. 42C), SCA3 (FIG. 42D), and SCA7 (FIG. 42E) tissue. FIGS. 42F-42J show polySer staining of control (FIG. 42F), SCA1 (FIG. 42G), SCA2 (FIG. 42H), SCA3 (FIG. 42I), and SCA7 (FIG. 42J). FIGS. 42K-42O show polyLeu staining of control (FIG. 42K), SCA1 (FIG. 42L), SCA2 (FIG. 42M), SCA3 (FIG. 42N), and SCA7 (FIG. 42O). FIGS. 42P-42T show LFB staining of control (FIG. 42P), SCA1 (FIG. 42Q), SCA2 (FIG. 42R), SCA3 (FIG. 42S), and SCA7 (FIG. 42T). FIGS. 42U-42Y show Iba1 staining of control (FIG. 42U), SCA1 (FIG. 42V), SCA2 (FIG. 42W), SCA3 (FIG. 42X), and SCA7 (FIG. 42Y).

Figures 43A, 43B, 43C, 43D, 43E, 43F, 43G, 43H, 43I, 43J, 43K, 43L, 43M, 43N, 43O, 43P, 43Q, 43R, 43S, 43T, 43U, 43V, 43W, 43X, 43Y:
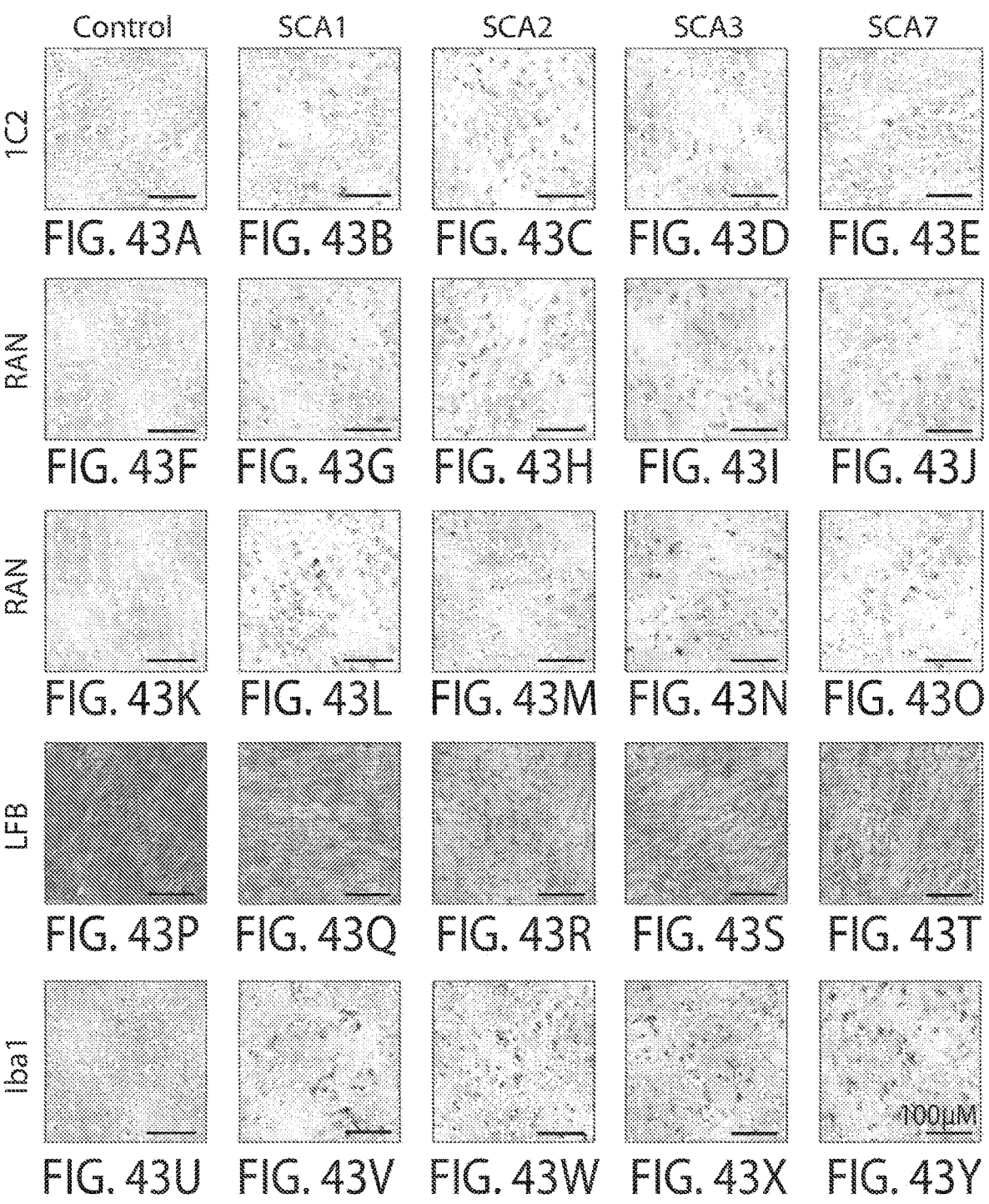

FIGS. 43A-43Y show that polySer and polyLeu RAN proteins accumulate in regions showing markers of pathology. Images show low magnification fields showing the frequency of RAN polySer and RAN polyLeu aggregates, microglial positive cells, the extent of white matter damage, and the low abundance of polyGln aggregates. FIGS. 43A-43E show IC2 staining of control (FIG. 43A), SCA1 (FIG. 43B), SCA2 (FIG. 43C), SCA3 (FIG. 43D), and SCA7 (FIG. 43E) tissue. FIGS. 43F-43J show polySer staining of control (FIG. 43F), SCA1 (FIG. 43G), SCA2 (FIG. 43H), SCA3 (FIG. 43I), and SCA7 (FIG. 43J). FIGS. 43K-43O show polyLeu staining of control (FIG. 43K), SCA1 (FIG. 43L), SCA2 (FIG. 43M), SCA3 (FIG. 43N), and SCA7 (FIG. 43O). FIGS. 43P-43T show LFB staining of control (FIG. 43P), SCA1 (FIG. 43Q), SCA2 (FIG. 43R), SCA3 (FIG. 43S), and SCA7 (FIG. 43T). FIGS. 43U-43Y show Iba1 staining of control (FIG. 43U), SCA1 (FIG. 43V), SCA2 (FIG. 43W), SCA3 (FIG. 43X), and SCA7 (FIG. 43Y).

Figures 44D, 44E, 44F:
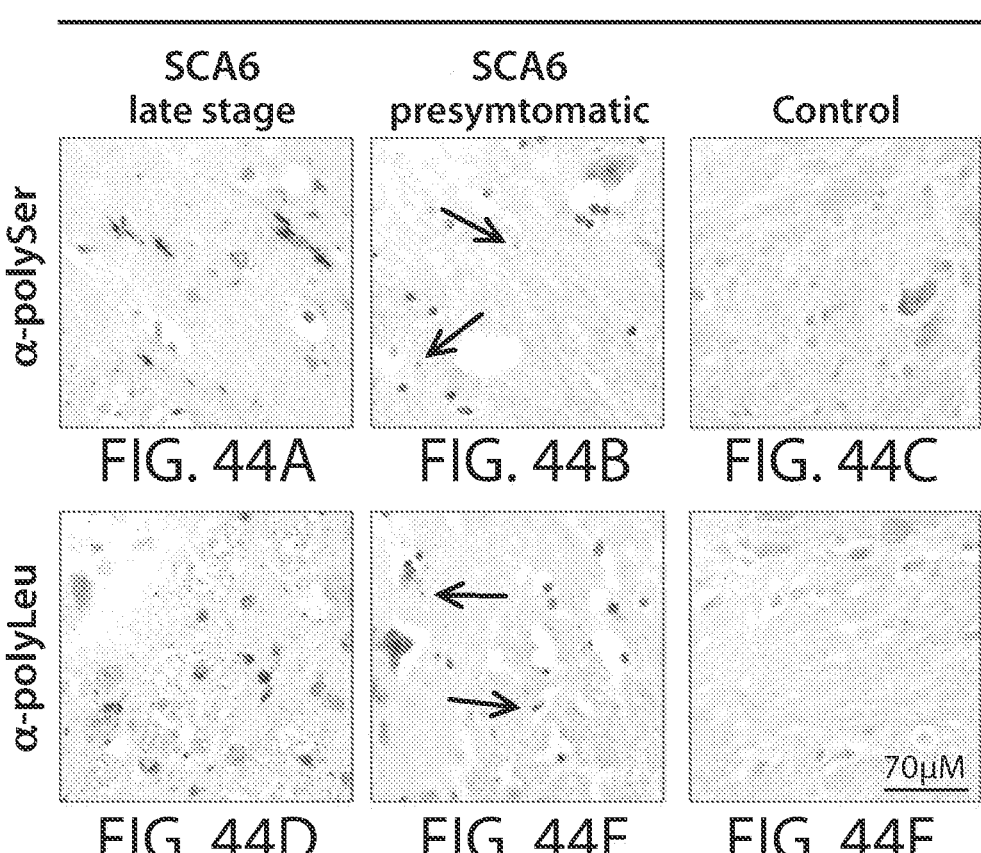

FIGS. 44A-44F show that polySer and polyLeu aggregates increase with disease progression Immunostaining of SCA6 human pons shows aggregates of RAN polySer and polyLeu proteins around pons white matter tracts (FIGS. 44A, 44B, 44D, and 44E). PolySer and polyLeu aggregates are variable in size and are frequently found in postmortem cases of late stage disease (FIGS. 44A and 44D). In contrast, postmortem cases with documented early death prior to disease show rare, smaller aggregates (FIGS. 44B and 44E). Healthy controls did not show any signal (FIGS. 44C and 44F).

What is claimed is:

1. A method of producing an antibody, the method comprising administering to a cell or a subject a peptide antigen consisting of the sequence set forth in any one of SEQ ID NOs: 17, 19-22, or 24-26.

2. The method of claim 1, further comprising the step of isolating the antibody from the subject.

3. The method of claim 1, wherein the cell is a mammalian cell.

4. The method of claim 3, wherein the mammalian cell is a B cell.

5. The method of claim 1, wherein the subject is mammal.

6. The method of claim 3, wherein the mammalian cell is a hybridoma cell.

7. A method of producing an antibody, the method comprising administering to a cell or a subject a peptide antigen comprising the sequence set forth in SEQ ID NO: 18 or 23.

8. The method of claim 7, further comprising the step of isolating the antibody from the subject.

9. The method of claim 7, wherein the cell is a mammalian cell.

10. The method of claim 9, wherein the mammalian cell is a B cell.

11. The method of claim 7, wherein the subject is mammal.

12. The method of claim 9, wherein the mammalian cell is a hybridoma cell.

* * * * *

SEQUENCE LISTING

```
<160> NUMBER OF SEQ ID NOS: 26

<210> SEQ ID NO 1
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 1

Ala Ala Ala Ala Ala Ala Ala Ala Ala Ala Ala Ala Ala Ala Ala Ala
1               5                   10                  15

Ala Ala Ala Ala
            20

<210> SEQ ID NO 2
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 2

Leu Leu Leu Leu Leu Leu Leu Leu Leu Leu Leu Leu Leu Leu Leu Leu
1               5                   10                  15

Leu Leu

<210> SEQ ID NO 3
<211> LENGTH: 20
```

-continued

```
<212> TYPE: PRT
<213> ORGANISM: Artificial Sequence
<220> FEATURE:
<223> OTHER INFORMATION: Synthetic polypeptide

<400> SEQUENCE: 3

Ser Ser Ser Ser Ser Ser Ser Ser Ser Ser Ser Ser Ser Ser Ser Ser
1               5                   10                  15

Ser Ser Ser Ser
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 4

Cys Cys Cys Cys Cys Cys Cys Cys Cys Cys Cys Cys Cys Cys Cys Cys
1               5                   10                  15

Cys Cys Cys Cys
            20

<210> SEQ ID NO 5
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (1)..(1)
<223> OTHER INFORMATION: n repeats

<400> SEQUENCE: 5

Ala Ala Pro Ala Ala Ala Pro Ala Ala Thr Arg Pro Gly Cys Gly
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (1)..(1)
<223> OTHER INFORMATION: n repeats

<400> SEQUENCE: 6

Ser Arg Pro Arg Arg His Pro Ala Arg Leu Trp Leu Arg Ser Arg
1               5                   10                  15

<210> SEQ ID NO 7
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (1)..(1)
<223> OTHER INFORMATION: n repeats

<400> SEQUENCE: 7

Gln Pro Pro Pro Pro Pro Pro Pro Pro Pro Pro Gln Leu Pro Gln
1               5                   10                  15
```

Pro Pro Pro

<210> SEQ ID NO 8
<211> LENGTH: 69
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (3)..(51)
<223> OTHER INFORMATION: may be absent

<400> SEQUENCE: 8

Met Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln Gln
            20                  25                  30

Gln Gln Gln Gln Gln Gln Gln Gln Gln Gln Gln Gln Gln Gln Gln
        35                  40                  45

Gln Gln Gln Pro Pro Pro Pro Pro Pro Pro Pro Pro Pro Gln Leu
    50                  55                  60

Pro Gln Pro Pro Pro
65

<210> SEQ ID NO 9
<211> LENGTH: 3
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: n repeats

<400> SEQUENCE: 9 cag                                                                                   3

<210> SEQ ID NO 10
<211> LENGTH: 6
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(6)
<223> OTHER INFORMATION: n repeats

<400> SEQUENCE: 10 cagctg                                                                                6

<210> SEQ ID NO 11
<211> LENGTH: 88
<212> TYPE: PRT
<213> ORGANISM: Artificial Sequence
<220> FEATURE:
<223> OTHER INFORMATION: Synthetic polypeptide

<400> SEQUENCE: 11

Ala Arg Arg Arg Asp Thr Arg Leu Ser Ser Ser Ser Ser Ser Ser
1               5                   10                  15

Ser Ser Ser Ser Ser Ile Ser Ile Ser Ser Ser Ser Ser Ser Ser
            20                  25                  30

-continued

```
Ser Ser Ser Ser Ser Ser Thr Ser Ala Gly Leu Arg Gly Ser Ser Pro
        35              40              45

Arg Gly Pro Pro His Gln Pro Ser Arg Thr Ser Thr Ser Thr Phe Pro
    50              55              60

Val Leu Arg Arg Thr Pro Ala Ala Pro Pro Leu Leu Arg Pro Ser Pro
65              70              75              80

Ser Thr Ser Thr Pro Thr Arg Arg
            85
```

```
<210> SEQ ID NO 12
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 12

Ser Pro Ser Ser Ser Ser Ser Ser Ser Ser Ser Ser Ser Ser Ser Asn
1               5               10              15

Ser Ser Ser Ser Ser Ser Ser Ser Ser Arg Arg Pro Arg Leu Pro Met
            20              25              30

Ser Ala Ser Pro Ala Ala Ala Ala Phe
        35              40
```

```
<210> SEQ ID NO 13
<211> LENGTH: 34
<212> TYPE: PRT
<213> ORGANISM: Artificial Sequence
<220> FEATURE:
<223> OTHER INFORMATION: Synthetic polypeptide
<220> FEATURE:
<221> NAME/KEY: SITE
<222> LOCATION: (1)..(1)
<223> OTHER INFORMATION: may repeat between 2 and n times

<400> SEQUENCE: 13

Ser Asn Ser Ser Ser Ser Ser Ser Ser Arg Gly Thr Tyr Gln Asp Arg
1               5               10              15

Val His Ile His Val Lys Gly Gln Pro Pro Val Gln Glu His Leu Gly
            20              25              30

Val Ile
```

```
<210> SEQ ID NO 14
<211> LENGTH: 212
<212> TYPE: PRT
<213> ORGANISM: Artificial Sequence
<220> FEATURE:
<223> OTHER INFORMATION: Synthetic polypeptide

<400> SEQUENCE: 14

Ser Ser Asn Ser Ser Ser Ser Ser Ser Ser Arg Gly Thr Tyr Gln Asp
1               5               10              15

Arg Val His Ile His Val Lys Gly Gln Pro Pro Val Gln Glu His Leu
            20              25              30

Gly Val Ile Arg Ala Gly Arg Pro Pro Ala Ala Leu Gly Gly Thr Gln
        35              40              45

Ala Pro Arg Pro Ser Leu Trp Pro Glu Ile Gly Arg Pro Arg Gly Ala
    50              55              60

Thr Ala Ala Ala Ala Arg Pro Gly Trp Arg Gly Gly Ser Gln Ala Arg
65              70              75              80
```

-continued

```
Pro Gly Ala Ser Pro Pro Gly Pro Val Asp Thr Ala Gly Pro Gly Gly
                85              90              95

Arg His Leu Ala Arg Thr Cys Pro Arg Gly Pro Arg Val Pro Gly Thr
            100             105             110

Met Ala Thr Thr Gly Ala Pro Thr Thr Thr Arg Pro Met Ala Arg Ala
            115             120             125

Ala Gly Ala Ala Arg Arg Pro Trp Pro Gly Pro Thr Thr Arg His Pro
    130             135             140

Pro Tyr Asp Thr Arg Pro Arg Ala Pro Pro Gly Ala Arg Pro Gly Leu
145             150             155             160

Pro Gly Pro Arg Ala Arg Pro Ala Pro Arg Leu Leu Gly Thr Ala Gly
            165             170             175

Asp Ser Pro Thr Ala Thr Thr Arg Arg Thr Asp Trp Pro Gly Pro Ala
            180             185             190

Gly Arg Ala Pro Gly Arg Ala Cys Thr Asn Pro Thr Ala Arg Val Thr
    195             200             205

Met Ile Gly Ala
    210
```

```
<210> SEQ ID NO 15
<211> LENGTH: 663
<212> TYPE: DNA
<213> ORGANISM: Artificial Sequence
<220> FEATURE:
<223> OTHER INFORMATION: Synthetic polypeptide

<400> SEQUENCE: 15
aggccggcgg ctcggggccc ccgcagcagc agcagcaggc ggtggccagg ccgggccggg      60
cggccaccag cggccctcgg aggtacccag gccccacggc cgagcctctg gccggagatc     120
ggccgcccac gggggggccac agcagcggcc gctcgcccag gatggagagg cgggtcccag     180
gcccggcccg gagcgagtcc cccagggcct gtcgacacgg cggggcccgg tggccggcat     240
ctggcccgca cgtgtccgag gggcccccgg gtccccggca ccatggctac taccgggggct    300 ccgactacga cgaggccgat ggcccgggca gcgggggcgg cgaggaggcc atggccgggg     360
cctacgacgc gccacccccc gtacgacacg cgtcctcggg cgccaccggg cgctcgccca     420
ggactccccg ggcctcgggc ccggcctgcg cctcgccttc tcggcacggc cggcgactcc     480
ccaacggcta ctacccggcg cacggactgg ccaggccccg cgggccgggc tccaggaagg     540
gcctgcacga accctacagc gagagtgacg atgattggtg caggatccct cgaggactac     600
aaagaccacg acggagatta caaagatcac gacatcgatt acaaggacga cgacgacaag     660
taa                                                                  663
```

```
<210> SEQ ID NO 16
<211> LENGTH: 130
<212> TYPE: PRT
<213> ORGANISM: Artificial Sequence
<220> FEATURE:
<223> OTHER INFORMATION: Synthetic polypeptide

<400> SEQUENCE: 16

Ser Ser Ser Ser Ser Ser Ser Ser Ser Ser Arg Gln Leu Pro Gly Phe
1               5               10              15

Arg Pro Arg Leu Cys Pro Glu Cys Gly Gly Ile Ser Val Arg Val Gly
            20              25              30

Leu Gly Pro Val Ala Val Leu Gln Pro Val Ala Pro Gly Pro Phe Val
        35              40              45
```

```
Phe Gly Pro Val Ala Arg Ala Leu Pro His Pro Val Ala Pro Leu Glu
    50                  55                  60

Ser Val Arg Pro Leu Ala Leu Val His Pro Leu Pro Leu Ala Leu Gln
65                  70                  75                  80

Ala Asp Ala Val Ala Leu Ala Leu Arg Pro Gly Ala Leu Val Arg Val
                85                  90                  95

Ala Ala Gly Pro Gly Val Asp Ala Gln His Leu Glu Ala Val Ala Pro
            100                 105                 110

Arg Ala Gly Val Phe Ala Leu Ala Leu Gly Ala Gly Ala Asp Ala Met
        115                 120                 125

Ala Val
    130

<210> SEQ ID NO 17
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 17

Arg Gly Ser Ser Pro Arg Gly Pro Pro His Gln Pro Ser Arg Thr
1               5                   10                  15

<210> SEQ ID NO 18
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 18

Val Ser Arg Arg Leu Ala Gln Thr His Val Gly Gln Gln Ser
1               5                   10

<210> SEQ ID NO 19
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 19

Arg Arg Pro Arg Leu Pro Met Ser Ala Ser Pro Ala Ala Ala Ala Phe
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 20

Gly Leu Gln Arg His Gly Glu Gly Pro Ile His Arg Leu Ala Arg
1               5                   10                  15

<210> SEQ ID NO 21
<211> LENGTH: 14
<212> TYPE: PRT
<213> ORGANISM: Artificial Sequence
<220> FEATURE:
<223> OTHER INFORMATION: Synthetic polypeptide
```

-continued

<400> SEQUENCE: 21

Gly Thr Tyr Gln Asp Arg Val His Ile His Val Lys Gly Gln
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 22

Phe Phe Lys Val Gly Phe Ser Ser Leu Pro Lys Leu Phe
1               5                   10

<210> SEQ ID NO 23
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 23

Thr Gln Ala Pro Arg Pro Ser Leu Trp Pro Glu Ile Gly Arg Pro Arg
1               5                   10                  15

Gly Cys

<210> SEQ ID NO 24
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 24

Arg Gly Pro Arg Ala Ala Gly Leu Thr Asp His Arg Gly Ile Gly His
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 25

Arg Arg Leu Arg Ser Pro Ser Gly Ser Ser Thr Arg His Arg Arg His
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 26

Leu Arg His Ser Phe Arg Ser Phe Ser Leu Glu Gly Arg Pro Lys
1               5                   10                  15